(12) United States Patent
Dinh et al.

(10) Patent No.: US 10,501,483 B2
(45) Date of Patent: Dec. 10, 2019

(54) ENAMINES AND DIASTEREO-SELECTIVE REDUCTION OF ENAMINES

(71) Applicant: Allergan, Inc., Irvine, CA (US)

(72) Inventors: Danny T. Dinh, Costa Mesa, CA (US); William R. Perrault, Kalamazoo, MI (US)

(73) Assignee: ALLERGAN, INC., Irvine, CA (US)

( * ) Notice: Subject to any disclaimer, the term of this patent is extended or adjusted under 35 U.S.C. 154(b) by 0 days.

(21) Appl. No.: 16/168,548

(22) Filed: Oct. 23, 2018

(65) Prior Publication Data

US 2019/0119304 A1 Apr. 25, 2019

Related U.S. Application Data

(60) Provisional application No. 62/576,388, filed on Oct. 24, 2017.

(51) Int. Cl.
  *C07D 471/10* (2006.01)
  *C07D 519/00* (2006.01)
  *C07D 498/10* (2006.01)

(52) U.S. Cl.
  CPC ........ *C07D 519/00* (2013.01); *C07D 471/10* (2013.01); *C07D 498/10* (2013.01)

(58) Field of Classification Search
  CPC ... C07D 471/10; C07D 487/10; C07D 498/10
  USPC .................... 546/16, 19; 540/543
  See application file for complete search history.

(56) References Cited

U.S. PATENT DOCUMENTS

| | | | |
|---|---|---|---|
| 9,187,451 B2 | 11/2015 | Congreve et al. | |
| 9,266,857 B2 | 2/2016 | Brown et al. | |
| 10,030,035 B2 * | 7/2018 | Congreve | C07D 471/10 |
| 2005/0176703 A1 | 8/2005 | Gabriel et al. | |
| 2014/0329803 A1 | 11/2014 | Congreve et al. | |
| 2015/0232443 A1 | 8/2015 | Brown et al. | |
| 2016/0068508 A1 | 3/2016 | Congreve et al. | |
| 2016/0128996 A1 | 5/2016 | Brown et al. | |

FOREIGN PATENT DOCUMENTS

| | | |
|---|---|---|
| WO | 9932489 | 7/1999 |
| WO | 2007067504 | 11/2007 |
| WO | 2013072705 | 5/2013 |
| WO | 2014045031 | 3/2014 |
| WO | 2015118342 | 8/2015 |
| WO | 2015140559 | 9/2015 |
| WO | 2016147011 | 9/2016 |

OTHER PUBLICATIONS

Adbel-Magid, A.F., et al., Reductive Amination of Aldehydes and Ketones with Sodium Triacetoxyborohydride. Studies on Direct and Indirect Reductive Amination Procedures, J. Org. Chem., 1996, 3849-3862, 61.

Barrulas, PC, et al., Cinchona-Derived Picolinamides: Effective Organocatalysts for Stereoselective Imine Hydrosilylation, Eur. J. Org. Chem., 2014, 7339-7342, 33.

Berge, Stephen M., Pharmaceutical Salts, Journal of Pharmaceutical Sciences, Jan. 1977, 1-19, 66 (1), US.

Bhattacharyya, S., Borohydride Reductions in Dichloromethane: A Convenient, Environmentally Compatible Procedure for the Methylation of Amines, Synthetic Communications, 1995, 2061-2069, 25(14).

Bowman, A.M. et al., An Efficient Reductive Amination Protoclol Using Benzylamine-Borane as Reducing Agent, BYU, 2017, pp. 1-2.

Gomez, S., et al., The Reductive Amination of Aldehydes and Ketones and the Hydrogenation of Nitriles: Mechanistic Aspects and Selectivity Control, Adv. Synth. Catal., 2002, 1037-1057, 344 (10).

Heinrich Stahl, Handbook of Pharmaceutical Salts, Properties, Selection, and Use, Handbook of Pharmaceutical Salts, Properties, Selection, and Use, 2002, 329-345, N/A.

Marciniec, B., Hydrosilylation, Advances in Silicon Science, 2009, pp. 1-424, 1, Springer, Poznan.

Mizuta, T., et al., Catalytic Reductive Alkylation of Secondary Amine with Aldehyde and Silane by an Iridium Compound, J. Org. Chem., 2005, 2195-2199, 70.

* cited by examiner

Primary Examiner — Charanjit Aulakh
(74) Attorney, Agent, or Firm — Jonathan Bass

(57) ABSTRACT

Described herein is a compound having a chemical structure of Formula A:

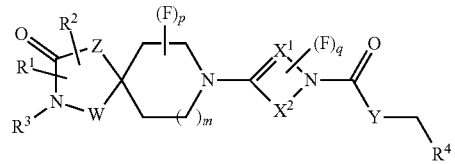

wherein m, p, q, W, Z, Y, $X^1$, $X^2$, $R^1$, $R^2$, $R^3$ and $R^4$ are as defined herein. A diastereo-selective reduction of the compound comprising contacting the compound of Formula A with a reducing agent in an aprotic polar or non-polar solvent is also described.

32 Claims, 1 Drawing Sheet

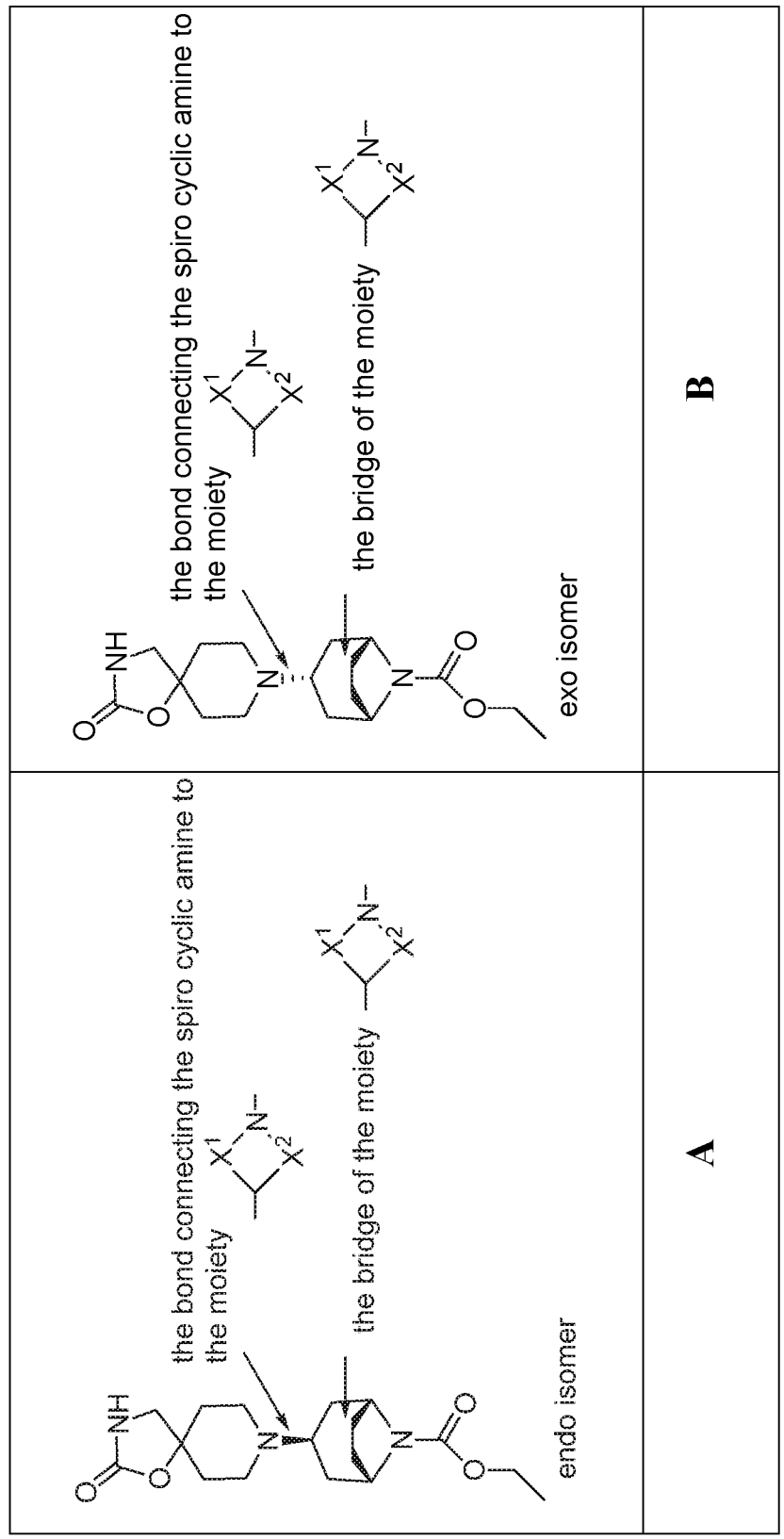

ENAMINES AND DIASTEREO-SELECTIVE REDUCTION OF ENAMINES

CROSS REFERENCE TO RELATED APPLICATIONS

This application claims the benefit of U.S. Provisional Patent Application 62/576,388 filed on Oct. 24, 2017 which is herein incorporated by reference in its entirety and serves as the basis of a priority and/or benefit claim for the present application.

TECHNICAL FIELD

This application relates to enamines, including isolated enamines. This application also relates to a diastereoselective reduction of isolated enamines into tertiary amines.

BACKGROUND

Muscarinic acetylcholine receptors are one of the two general types of acetylcholine receptors (the other being nicotinic acetylcholine receptors). The receptors are G protein-receptor complexes and there are five subtypes designated $M_1$ to $M_5$. Modulation of these of one or more of the muscarinic receptors can be useful in the treatment of conditions such as Alzheimer's disease, schizophrenia and other psychotic disorders, cognitive disorders and other diseases associated with the receptors.

International patent application PCT/GB2015/050807, published as WO 2015/140559, describes muscarinic receptor agonists. Given the importance of muscarinic receptor modulators as indicated above, there is a need for compounds that can be used in the syntheses of muscarinic receptor modulators (e.g. those of PCT/GB2015/050807), as well as for improved methods of synthesis of these compounds.

SUMMARY

Described herein compounds, and in particular enamines, which in some embodiments can be used as intermediates in the syntheses of the muscarinic receptor agonists. Described herein is also a method which isolated enamines are diastereoselectively reduced into tertiary amines which in some embodiments can be useful as muscarinic receptor agonists.

The following aspects and embodiments thereof described and illustrated below are meant to be exemplary and illustrative, not limiting in scope.

In one aspect, a compound of Formula A or a salt thereof is provided:

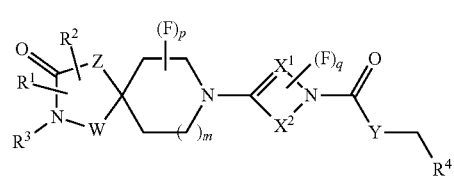

Formula A wherein:
m is 1 or 2;
p is 0, 1, or 2;
q is 0, 1, or 2;
W is C or N;
Z is $CH_2$, N, O, or S;
Y is NH, O, S, or CH2;
$X^1$ and $X^2$ are hydrocarbons which together contain a total of five to nine carbon atoms and which link together such that the moiety:

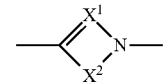

forms a bridged bicyclic ring system;
$R^1$ and $R^2$ are independently H, halo, CN, OH, $C_{2-6}$ alkenyl, $C_{2-6}$ alkynyl, $C_{1-6}$ alkyl, $C_{1-6}$ haloalkyl, $C_{1-3}$ alkoxy, $NR^5R^6$, $C_{3-6}$ cycloalkyl, $C_{3-6}$ cycloalkenyl, $NR^5R^6$, $COOR^5$, $CONR^5R^6$, $NR^7CONR^5R^6$, $NR^7COOR^5$, $OCONR^5R^6$, $SR^5$, $SOR^5$, $SO_2R^5$, or $C_{1-6}$ alkylene-E;
$R^3$ is H, OH, $C_{1-6}$ alkyl, $C_{1-6}$ haloalkyl, $C_{2-6}$ alkenyl, $C_{2-6}$ alkynyl, 3 to 6 membered cycloalkyl, heterocycloalkyl, aryl or heteroaryl, or $C_{1-6}$ alkylene-E;
or $R^1$ and $R^2$, or $R^3$ and $R^2$ together from a cycloalkyl or heterocycloalkyl each of which is optionally substituted with at least one group selected from OH, halo, CN, OH, $C_{1-6}$ alkyl, $C_{1-6}$ haloalkyl, $C_{1-3}$ alkoxy, and $NH_2$;
E is OH, $C_{1-3}$ alkoxy, $NR^5R^6$, $SR^5$, 3 to 6 membered cycloalkyl, heterocycloalkyl, aryl or heteroaryl;
$R^4$ is H, $C_{1-5}$ alkyl, $C_{2-5}$ alkenyl, $C_{2-5}$ alkynyl, $C_{3-6}$ cycloalkyl, or $C_{3-6}$ cycloalkenyl, each of the alkyl, alkenyl, alkynyl, cycloalkyl and cycloalkenyl is optionally substituted with at least one group selected from OH, halo, CN, $C_{1-3}$ alkoxy, and $NH_2$;
$R^5$, $R^6$, and $R^7$ are independently H or $C_{1-6}$ alkyl;
provided that when Z is O, $R^3$ is H.

In another aspect, an isolated compound of Formula A or a salt thereof is provided:

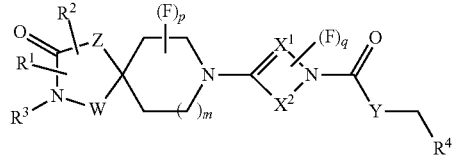

Formula A wherein:
m is 1 or 2;
p is 0, 1, or 2;
q is 0, 1, or 2;
W is C or N;
Z is $CH_2$, N, O, or S;
Y is NH, O, S, or CH2;
$X^1$ and $X^2$ are hydrocarbons which together contain a total of five to nine carbon atoms and which link together such that the moiety:

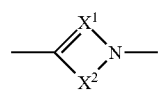

forms a bridged bicyclic ring system;
$R^1$ and $R^2$ are independently H, halo, CN, OH, $C_{2-6}$ alkenyl, $C_{2-6}$ alkynyl, $C_{1-6}$ alkyl, $C_{1-6}$ haloalkyl, $C_{1-3}$ alkoxy, $NR^5R^6$, $C_{3-6}$ cycloalkyl, $C_{3-6}$ cycloalkenyl, $NR^5R^6$, $COOR^5$, CONR$^5$R$^6$, NR$^7$CONR$^5$R$^6$, NR$^7$COOR$^5$, OCONR$^5$R$^6$, SR$^5$, SOR$^B$, SO$_2$R$^5$, or C$_{1-6}$ alkylene-E;

R$^3$ is H, OH, C$_{1-6}$ alkyl, C$_{1-6}$ haloalkyl, C$_{2-6}$ alkenyl, C$_{2-6}$ alkynyl, 3 to 6 membered cycloalkyl, heterocycloalkyl, aryl or heteroaryl, or C$_{1-6}$ alkylene-E;

or R$^1$ and R$^2$, or R$^3$ and R$^2$ together from a cycloalkyl or heterocycloalkyl each of which is optionally substituted with at least one group selected from OH, halo, CN, OH, C$_{1-6}$ alkyl, C$_{1-6}$ haloalkyl, C$_{1-3}$ alkoxy, and NH$_2$;

E is OH, C$_{1-3}$ alkoxy, NR$^5$R$^6$, SR$^5$, 3 to 6 membered cycloalkyl, heterocycloalkyl, aryl or heteroaryl;

R$^4$ is H, C$_{1-5}$ alkyl, C$_{2-5}$ alkenyl, C$_{2-5}$ alkynyl, C$_{3-6}$ cycloalkyl, or C$_{3-6}$ cycloalkenyl, each of the alkyl, alkenyl, alkynyl, cycloalkyl and cycloalkenyl is optionally substituted with at least one group selected from OH, halo, CN, C$_{1-3}$ alkoxy, and NH$_2$;

R$^5$, R$^6$, and R$^7$ are independently H or C$_{1-6}$ alkyl;
provided that when Z is O, R$^3$ is H.

In another aspect, a diastereo-selective reduction of an enamine into a compound (tertiary amine) of Formula B or a salt thereof is provided,

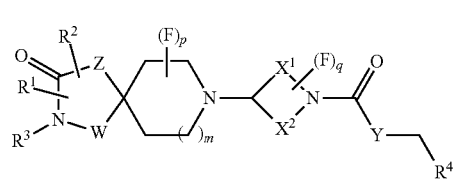

Formula B wherein R$^1$-R$^4$, Y, Z, W, m, p, and q are the same as described herein for Formula A, and X$^1$ and X$^2$ are hydrocarbons which together contain a total of five to nine carbon atoms and which link together such that the moiety:

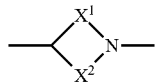

forms a bridged saturated bicyclic ring system. The method comprises contacting the isolated compound of Formula A with a reducing agent in an aprotic polar or non-polar solvent optionally comprising an acid.

Some non-limiting example embodiments are listed below.

Example Embodiment 1: An isolated compound of formula A:

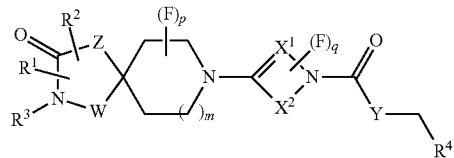

Formula A wherein:
m is 1 or 2;
is 0, 1, or 2;
q is 0, 1, or 2;
W is C or N;
Z is CH$_2$, N, O, or S;
Y is NH, O, S, or CH2;
X$^1$ and X$^2$ are hydrocarbons which together contain a total of five to nine carbon atoms and which link together such that the moiety:

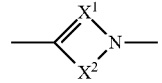

forms a bridged bicyclic ring system;

R$^1$ and R$^2$ are independently H, halo, CN, OH, C$_{2-6}$ alkenyl, C$_{2-6}$ alkynyl, C$_{1-6}$ alkyl, C$_{1-6}$ haloalkyl, C$_{1-3}$ alkoxy, NR$^5$R$^6$, C$_{3-6}$ cycloalkyl, C$_{3-6}$ cycloalkenyl, NR$^5$R$^6$, COOR$^5$, CONR$^5$R$^6$, NR$^7$CONR$^5$R$^6$, NR$^7$COOR$^5$, OCONR$^5$R$^6$, SR$^5$, SOR$^5$, SO$_2$R$^5$, or C$_{1-6}$ alkylene-E;

R$^3$ is H, OH, C$_{1-6}$ alkyl, C$_{1-6}$ haloalkyl, C$_{2-6}$ alkenyl, C$_{2-6}$ alkynyl, 3 to 6 membered cycloalkyl, heterocycloalkyl, aryl or heteroaryl, or C$_{1-6}$ alkylene-E;

or R$^1$ and R$^2$, or R$^3$ and R$^2$ together from a cycloalkyl or heterocycloalkyl each of which is optionally substituted with at least one group selected from OH, halo, CN, OH, C$_{1-6}$ alkyl, C$_{1-6}$ haloalkyl, C$_{1-3}$ alkoxy, and NH$_2$;

E is OH, C$_{1-3}$ alkoxy, NR$^5$R$^6$, SR$^5$, 3 to 6 membered cycloalkyl, heterocycloalkyl, aryl or heteroaryl;

R$^4$ is H, C$_{1-5}$ alkyl, C$_{2-5}$ alkenyl, C$_{2-5}$ alkynyl, C$_{3-6}$ cycloalkyl, or C$_{3-6}$ cycloalkenyl, each of the alkyl, alkenyl, alkynyl, cycloalkyl and cycloalkenyl is optionally substituted with at least one group selected from OH, halo, CN, C$_{1-3}$ alkoxy, and NH$_2$;

R$^5$, R$^6$, and R$^7$ are independently H or C$_{1-6}$ alkyl;
provided that when Z is O, R$^3$ is H.

Example Embodiment 2: The isolated compound of Example Embodiment 1, wherein R$^1$ is H, halo, CN, OH, C$_{1-4}$ alkyl, C$_{1-6}$ haloalkyl, C$_{1-3}$ alkoxy, NH$_2$, or C$_{1-6}$ alkylene-E, wherein E is C$_{1-3}$ alkoxy, 5 or 6 membered cycloalkyl, heterocycloalkyl, aryl, or heteroaryl.

Example Embodiment 3: The isolated compound of Example Embodiment 1, wherein R$^1$ is H, halo, CN, OH, C$_{1-4}$ alkyl, C$_{1-6}$ haloalkyl, C$_{1-3}$ alkoxy, NH$_2$, or C$_{1-2}$ alkylene-E, wherein E is methoxy, cyclopropyl, phenyl, or pyridinyl.

Example Embodiment 4: The isolated compound of any one of example embodiments 1-3, wherein R$^2$ is H, methyl, ethyl, propyl, isopropyl, or benzyl.

Example Embodiment 5: The isolated compound of any one of example embodiments 1-4, wherein R$^3$ is H, OH, C$_{1-6}$ alkyl, C$_{1-6}$ haloalkyl, C$_{2-6}$ alkenyl, C$_{2-6}$ alkynyl, C$_{3-6}$ cycloalkyl, 5 or 6 membered aryl or heteroaryl, or C$_{1-6}$ alkylene-E, wherein E is OH, C$_{1-3}$ alkoxy, NR$^5$R$^6$, SR$^5$, C$_{3-6}$ cycloalkyl, 5 or 6 membered aryl or heteroaryl.

Example Embodiment 6: The isolated compound of any one of example embodiments 1-5, wherein R$^4$ is H, C$_{1-5}$ alkyl, C$_{2-5}$ alkenyl, or C$_{2-5}$ alkynyl.

Example Embodiment 7: The isolated compound of any one of example embodiments 1-6, wherein p is 0 and q is 0.

Example Embodiment 8: The isolated compound of any one of example embodiments 1-7, wherein Z is CH$_2$, N, or O.

Example Embodiment 9: The isolated compound of Example Embodiment 8, wherein Z is CH$_2$.

Example Embodiment 10: The isolated compound of any one of example embodiments 1-9, wherein the moiety

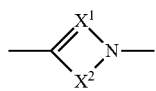

is an azabicyclo-heptene, azabicyclo-octene, or azabicyclo-nonene ring system.

Example Embodiment 11: The isolated compound of any one of example embodiments 1-9, wherein the moiety

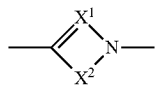

is selected from the following ring system wherein q is 0, 1, or 2:

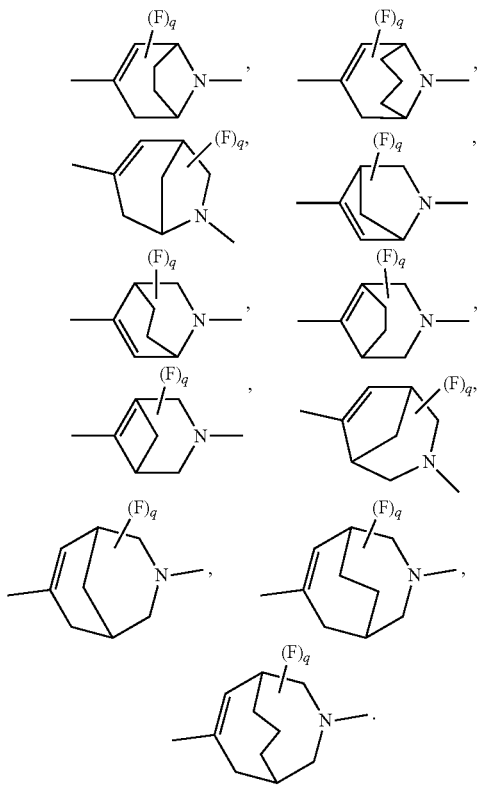

Example Embodiment 12: The isolated compound of Example Embodiment 11, wherein the moiety

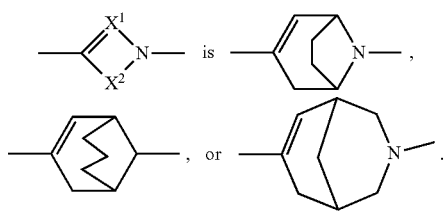

Example Embodiment 13: The isolated compound of Example Embodiment 12, wherein the moiety

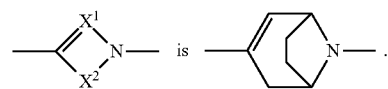

Example Embodiment 14: The isolated compound of any one of example embodiments 1-13, wherein R', $R^2$, and $R^3$ are independently H or $C_{1-3}$ alkyl, Z is $CH_2$, q is 0, and W is C.

Example Embodiment 15: The isolated compound of any one of example embodiments 1-14, wherein Y is O, and $R^4$ is methyl, fluoromethyl, ethyl, ethynyl, 2-butynyl, and 1-propynyl.

Example Embodiment 16: The isolated compound of Example Embodiment 1, which is selected from the following compounds:

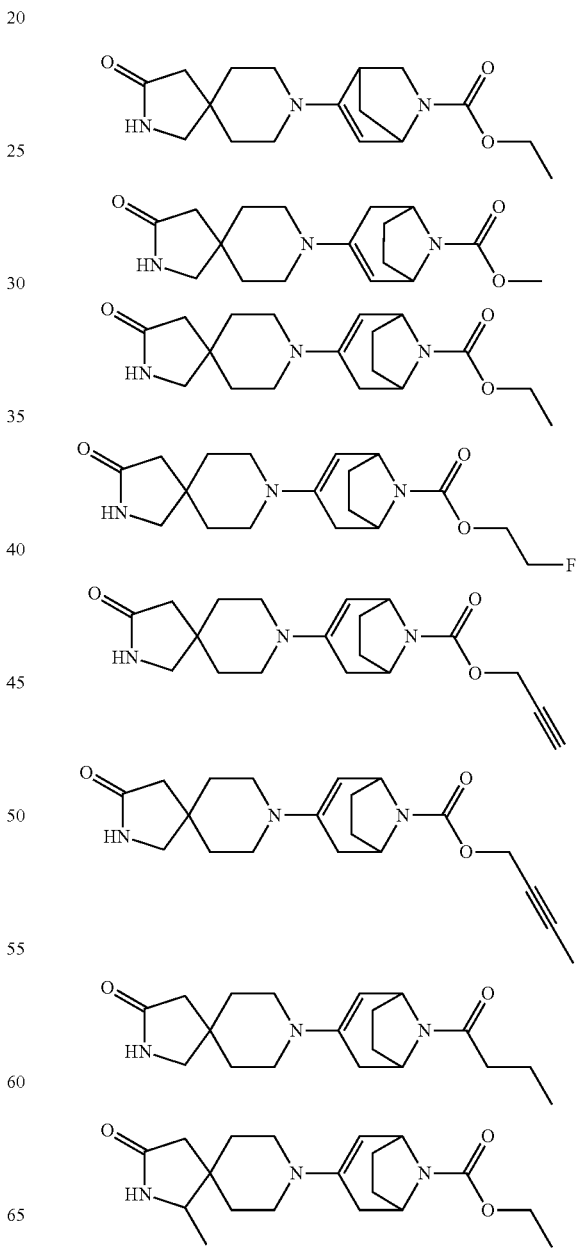

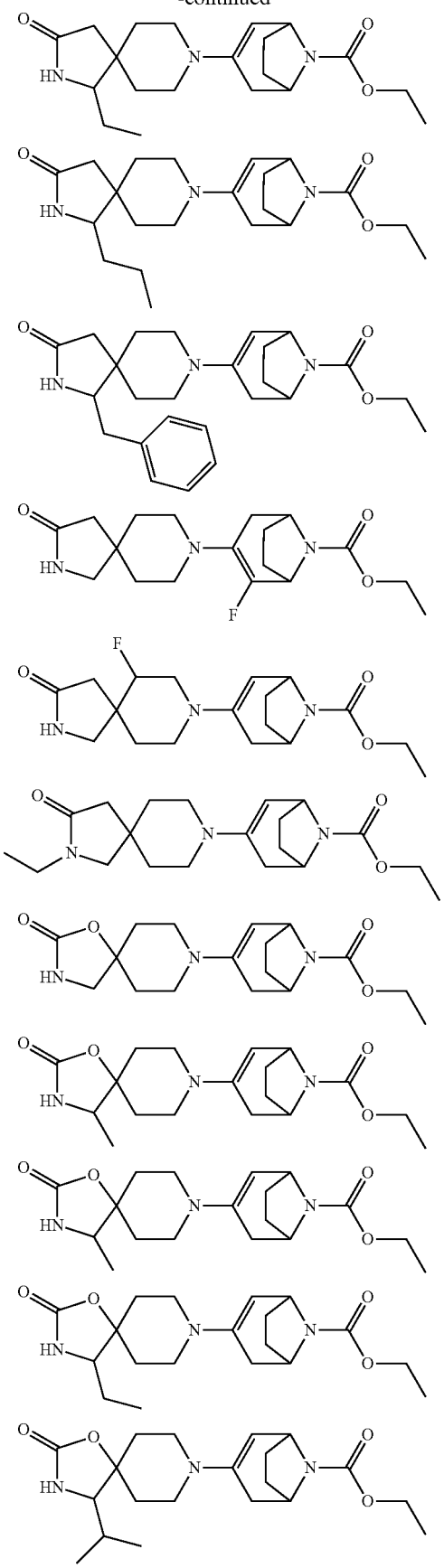
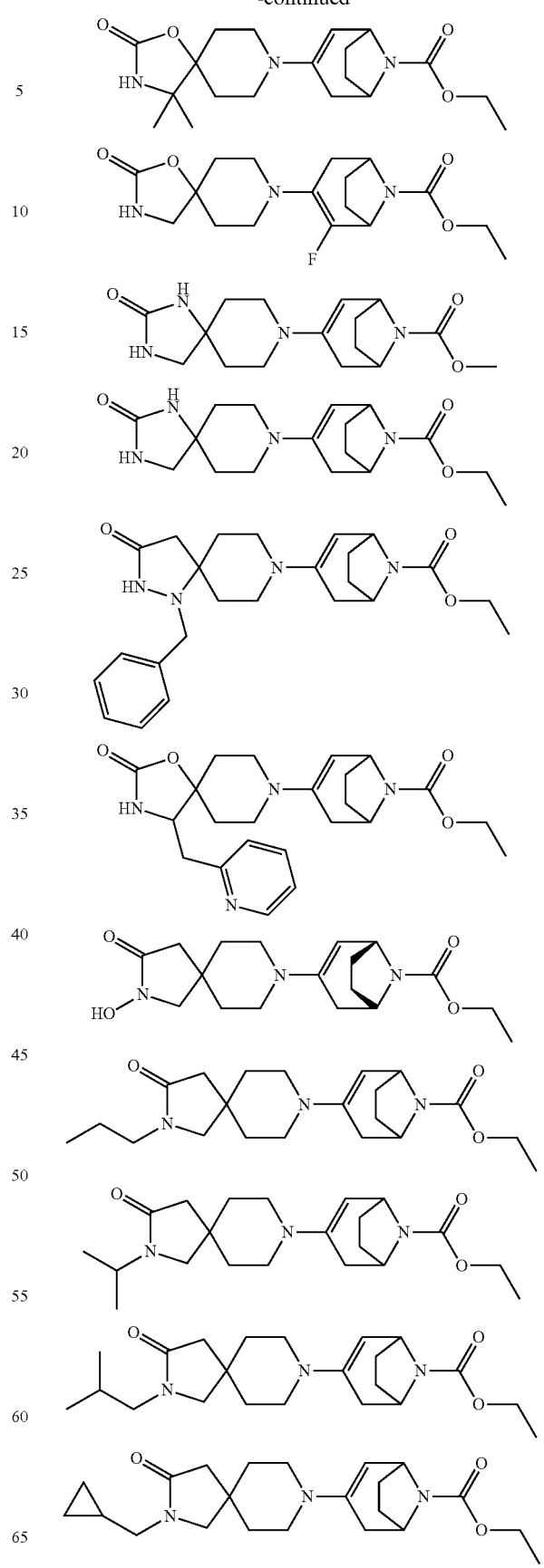

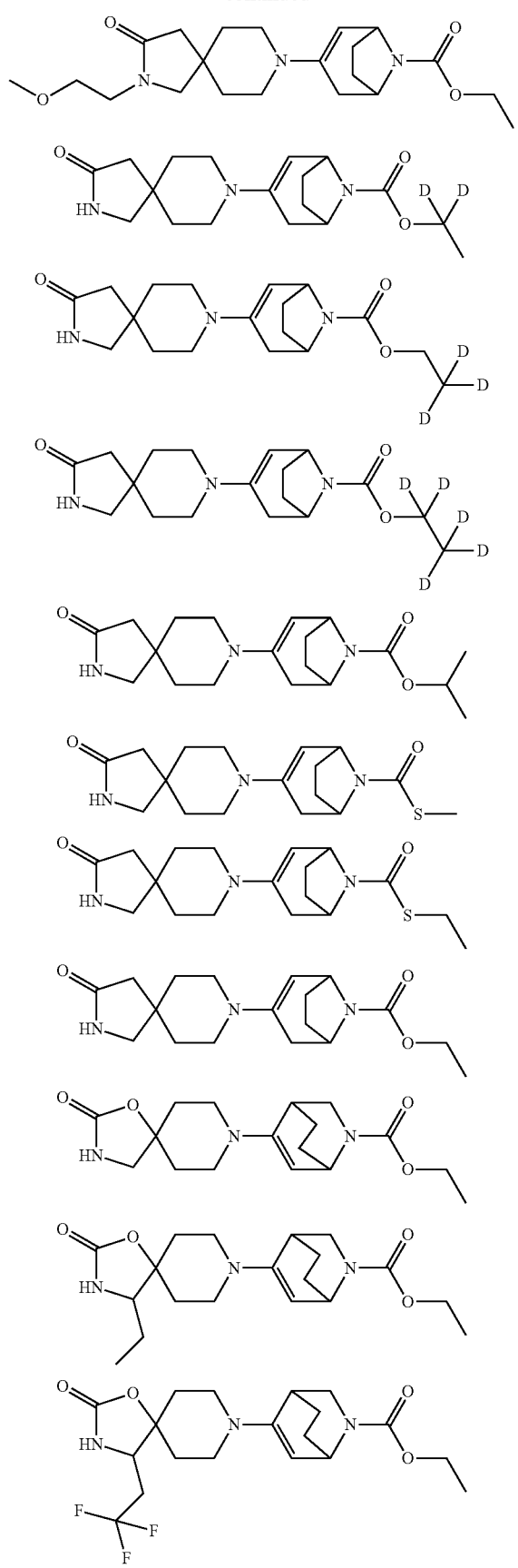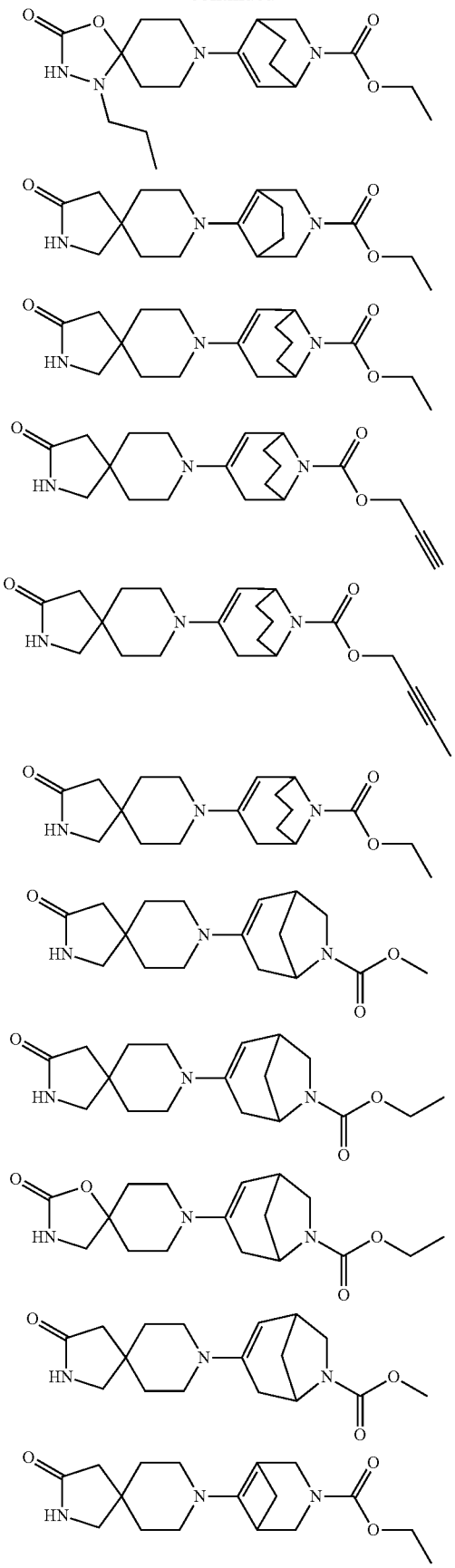

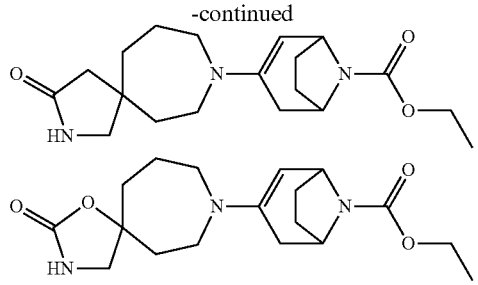
Example Embodiment 17: The isolated compound of Example Embodiment 1, which is selected from the following compounds
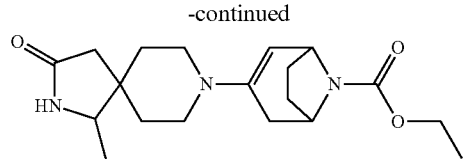
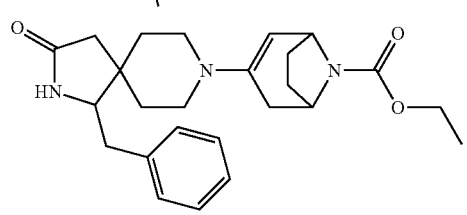
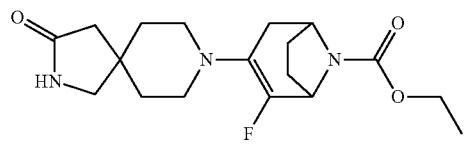
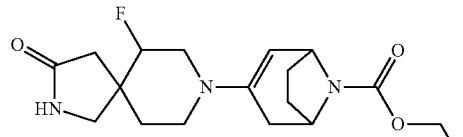
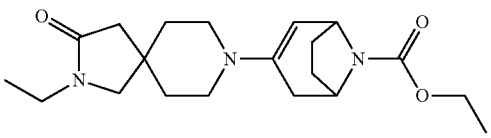
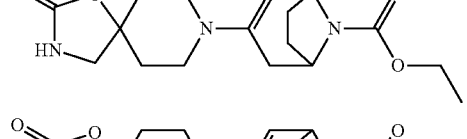
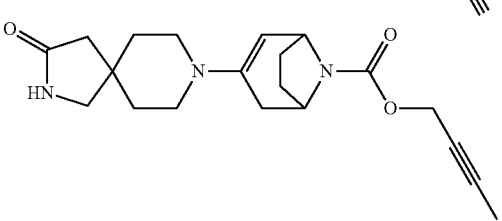
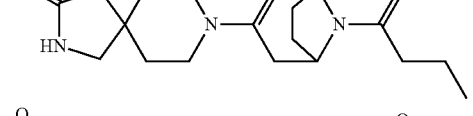
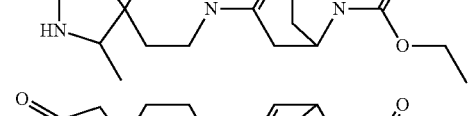
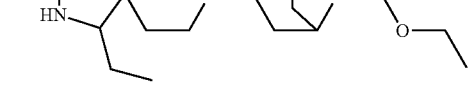
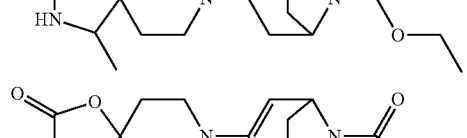
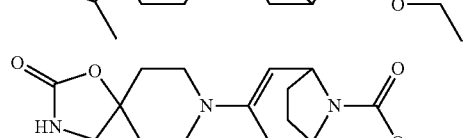
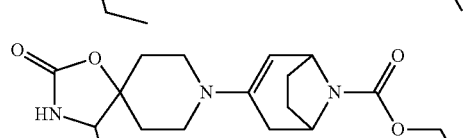
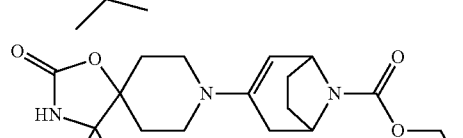

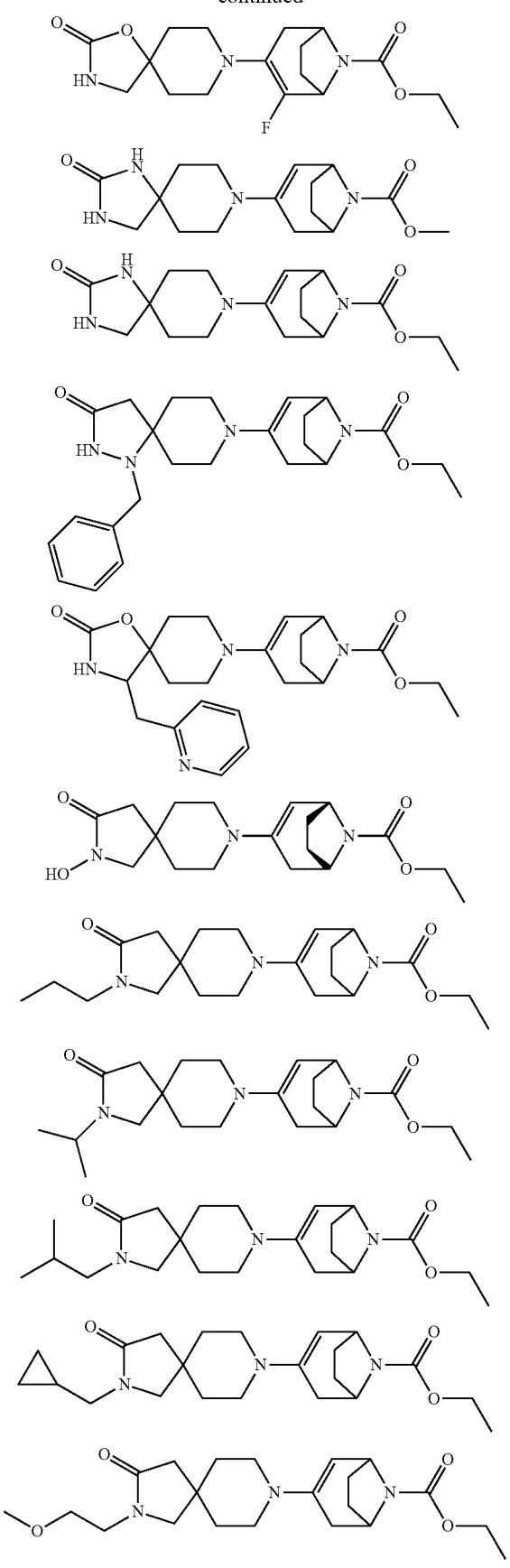
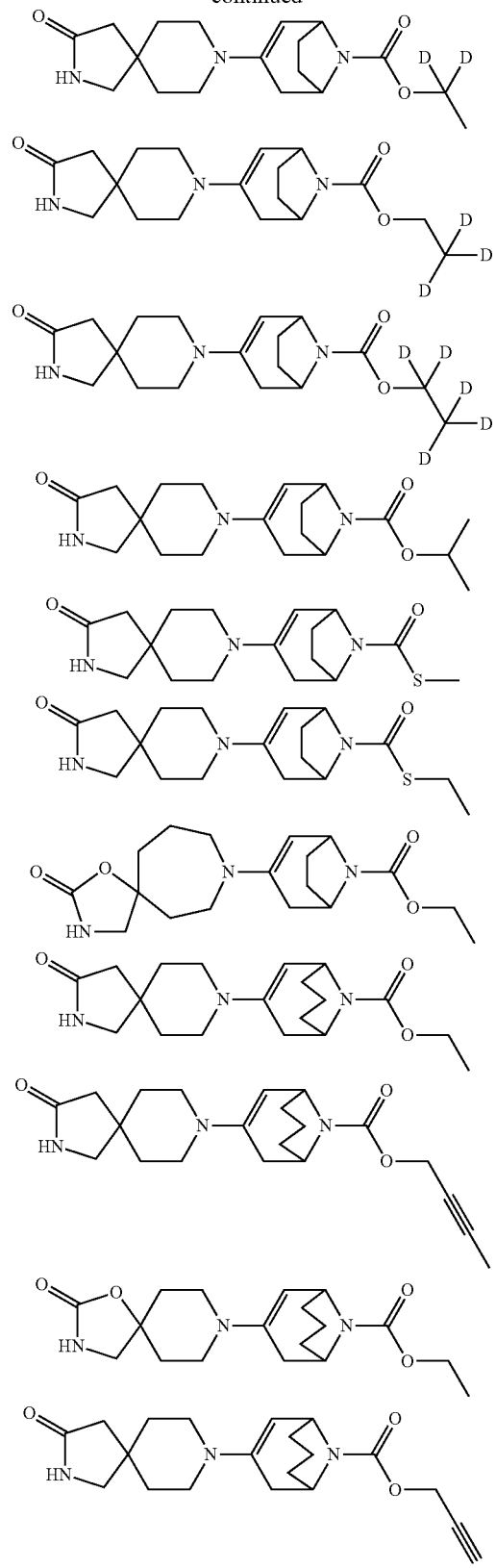
Example Embodiment 18: The isolated compound of Example Embodiment 1, which is selected from the following compounds

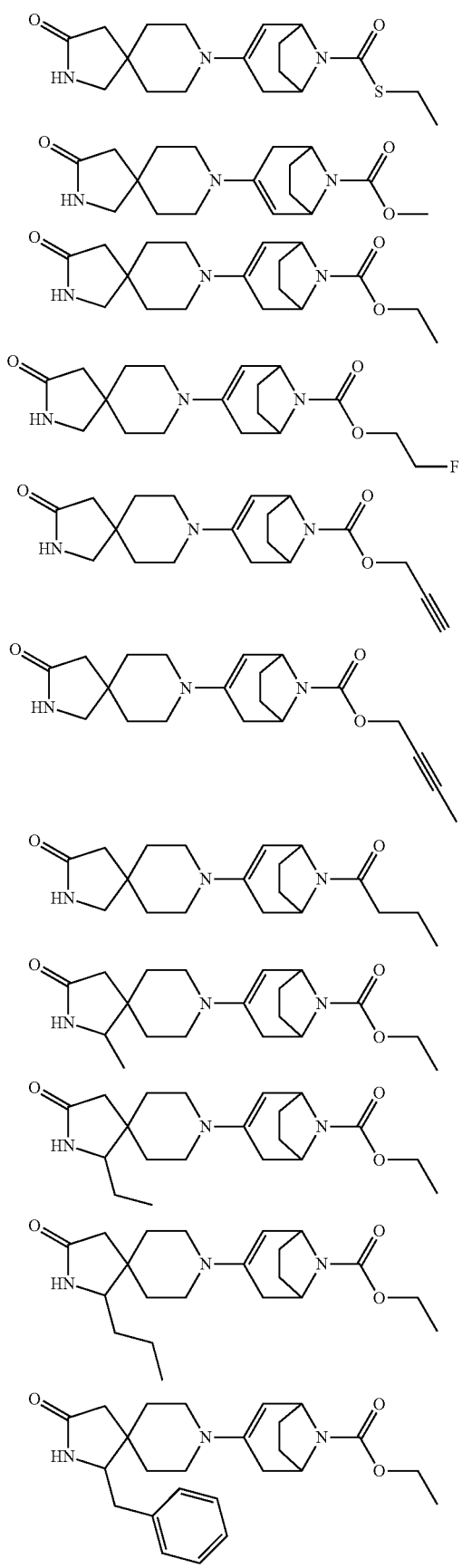
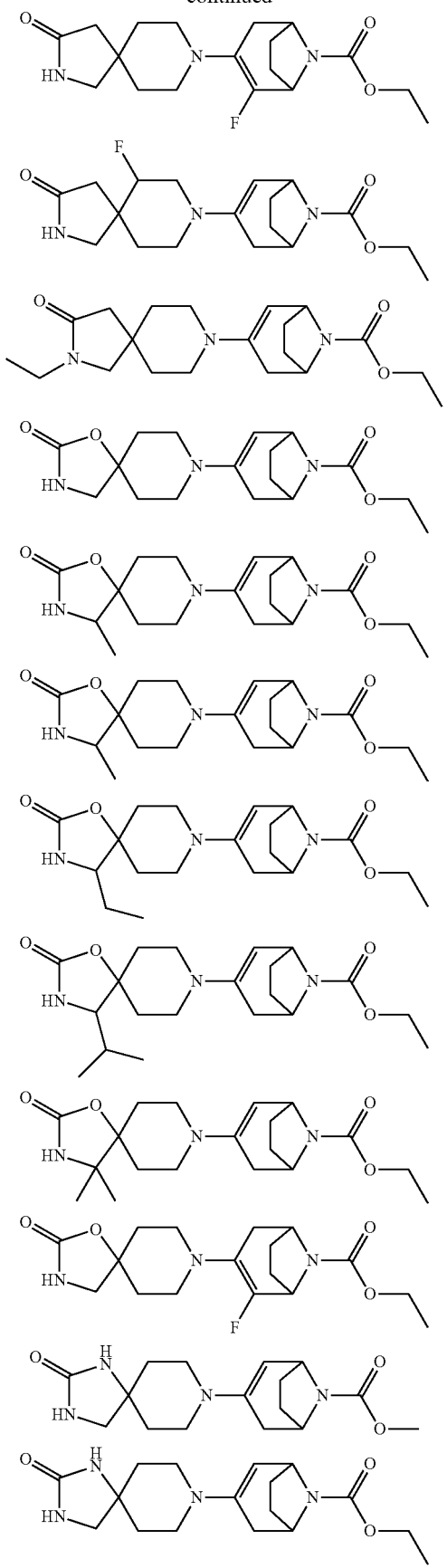

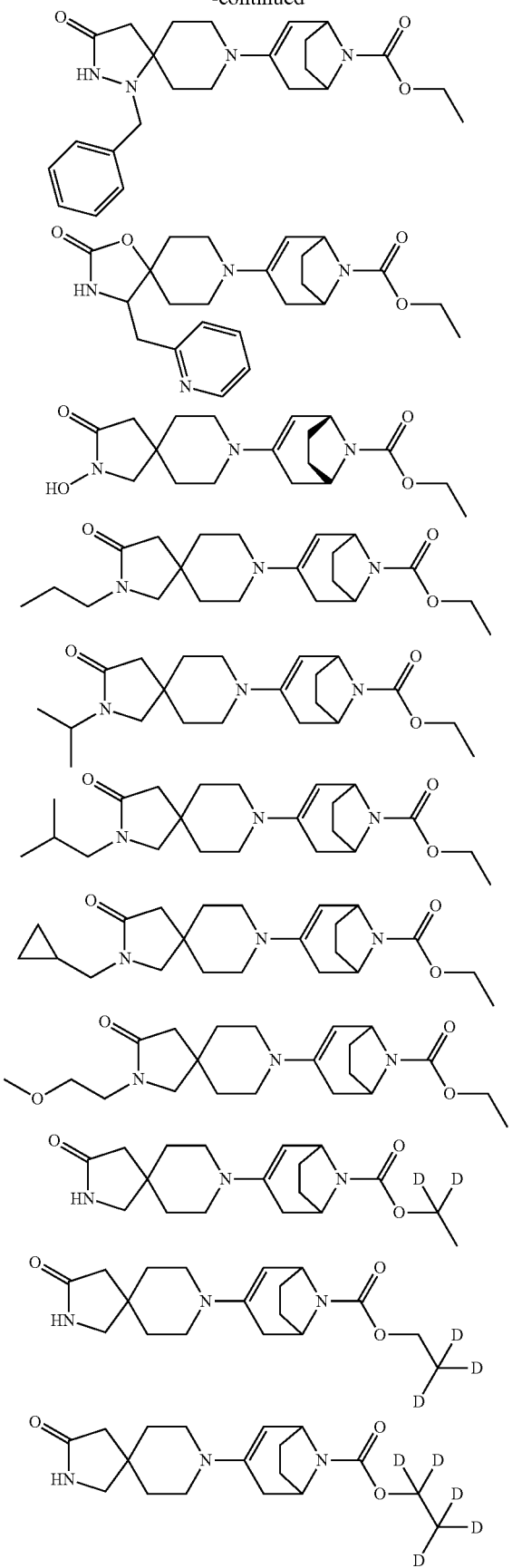

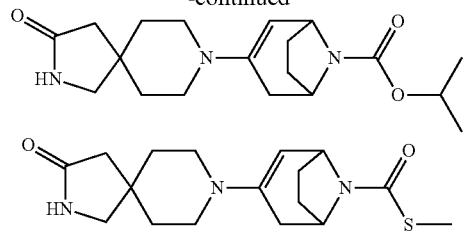

Example Embodiment 19: A method of synthesizing a compound of Formula B or a salt thereof,

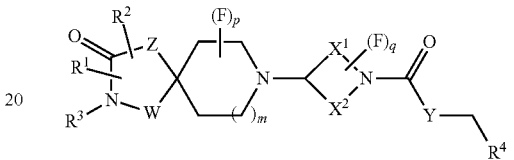

Formula B comprising:
contacting an isolated compound of Formula A with a reducing agent in an aprotic polar or non-polar solvent optionally comprising an acid,

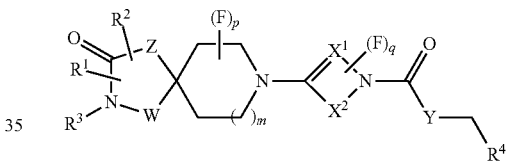

Formula A and, optionally, purifying the compound of Formula B, wherein:
m is 1 or 2;
p is 0, 1, or 2;
q is 0, 1, or 2;
W is C or N;
Z is $CH_2$, N, O, or S;
Y is NH, O, S, or $CH_2$;
$X^1$ and $X^2$ are hydrocarbons which together contain a total of five to nine carbon atoms and which link together such that the moiety

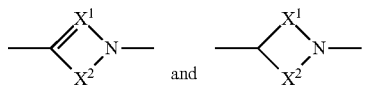

form a bridged bicyclic ring system;
$R^1$ and $R^2$ are independently H, halo, CN, OH, $C_{2-6}$ alkenyl, $C_{2-6}$ alkynyl, $C_{1-6}$ alkyl, $C_{1-6}$ haloalkyl, $C_{1-3}$ alkoxy, $NR^5R^6$, $C_{3-6}$ cycloalkyl, $C_{3-6}$ cycloalkenyl, $NR^5R^6$, $COOR^5$, $CONR^5R^6$, $NR^7CONR^5R^6$, $NR^7COOR^5$, $OCONR^5R^6$, $SR^5$, $SOR^5$, $SO_2R^5$, or $C_{1-6}$ alkylene-E;
$R^3$ is H, OH, $C_{1-6}$ alkyl, $C_{1-6}$ haloalkyl, $C_{2-6}$ alkenyl, $C_{2-6}$ alkynyl, 3 to 6 membered cycloalkyl, heterocycloalkyl, aryl or heteroaryl, or $C_{1-6}$ alkylene-E;
or $R^1$ and $R^2$, or $R^3$ and $R^2$ together from a cycloalkyl or heterocycloalkyl each of which is optionally substituted with at least one group selected from OH, halo, CN, OH, $C_{1-6}$ alkyl, $C_{1-6}$ haloalkyl, $C_{1-3}$ alkoxy, and $NH_2$;

E is OH, $C_{1-3}$ alkoxy, $NR^5R^6$, $SR^5$, 3 to 6 membered cycloalkyl, heterocycloalkyl, aryl or heteroaryl;

$R^4$ is H, $C_{1-5}$ alkyl, $C_{2-5}$ alkenyl, $C_{2-5}$ alkynyl, $C_{3-6}$ cycloalkyl, or $C_{3-6}$ cycloalkenyl, each of the alkyl, alkenyl, alkynyl, cycloalkyl and cycloalkenyl is optionally substituted with at least one group selected from OH, halo, CN, $C_{1-3}$ alkoxy, and $NH_2$;

$R^5$, $R^6$, and $R^7$ are independently H or $C_{1-6}$ alkyl;

provided that when Z is O, $R^3$ is H.

Example Embodiment 20: The method of Example Embodiment 19, wherein the reducing agent is selected from boron hydrides and silicon hydrides.

Example Embodiment 21: The method of Example Embodiment 19 or 20, wherein the silicon hydride is selected from $Et_3SiH$, $HSiCl_3$, $HSiPh_3$, and $HSiPh(CH_3)_2$.

Example Embodiment 22: The method of Example Embodiment 21, wherein the silicon hydride is $Et_3SiH$.

Example Embodiment 23: The method of Example Embodiment 21, wherein the silicon hydride is $HSiCl_3$.

Example Embodiment 24: The method of Example Embodiment 21, wherein the silicon hydride is $HSiPh_3$.

Example Embodiment 25: The method of Example Embodiment 21, wherein the silicon hydride is $HSiPh(CH_3)_2$.

Example Embodiment 26: The method of Example Embodiment 19 or 20, wherein the boron hydride is selected from $NaBH_4$, $NaBH(OAc)_3$, $NBu_4BH_4$, $NaBH(OAc)_3$, $NaCNBH_3$, and $NMe_4BH(OAc)_3$.

Example Embodiment 27: The method of Example Embodiment 26, wherein the boron hydride is $NaBH_4$.

Example Embodiment 28: The method of Example Embodiment 26, wherein the boron hydride is $NaBH(OAc)_3$.

Example Embodiment 29: The method of Example Embodiment 26, wherein the boron hydride is $NBu_4BH_4$.

Example Embodiment 30: The method of Example Embodiment 26, wherein the boron hydride is $NaBH(OAc)_3$.

Example Embodiment 31: The method of Example Embodiment 26, wherein the boron hydride is $NaCNBH_3$.

Example Embodiment 32: The method of Example Embodiment 26, wherein the boron hydride is $NMe_4BH(OAc)_3$.

Example Embodiment 33: The method of any one of example embodiments 19-32, wherein the aprotic polar or non-polar solvent is selected from xylenes, toluene, alkanes, $CHCl_3$, $CH_2Cl_2$, methyl tert-butyl ether, acetonitrile, propionitrile, tetrahydrofuran, and 2-methyl tetrahydrofuran.

Example Embodiment 34: The method of any one of example embodiments 19-33, wherein the optional acid is a $C_1$ to $C_{10}$ carboxylic acid.

Example Embodiment 35: The method of Example Embodiment 34, wherein the $C_1$ to $C_{10}$ carboxylic acid is acetic acid or hexanoic acid.

Example Embodiment 36: The method of any one of example embodiments 19-35, wherein the compound of Formula B obtained before the optional purification has an exo:endo isomer ratio greater than or equal to 70:30, greater than or equal to 75:25, greater than or equal to 80:20, greater than or equal to 85:15, greater than or equal to 90:10, greater than or equal to 95:5, or greater than or equal to 99:1.

Example Embodiment 37: The method of any one of example embodiments 19-35, wherein the compound of Formula B obtained before the optional purification has an endo:exo isomer ratio greater than or equal to 70:30, greater than or equal to 75:25, greater than or equal to 80:20, greater than or equal to 85:15, greater than or equal to 90:10, greater than or equal to 95:5, or greater than or equal to 99:1.

Example Embodiment 38: The method of any one of example embodiments 19-37, wherein the compound of Formula B is further converted to a pharmaceutically acceptable salt.

Example Embodiment 39: The method of any one of example embodiments 19-38, wherein the method also comprises contacting at reflux a mixture of a ketone of Formula C, a secondary amine of Formula D or a salt thereof, and an acidic catalyst in a non-polar solvent to obtain the compound of Formula A:

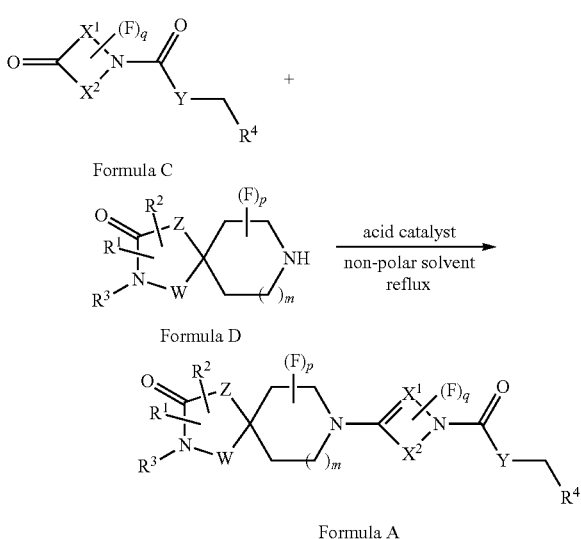

wherein $R^1$-$R^4$, Y, Z, W, m, p, and q are the same as described for Formula A, and $X^1$ and $X^2$ are hydrocarbons which together contain a total of five to nine carbon atoms and which link together such that the moiety:

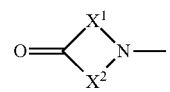

forms a bridged bicyclic ring system.

Example Embodiment 40: The method of Example Embodiment 39, the moiety

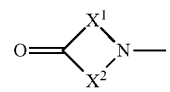

is selected from the following bridged bicyclic ring system wherein q is 0, 1, or 2:

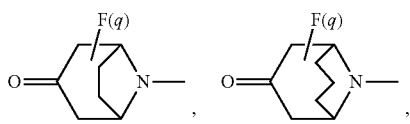

-continued
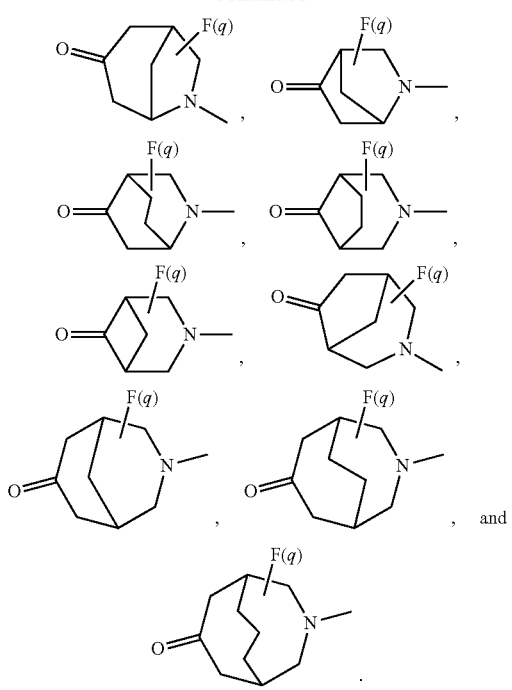
Example Embodiment 41: The method of any one of example embodiments 39-40, wherein the moiety
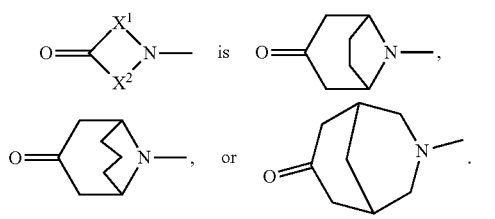
Example Embodiment 42: The method of any one of example embodiments 39-40, wherein the moiety
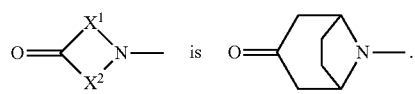
Example Embodiment 43: The method of Example Embodiment 39, wherein the ketone of formula C is selected from
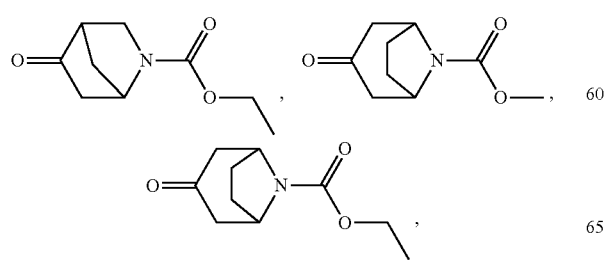
-continued
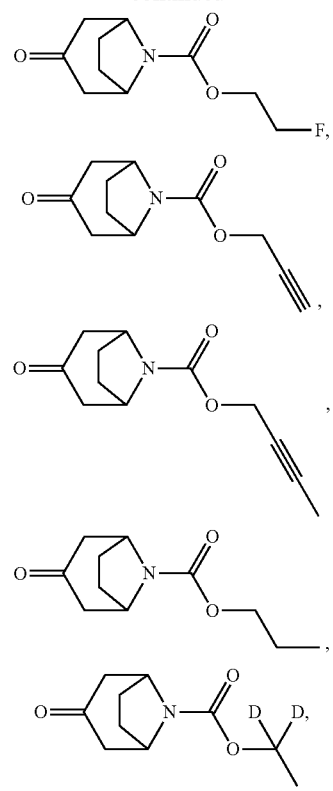

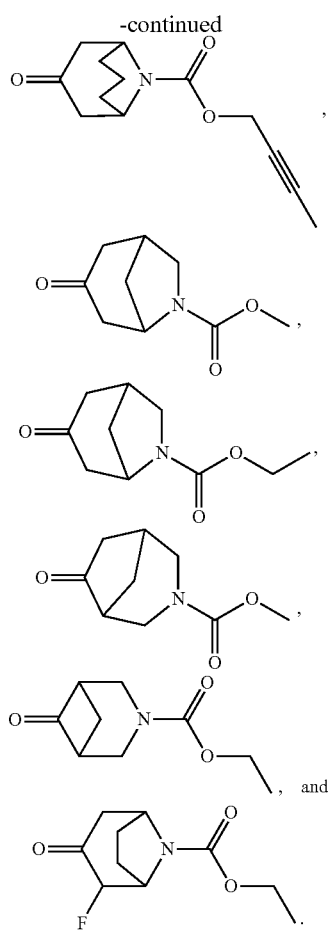
Example Embodiment 44: The method of Example Embodiment 39, wherein the secondary amine of Formula D is selected from
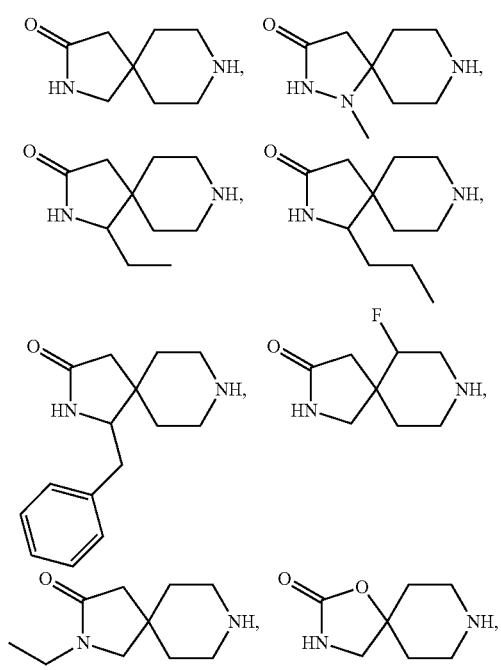
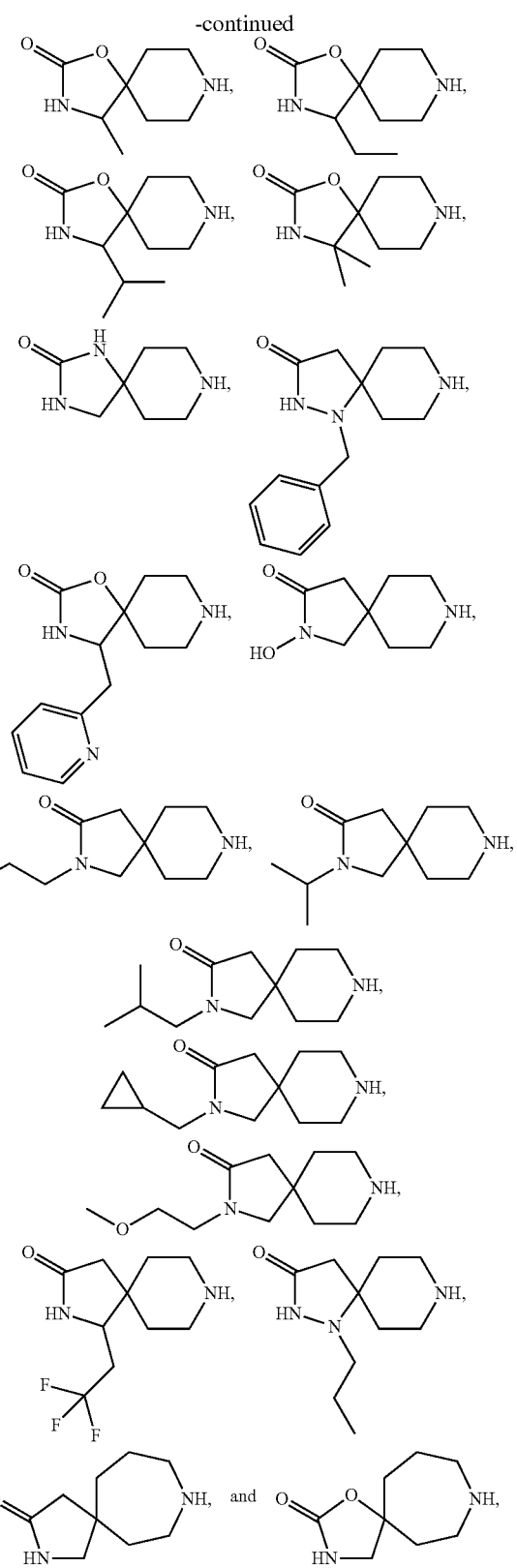
or a salt thereof.
Example Embodiment 45: The method of any one of example embodiments 39-44, wherein the non-polar solvent is xylenes.

Example Embodiment 46: The method of any one of example embodiments 39-45, wherein the catalytic acid hexanoic acid.

Example Embodiment 47: The method of any one of example embodiments 39-46, wherein the water produced by the reaction between the ketone of Formula C and the amine of Formula D is removed using a sieve dryer or Dean-Stark apparatus.

Example Embodiment 48: The method of any one of example embodiments 39-47, wherein the compound of Formula A is isolated by crystallization.

Example Embodiment 49: The method of Example Embodiment 48, wherein the crystallization is accomplished by cooling the reaction mixture to room temperature, adding another non-polar solvent, optionally seeding the mixture with the previously formed compound of Formula A, and collecting the solid compound of Formula A.

Example Embodiment 50: The method of Example Embodiment 49, wherein the another non-polar solvent is hexane, heptane, or octane.

Example Embodiment 51: The isolated compound of any one of example embodiments 1-18, which is:

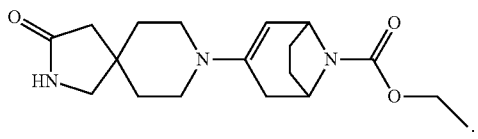 [SMILES: CCOC(=O)N1C2C=C(N3CCC4(CC3)CNC(=O)C4)CC1CC2]

Example Embodiment 52: The method of any one of example embodiments 19-50, wherein the compound of Formula B is:

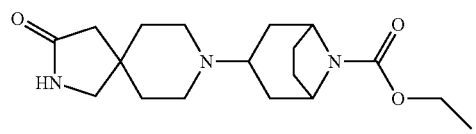

or a salt thereof, and wherein the compound of Formula A is:

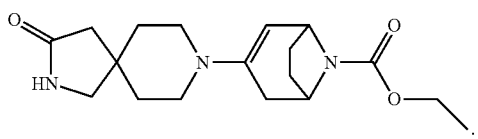 [SMILES: CCOC(=O)N1C2C=C(N3CCC4(CC3)CNC(=O)C4)CC1CC2]

Example Embodiment 53: A compound of Formula A:

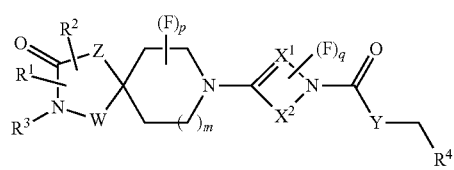

Formula A substantially as described herein.

Example Embodiment 54: An isolated compound of Formula A:

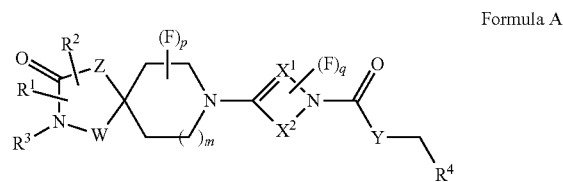

Formula A substantially as described herein.

Example Embodiment 55: A diastereo-selective reduction of a compound of Formula A:

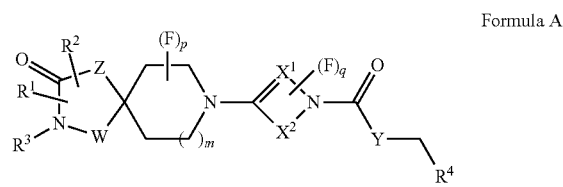

Formula A into a compound of Formula B:

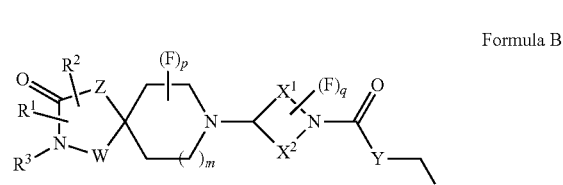

Formula B substantially as described herein.

Example Embodiment 56: A method of synthesizing a compound of Formula B:

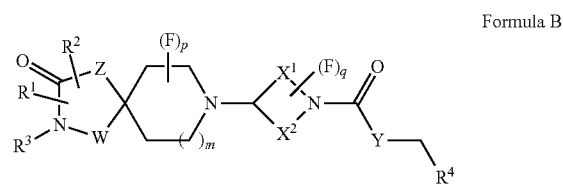

Formula B substantially as described herein.

BRIEF DESCRIPTION OF THE DRAWINGS

FIG. 1 shows an illustration of the "endo" and "exo" isomers of compounds of Formula B as used herein. In particular, Panel A shows the "endo" isomer, and Panel B shows the "exo" isomer.

DETAILED DESCRIPTION

Definitions

The terms "alkoxy", "alkyl", "alkenyl", "alkylene", "alkynyl", "aryl", "cycloalkyl", "cycloalkenyl", "heteroaryl", and "heterocycloalkyl" are used in their conventional sense (e.g. as defined in the IUPAC Gold Book) unless indicated otherwise.

The term "cycloalkyl" as used herein, where the specified number of carbon atoms permits, includes both monocyclic cycloalkyl groups such as cyclopropyl, cyclobutyl, cyclopentyl, cyclohexyl and cycloheptyl, and bicyclic and tricyclic groups. Bicyclic cycloalkyl groups include bridged ring systems such as bicycloheptane, bicyclooctane and adamantane.

"Haloalkyl" as used herein refers to an alkyl substituted with one or more halo atoms selected from F, Cl, Br, and I.

The term "isolated" as used herein means that a compound is substantially free of solvent. "Substantially free of solvent" means that the solvent is less than 15% by weight, such as less than 10% by weight, further such as less than 5% by weight, of the total weight of the obtained mass (including target compound, solvent, etc). In some embodiments, "isolated" means that a compound is substantially free of solvent and impurities. "Substantially free of solvent and impurities" means that the solvent and impurities together is less than 15% by weight, such as less than 10% by weight, further such as less than 5% by weight, of the total weight of the obtained mass (including the target compound, solvent, impurities, etc.). In some embodiments, "isolated" means that a compound is characterized by an analytical instrument, such as NMR, mass spectrometry, chromatography (e.g. HPLC, GC, GC-MS, LC-MS, etc.) and others identifiable to a skilled person upon reading the present disclosure.

The term "contacting" as used herein refers to bringing two or more substances (e.g. compounds) into sufficiently close proximity such that chemical reaction of the molecules of the two substances can occur. In some embodiments, a first substance is contacted with a second substance by dissolving and/or suspending the first substance in a solvent (e.g. a liquid solvent) and either i) adding the second substance (e.g. neat or in a solvent such as a liquid solvent) to the solution or suspension of the first substance, or ii) adding the solution or suspension of the first substance to the second substance (which itself could be dissolved and/or suspended in a solvent) thereby allowing the molecules of the two substances to react. In some embodiments, the first substance is an isolated enamine (or salt thereof) as described herein. In some embodiments, when the first substance is an isolated enamine, it can be contacted with a second substance (e.g. a reducing agent to reduce the enamine to an amine) by dissolving and/or suspending the isolated enamine in a solvent (e.g. an aprotic polar or non-polar solvent), and either i) adding the second substance (e.g. neat or in a solvent such as a liquid solvent) to the resulting solution or suspension of the isolated enamine, or ii) adding the resulting solution or suspension of the enamine to the second substance (which itself could be dissolved and/or suspended in a solvent) thereby allowing the molecules of the two substances to react. In such a situation, the isolated enamine would be understood to be "contacted" with the second substance even though the isolated enamine was dissolved and/or suspended in a solvent at the time of contact with the second substance.

As used herein, the term "diastereo-selective" or "diastereo-selectivity" refers to the reduction of compounds, which produces more of one stereoisomer than the other (e.g. more exo isomer than endo isomer, or more endo isomer than exo isomer). Endo isomer as used herein refers to a compound of formula B wherein the bond connecting the spiro cyclic amine to the moiety

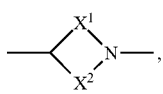

and the bridge of the moiety

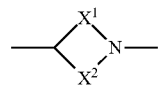

have the same orientation, whereas in the exo isomer, the bond connecting the spiro cyclic amine to the moiety

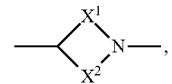

and the bridge of the moiety

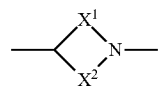

have the opposite orientation, as illustrated in FIG. 1.

The compounds as disclosed herein may contain one or more isotopic substitutions, and a reference to a particular element includes within its scope all isotopes of the element. For example, a reference to hydrogen includes within its scope $^{1}H$, $^{2}H$ (D), and $^{3}H$ (T). Similarly, references to carbon and oxygen include within their scope respectively $^{12}C$, $^{13}C$ and $^{14}C$ and $^{16}O$ and $^{18}O$.

In some embodiments, the compounds described herein can contain asymmetric and/or chiral centers and/or other sources of stereochemistry, and, therefore, can exist in different stereoisomeric forms (e.g. enantiomers, diastereomers, atropisomers, and others identifiable to a skilled person upon a reading of the present disclosure). Individual stereoisomers of the compounds of the invention can, for example, be substantially free of other isomers, or can be admixed, for example, as racemates or with all other, or other selected, stereoisomers. Unless otherwise indicated, the compounds disclosed in the present specification include the individual isomers of compounds that form more than one type of isomerism, or mixtures of one or more of the isomers. In particular, reference to a compound or compounds described herein is intended to encompass that compound in each of its possible stereoisomeric forms and mixtures thereof unless the particular isomeric form is referred to specifically.

The compounds disclosed in the present specification may be present in the form of a pharmaceutically acceptable salt. As used herein, the term "a pharmaceutically acceptable salt" refers to non-toxic acidic/anionic or basic/cationic salt forms of the compounds disclosed in the present specification. Suitable pharmaceutically acceptable salts include acid addition salts which may, e.g., be formed by mixing a solution of the compound disclosed in the present specification with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid.

Furthermore, when the compounds disclosed in the present specification carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, without limitation, acetate, aspirate, benzenesulfonate, benzoate, besylate, bicarbonate, bisulfate, bitartrate, borate, bromide, calcium, camsylate (or camphorsulphonate), carbonate, chloride, citrate, clavulanate, dihydrochloride, edetate, edisylate, esylate, formate, fumarate, gluceptate, gluconate, glucuronate, glutamate, hexafluorophosphate, hibenzate, hydrabamine, hydrobromide, hydrobromine, hydrochloride, hydroiodide, iodide, isethionate, isothionate, lactate, malate, maleate, malonate, mandelate, mesylate, methylsulfate, nitrate, naphthylate, 2-napsylate, nicotinate, nitrate, oleate, orotate, oxalate, pamoate, palmitate, phosphate/diphosphate/hydrogen phosphate, saccharate, salicylate, stearate, sulfate, succinate, tartrate, tosylate and trifluoroacetate. (see, e.g., *Handbook of Pharmaceutical Salts*, P. Heinrich Stahl & Camille G. Wermuth (Eds), Verlag; *Helvetica Chimica Acta*-Zürich, 2002, 329-345; and Berge et al., *Journal of Pharmaceutical Science*, 1977, 66:1-19).

Compounds

In some embodiments, a compound which can be useful as an intermediate in the syntheses of muscarinic receptor agonists as disclosed in PCT/GB2015/050807 is disclosed.

In some embodiments, the compound is an isolated compound of Formula A:

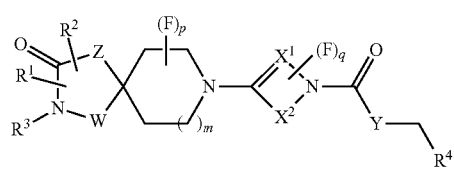

Formula A or a salt thereof, wherein:
m is 1 or 2;
is 0, 1, or 2;
q is 0, 1, or 2;
W is C or N;
Z is $CH_2$, N, O, or S;
Y is NH, O, S, or $CH_2$;
$X^1$ and $X^2$ are hydrocarbons which together contain a total of five to nine carbon atoms and which link together such that the moiety:

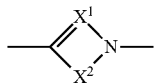

forms a bridged bicyclic ring system;
$R^1$ and $R^2$ are independently H, halo, CN, OH, $C_{2-6}$ alkenyl, $C_{2-6}$ alkynyl, $C_{1-6}$ alkyl, $C_{1-6}$ haloalkyl, $C_{1-3}$ alkoxy, $NR^5R^6$, $C_{3-6}$ cycloalkyl, $C_{3-6}$ cycloalkenyl, $NR^5R^6$, $COOR^5$, $CONR^5R^6$, $NR^7CONR^5R^6$, $NR^7COOR^5$, $OCONR^5R^6$, $SR^5$, $SOR^5$, $SO_2R^5$, or $C_{1-6}$ alkylene-E;
$R^3$ is H, OH, $C_{1-6}$ alkyl, $C_{1-6}$ haloalkyl, $C_{2-6}$ alkenyl, $C_{2-6}$ alkynyl, 3 to 6 membered cycloalkyl, heterocycloalkyl, aryl or heteroaryl, or $C_{1-6}$ alkylene-E;
or $R^1$ and $R^2$, or $R^3$ and $R^2$ together from a cycloalkyl or heterocycloalkyl each of which is optionally substituted with at least one group selected from OH, halo, CN, OH, $C_{1-6}$ alkyl, $C_{1-6}$ haloalkyl, $C_{1-3}$ alkoxy, and $NH_2$;

E is OH, $C_{1-3}$ alkoxy, $NR^5R^6$, $SR^5$, 3 to 6 membered cycloalkyl, heterocycloalkyl, aryl or heteroaryl;
$R^4$ is H, $C_{1-5}$ alkyl, $C_{2-5}$ alkenyl, $C_{2-5}$ alkynyl, $C_{3-6}$ cycloalkyl, or $C_{3-6}$ cycloalkenyl, each of the alkyl, alkenyl, alkynyl, cycloalkyl and cycloalkenyl is optionally substituted with at least one group selected from OH, halo, CN, $C_{1-3}$ alkoxy, and $NH_2$;
$R^5$, $R^6$, and $R^7$ are independently H or $C_{1-6}$ alkyl;
provided that when Z is O, $R^3$ is H.

In some embodiments, $R^1$ is H, halo, CN, OH, $C_{1-4}$ alkyl, $C_{1-6}$ haloalkyl, $C_{1-3}$ alkoxy, $NH_2$, or $C_{1-6}$ alkylene-E, wherein E is $C_{1-3}$ alkoxy, 5 or 6 membered cycloalkyl, heterocycloalkyl, aryl, or heteroaryl. In some embodiments, $R^1$ is H, halo, CN, OH, $C_{1-4}$ alkyl, $C_{1-6}$ haloalkyl, $C_{1-3}$ alkoxy, $NH_2$, or $C_{1-2}$ alkylene-E, wherein E is methoxy, cyclopropyl, phenyl, or pyridinyl.

In some embodiment, $R^2$ is H, methyl, ethyl, propyl, isopropyl, or benzyl.

In some embodiment, $R^3$ is H, OH, $C_{1-6}$ alkyl, $C_{1-6}$ haloalkyl, $C_{2-6}$ alkenyl, $C_{2-6}$ alkynyl, $C_{3-6}$ cycloalkyl, 5 or 6 membered aryl or heteroaryl, or $C_{1-6}$ alkylene-E, wherein E is OH, $C_{1-3}$ alkoxy, $NR^5R^6$, $SR^5$, $C_{3-6}$ cycloalkyl, 5 or 6 membered aryl or heteroaryl.

In some embodiments, $R^4$ is H, $C_{1-5}$ alkyl, $C_{2-5}$ alkenyl, or $C_{2-5}$ alkynyl.

In some embodiments, p is 0 and q is 0.
In some embodiments, Z is $CH_2$, N, or O.
In some embodiments, Z is $CH_2$.
In some embodiments, the moiety

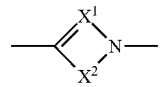

is an azabicyclo-heptene, azabicyclo-octene, or azabicyclo-nonene ring system.

In some embodiments, the moiety

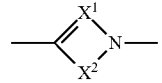

is selected from the following ring system wherein q is 0, 1, or 2:

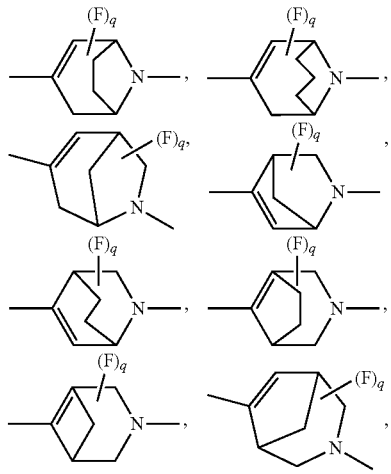

-continued

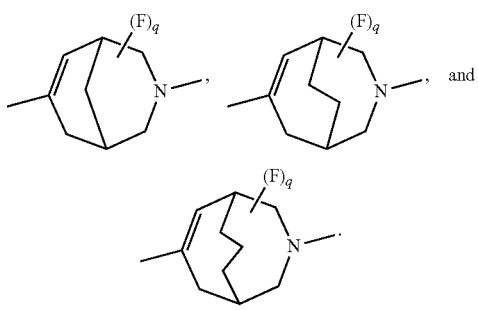

In some embodiments, the moiety

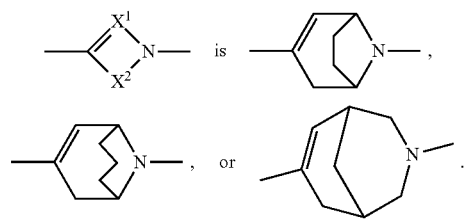

In some embodiments, the moiety

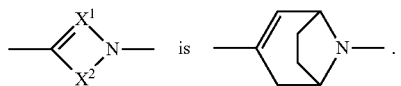

In some embodiments, $R^1$, $R^2$, and $R^3$ are independently H or $C_{1-3}$ alkyl, Z is $CH_2$, q is 0, and W is C.

In some embodiments, m is 1, Y is O, and $R^4$ is methyl, fluoromethyl, ethyl, ethynyl, 2-butynyl, and 1-propynyl.

In some embodiments, the isolated compound of Formula A is crystalline solid.

In some embodiments, the isolated compound is selected from the following compounds:

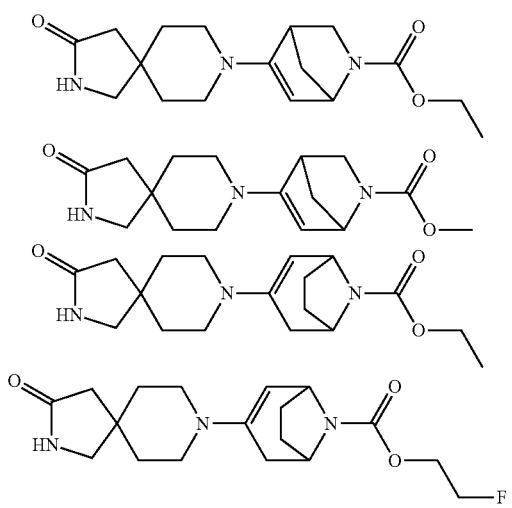

-continued

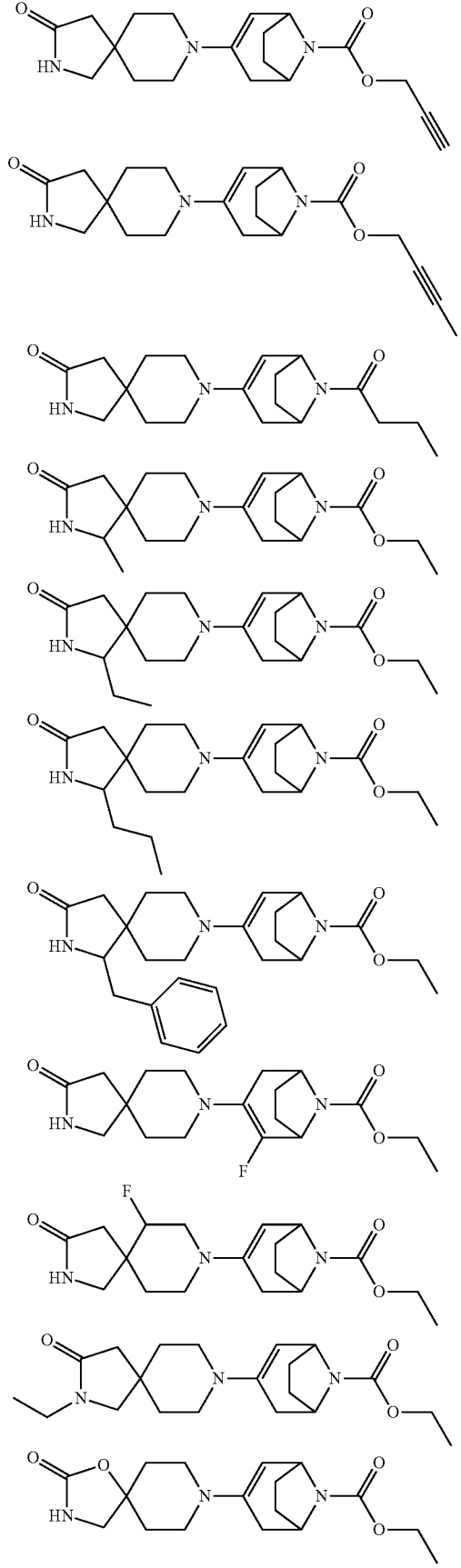

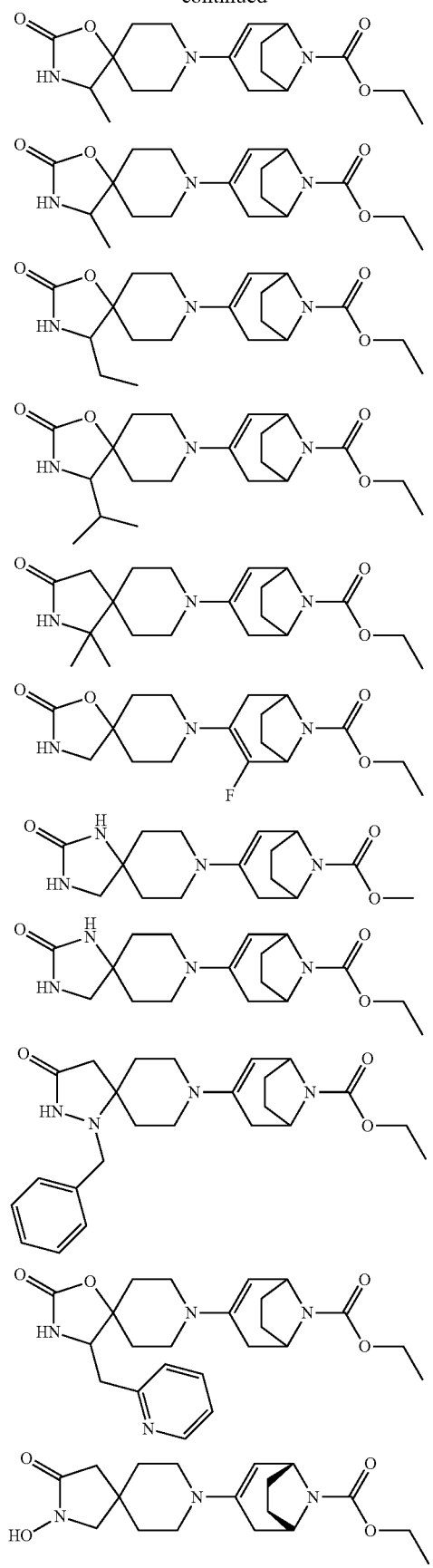
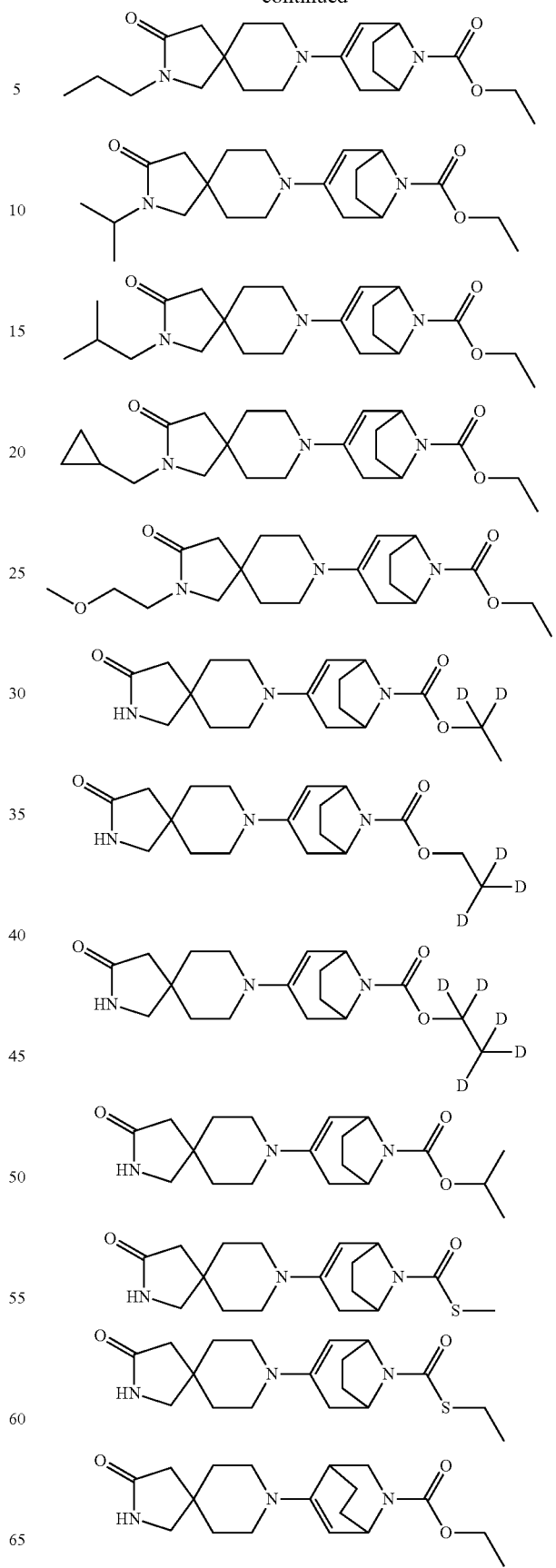

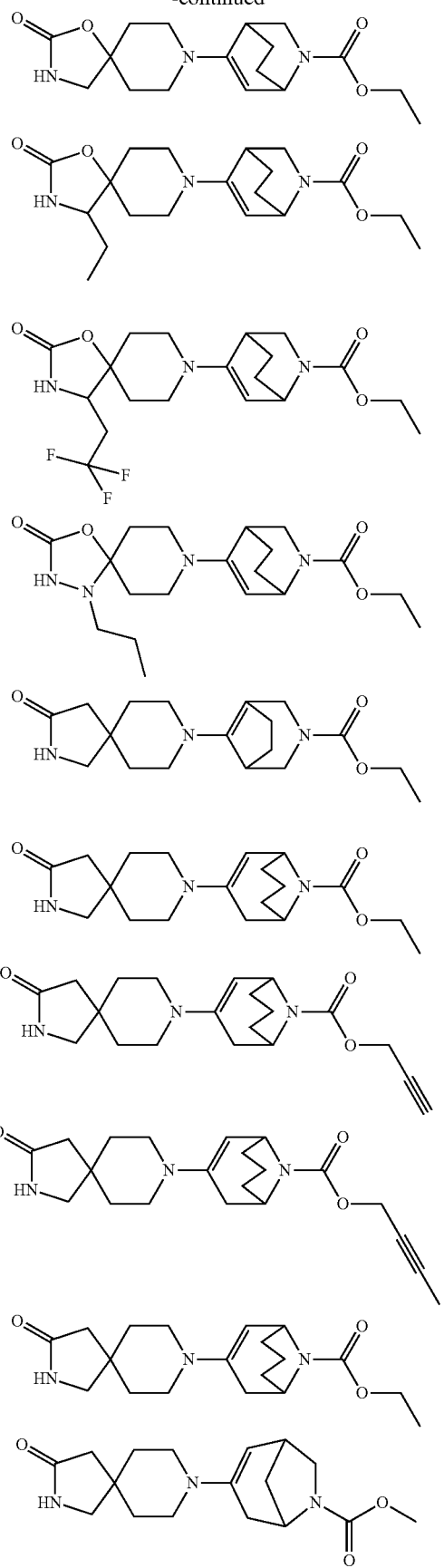
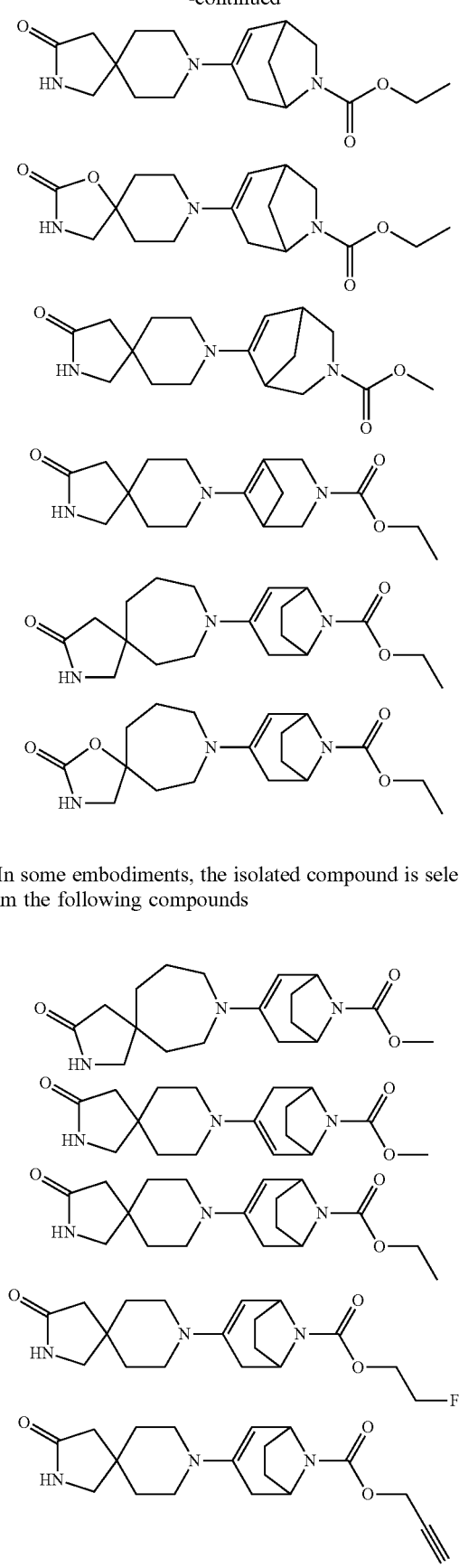
In some embodiments, the isolated compound is selected from the following compounds

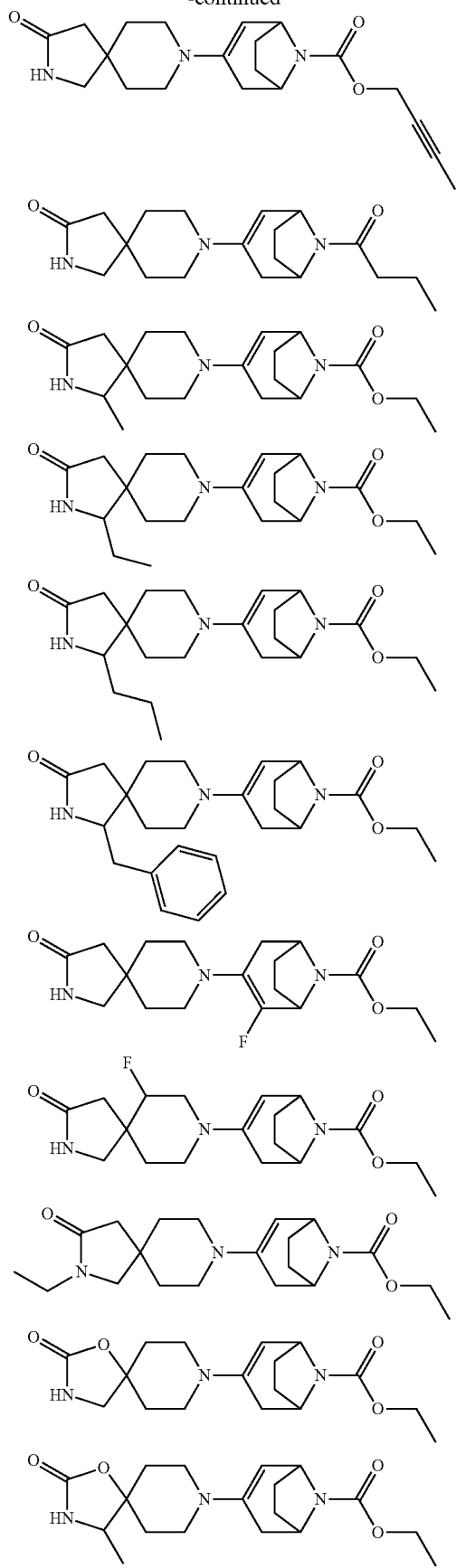
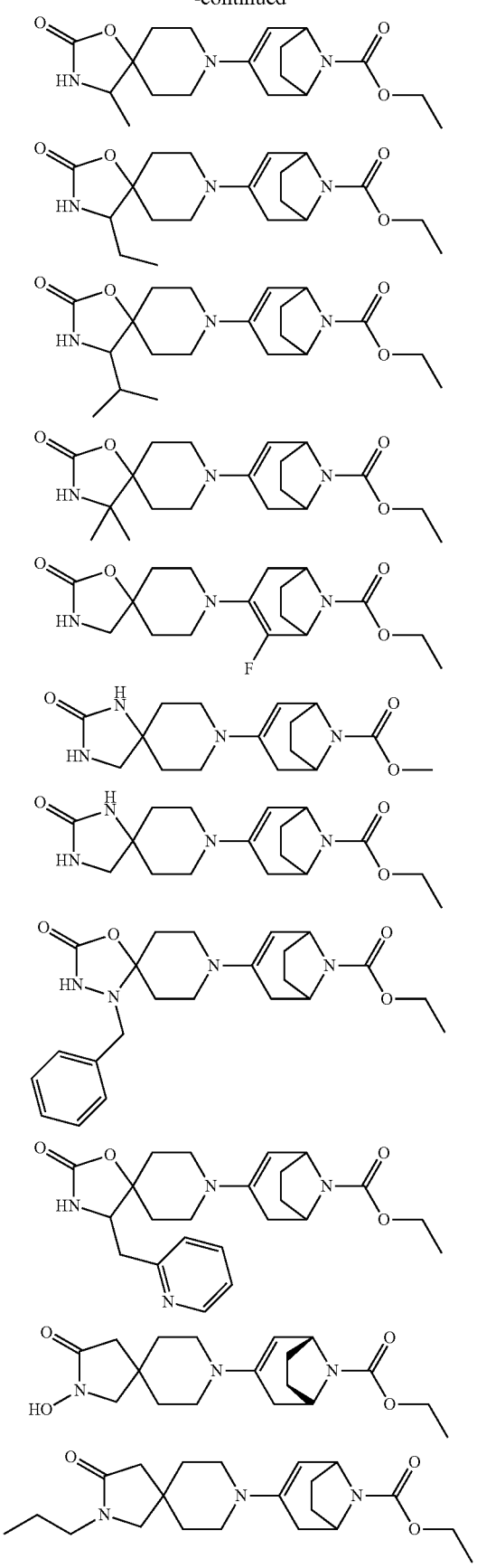

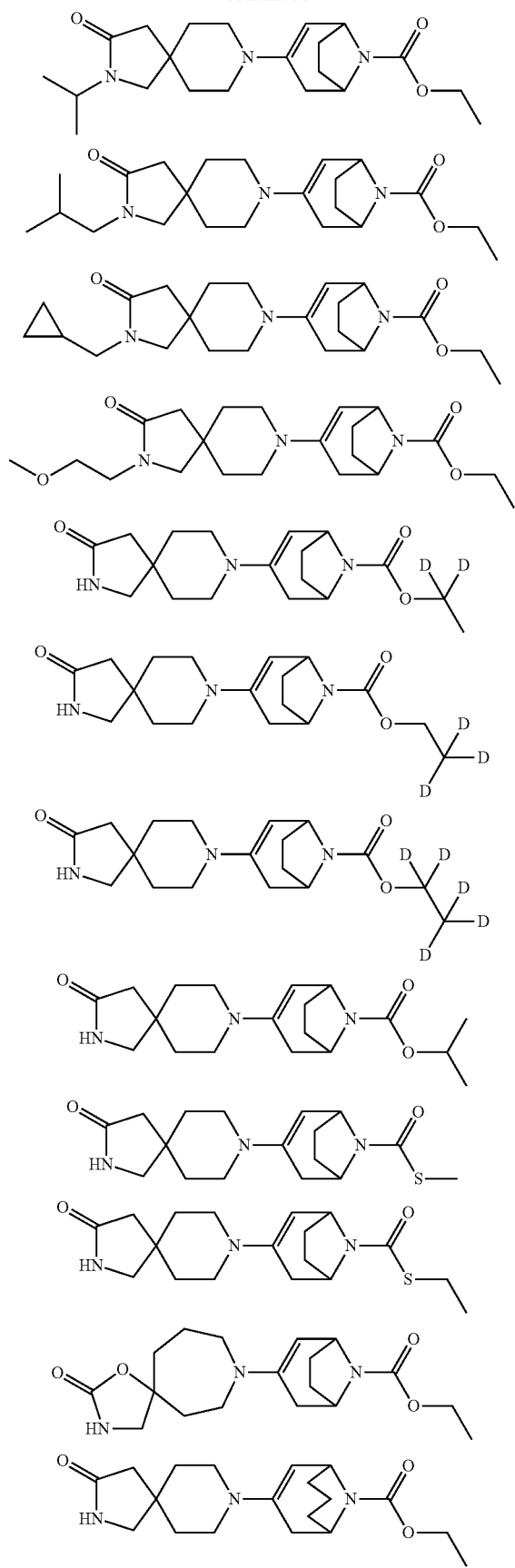
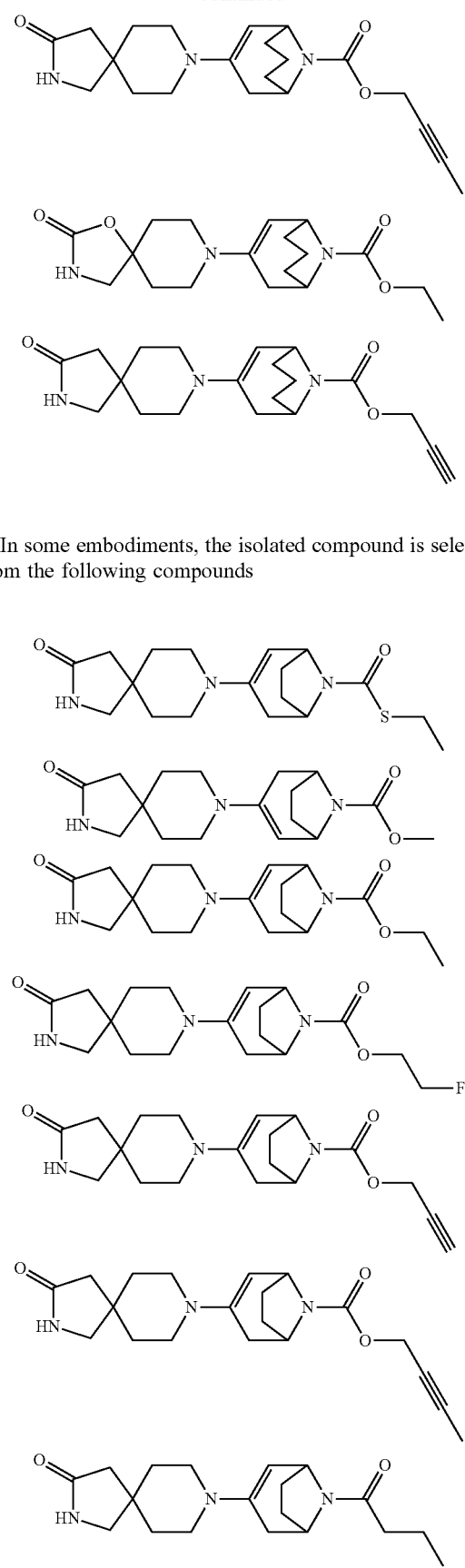
In some embodiments, the isolated compound is selected from the following compounds

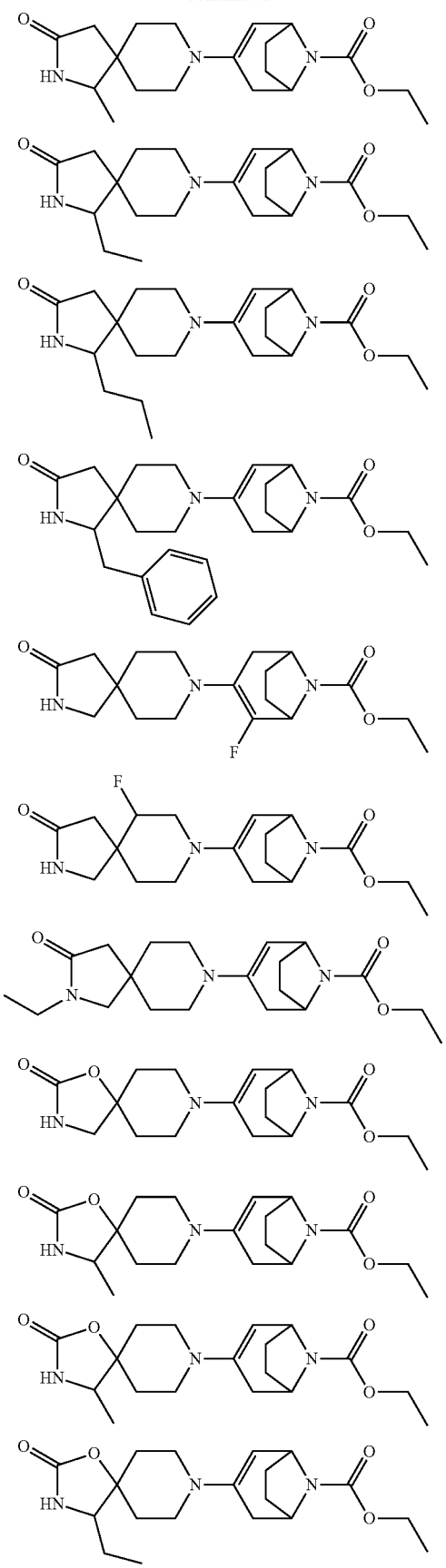
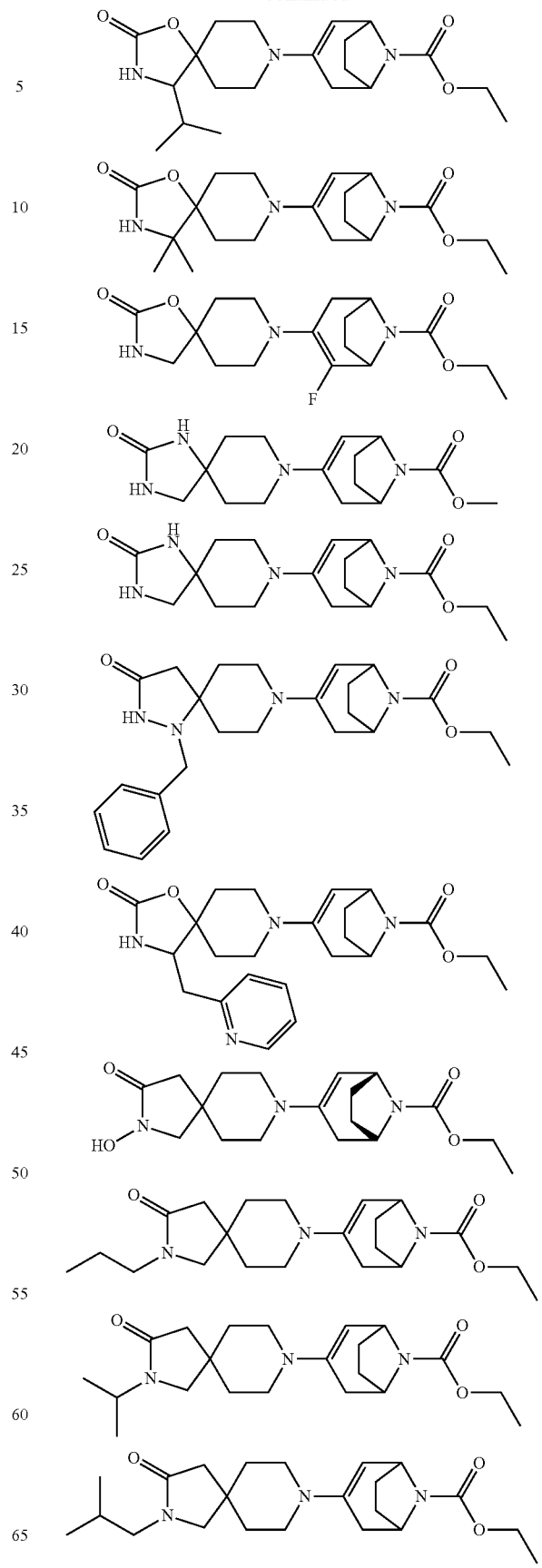

-continued

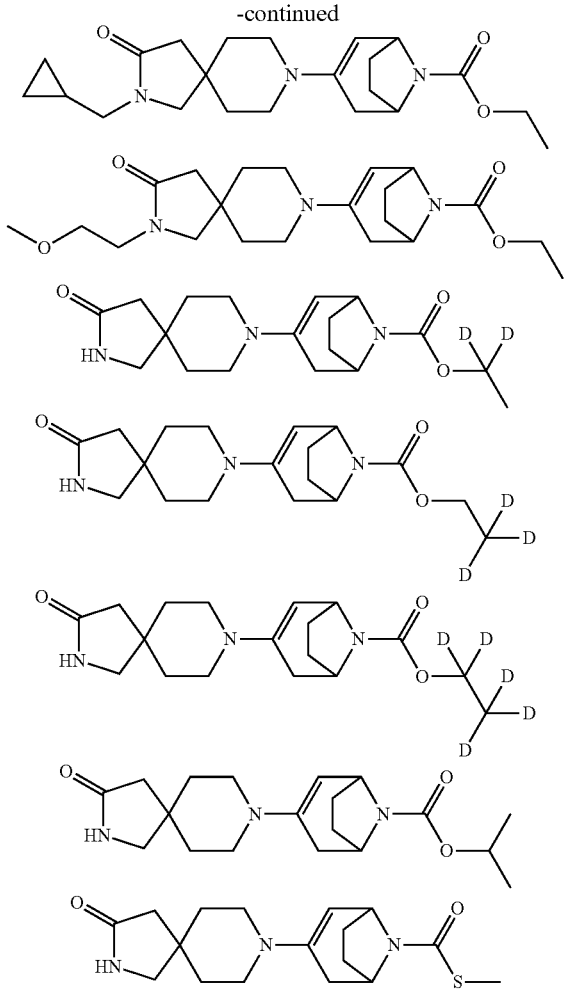

Method of Preparation

In some embodiments, a method of preparing a compound of Formula B or a salt thereof is disclosed,

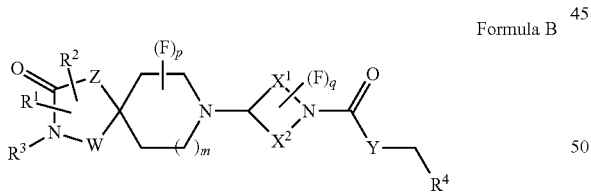

Formula B wherein $R^1$-$R^4$, Y, Z, W, m, p, and q are the same as described herein for Formula A, including each embodiment thereof, and $X^1$ and $X^2$ are hydrocarbons which together contain a total of five to nine carbon atoms and which link together such that the moiety:

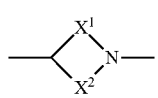

forms a bridged saturated bicyclic ring system. The method comprises contacting the isolated compound of Formula A with a reducing agent in an aprotic polar or non-polar solvent optionally comprising an acid:

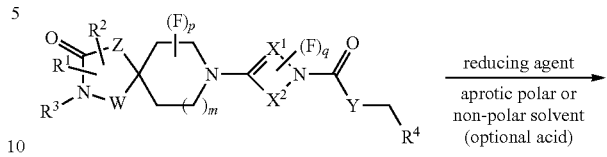

Formula A

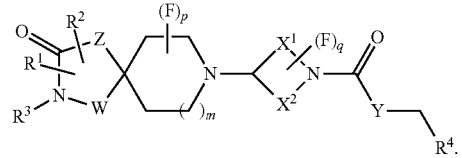

Formula B.

In other embodiments, the method comprises contacting the non-isolated compound of Formula A (e.g. directly from a condensation reaction performed to form the compound of Formula A) with a reducing agent in an aprotic polar or non-polar solvent optionally comprising an acid.

In some embodiments, the moiety

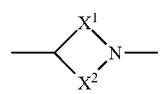

is an azabicyclo-heptane, azabicyclo-octane, or azabicyclo-nonane ring system.

In some embodiments, the moiety

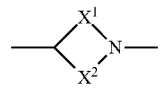

is selected from the following ring system wherein q is 0, 1, or 2:

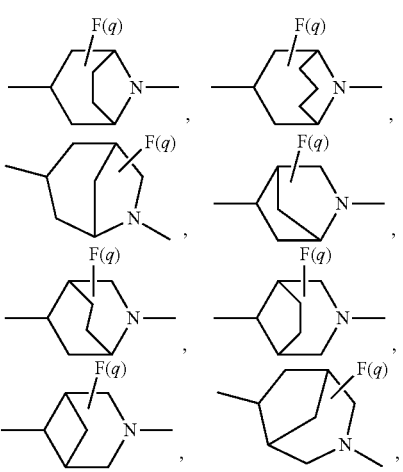

-continued

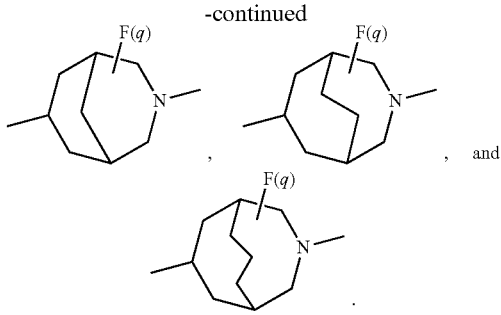

, and

In some embodiments, the moiety

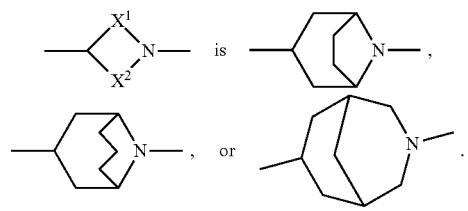

In some embodiments, the moiety

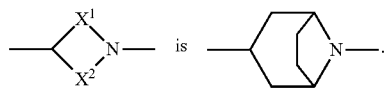 is 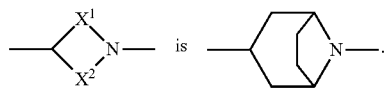.

In some embodiments, the compound of Formula A is isolated as described herein.

In some embodiments, the isolated compound of Formula A is contacted with a reducing agent to afford the compound of Formula B by dissolving and/or suspending the isolated compound in a solvent (e.g. an aprotic polar or non-polar solvent) and adding to the resulting solution and/or suspension a reducing agent to reduce the compound to an amine.

In some embodiments, the compound of Formula B is obtained with high diastereo-selectivity. In some embodiments, the diastereo-selectivity was determined by appropriate analytical instrument, such as HPLC, before the reduction was subject to purification procedures. Purification procedures are known to those skilled in the art and can include, for example, chromatographic purification, recrystallization, and others identifiable to a skilled person.

In some embodiments, the compound of Formula B obtained before purification has an exo:endo isomer ratio of at least 70:30 as determined by, for example, HPLC. In some embodiments, the ratio is greater than or equal to 75:25. In some embodiments, the ratio is greater than or equal to 80:20. In some embodiments, the ratio is greater than or equal to 85:15. In some embodiments, the ratio is greater than or equal to 90:10. In some embodiments, the ratio is greater than or equal to 95:5. In some embodiments, the ratio is greater than or equal to 99:1.

In some embodiments, the compound of Formula B obtained before purification has an endo:exo isomer ratio of at least 70:30 as determined by, for example, HPLC. In some embodiments, the ratio is greater than or equal to 75:25. In some embodiments, the ratio is greater than or equal to 80:20. In some embodiments, the ratio is greater than or equal to 85:15. In some embodiment, the ratio is greater than or equal to 90:10. In some embodiments, the ratio is greater than or equal to 95:5. In some embodiments, the ratio is greater than or equal to 99:1.

In some embodiments, the reducing agent is selected from boron hydrides such as $NaBH_4$, $NaBH(OAc)_3$, $NBu_4BH_4$, $NaBH(OAc)_3$, $NaCNBH_3$, and $NMe_4BH(OAc)_3$. In some embodiments, the reducing agent is selected from silicon hydrides such as $HSiCl_3$, $Et_3SiH$, $HSiPh_3$, and $HSiPh(CH_3)_2$.

In some embodiments, the aprotic polar or non-polar solvent is selected from xylenes, toluene, alkanes, $CHCl_3$, $CH_2Cl_2$, methyl tert-butyl ether, acetonitrile, propionitrile, tetrahydrofuran, and 2-methyl tetrahydrofuran.

In some embodiments, the optional acid is a $C_1$ to $C_{10}$ carboxylic acid (alkanoic acid). In some embodiments, the optional acid is selected from hexanoic acid and acetic acid.

In some embodiments, the reduction is conducted at room temperature, for example at a temperature from 15° C. to 25° C.

In some embodiments, the compound of formula B is selected from

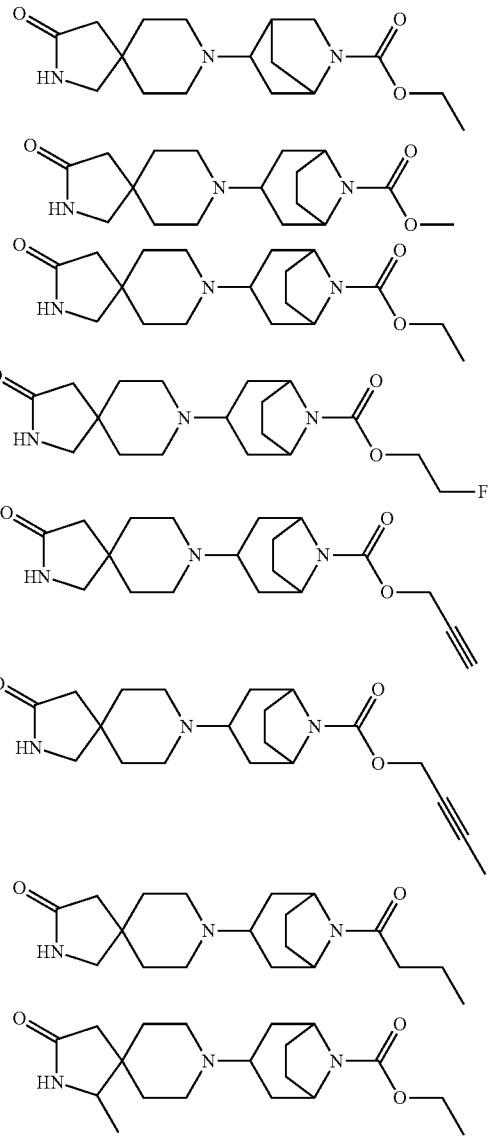

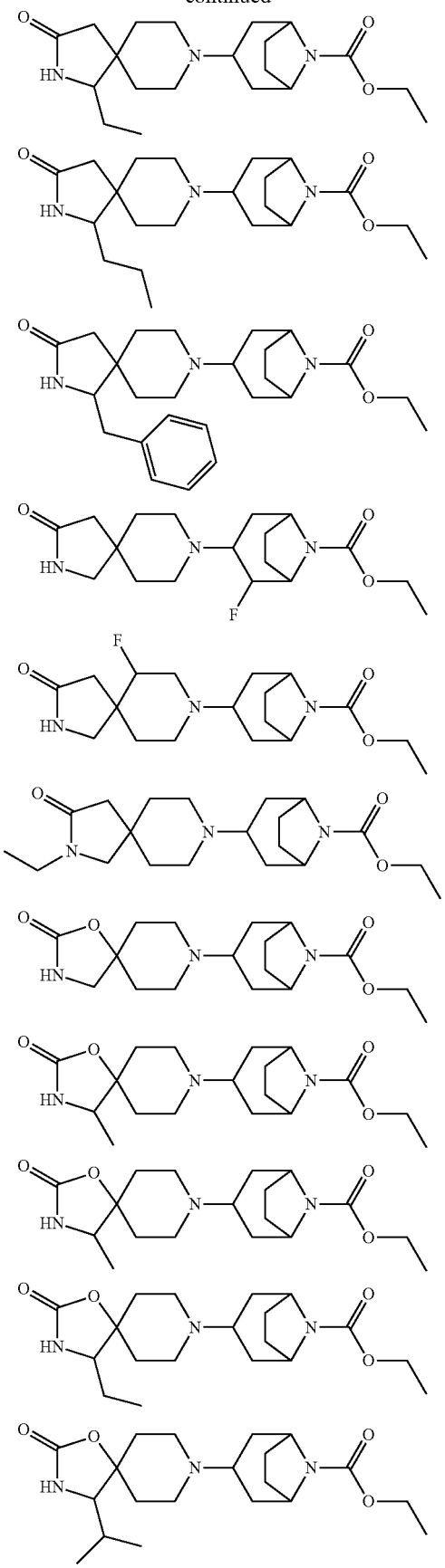
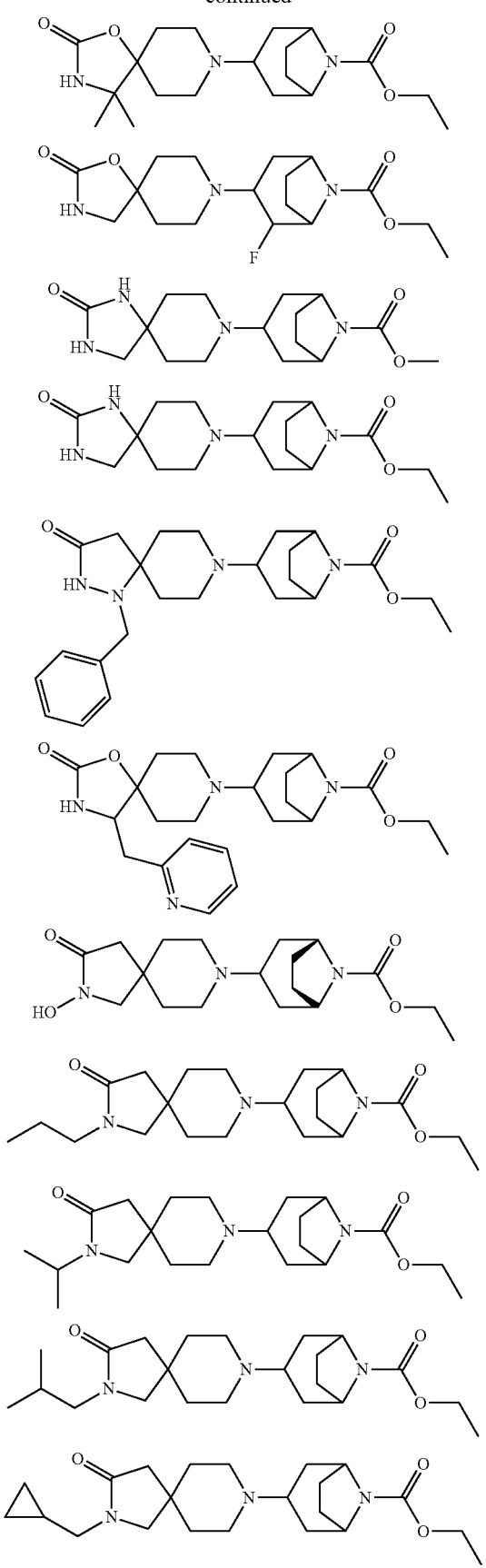

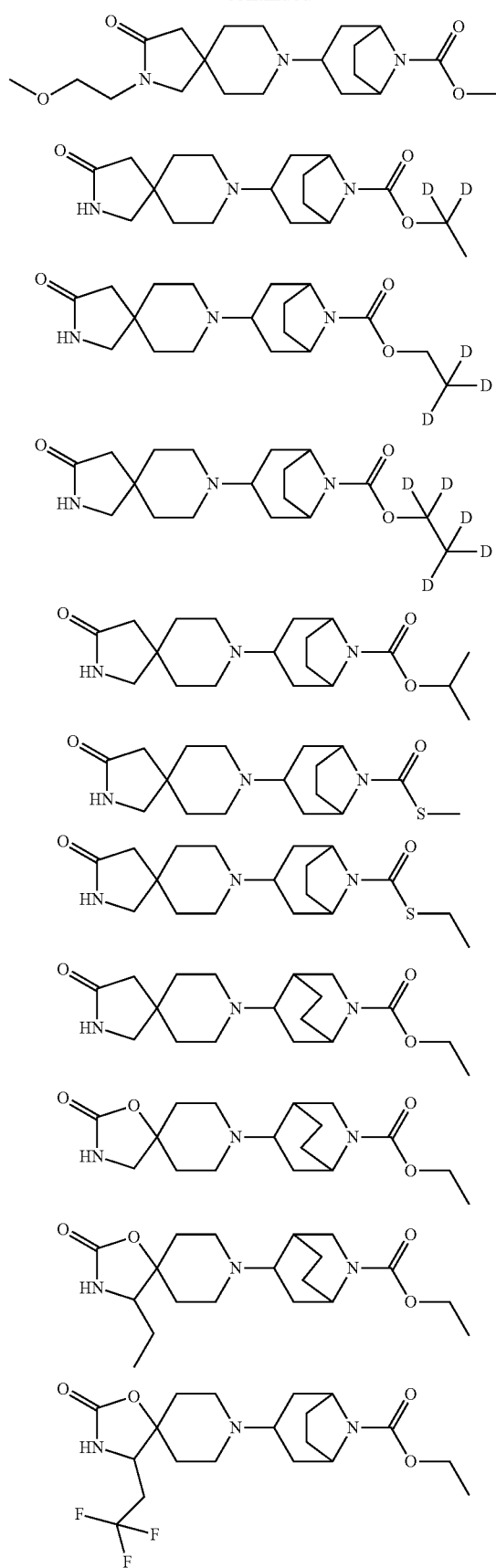
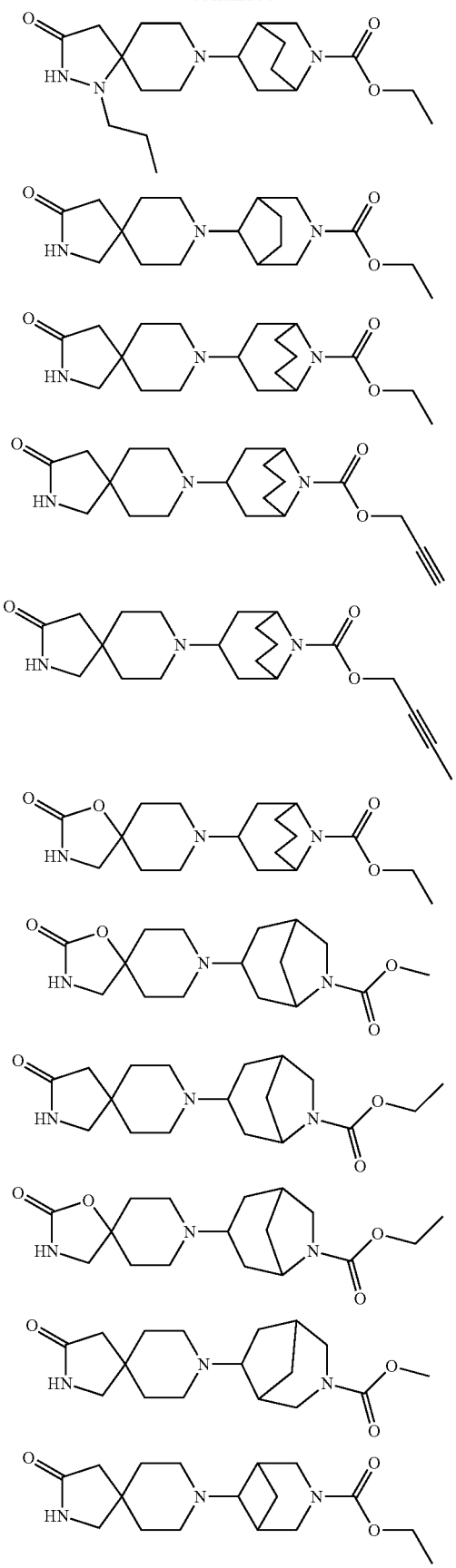

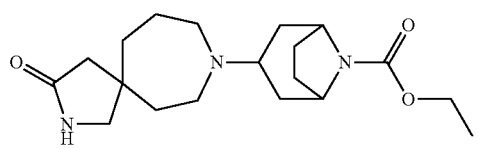

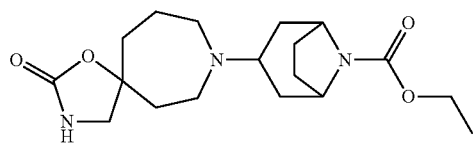

wherein each of the compounds of Formula B has a ratio of endo:exo of at least 70:30 as determined by HPLC before purification. In some embodiments, the ratio is greater than or equal to 75:25. In some embodiments, the ratio is greater than or equal to 80:20. In some embodiments, the ratio is greater than or equal to 85:15. In some embodiment, the ratio is greater than or equal to 90:10. In some embodiments, the ratio is greater than or equal to 95:5. In some embodiments, the ratio is greater than or equal to 99:1.

In some embodiments, the compounds of Formula B shown above are compounds in which each of the compounds of Formula B has a ratio of exo:endo of at least 70:30 as determined by HPLC before purification. In some embodiments, the ratio is greater than or equal to 75:25. In some embodiments, the ratio is greater than or equal to 80:20. In some embodiments, the ratio is greater than or equal to 85:15. In some embodiment, the ratio is greater than or equal to 90:10. In some embodiments, the ratio is greater than or equal to 95:5. In some embodiments, the ratio is greater than or equal to 99:1.

In some embodiments, the compound of Formula B is selected from

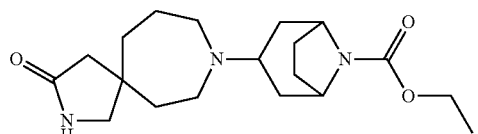

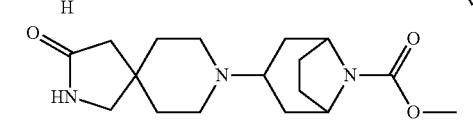

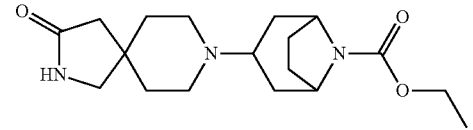

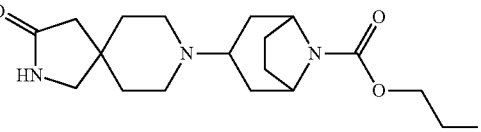

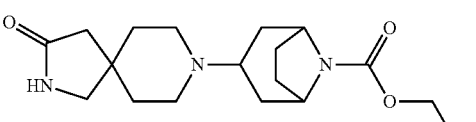

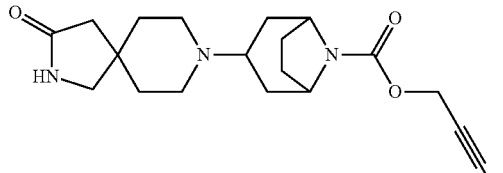

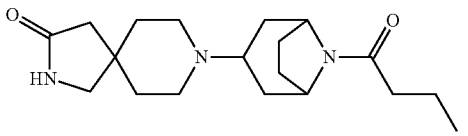

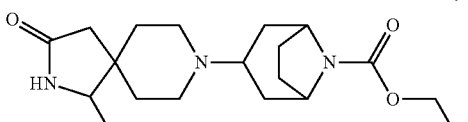

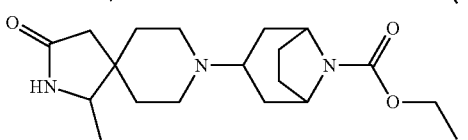

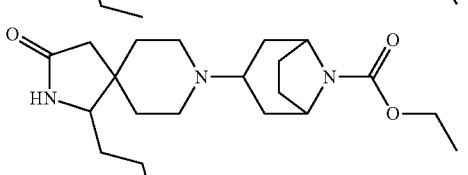

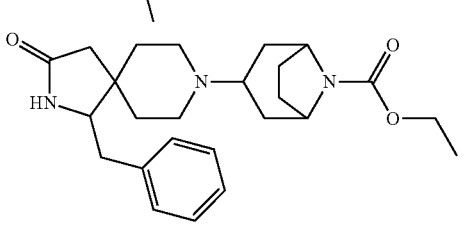

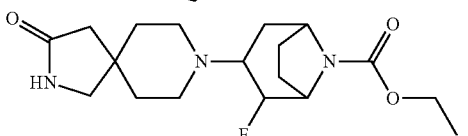

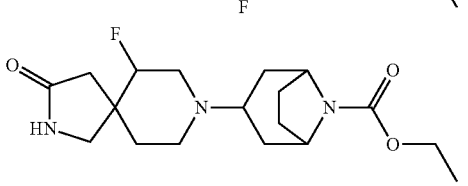

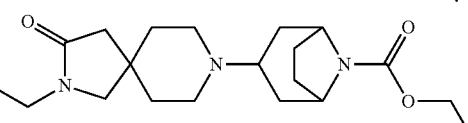

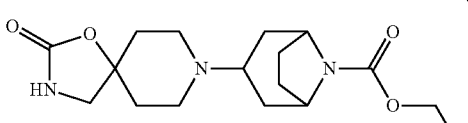

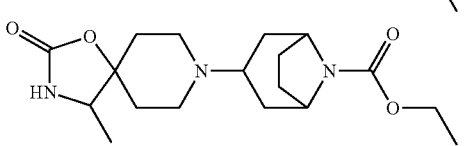

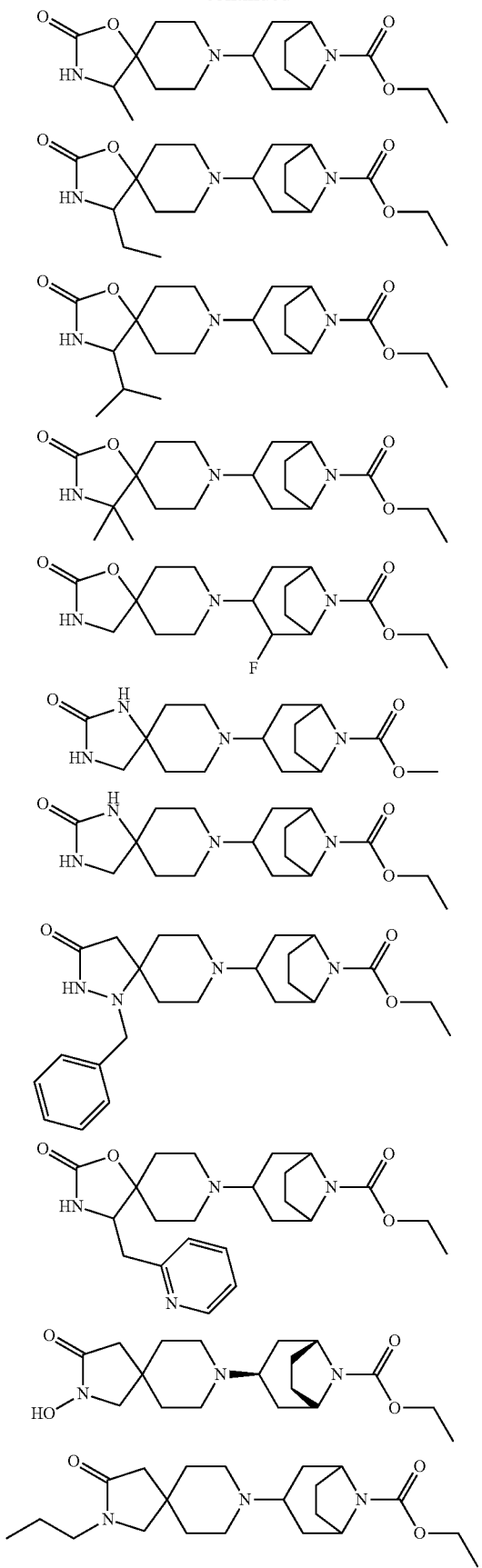
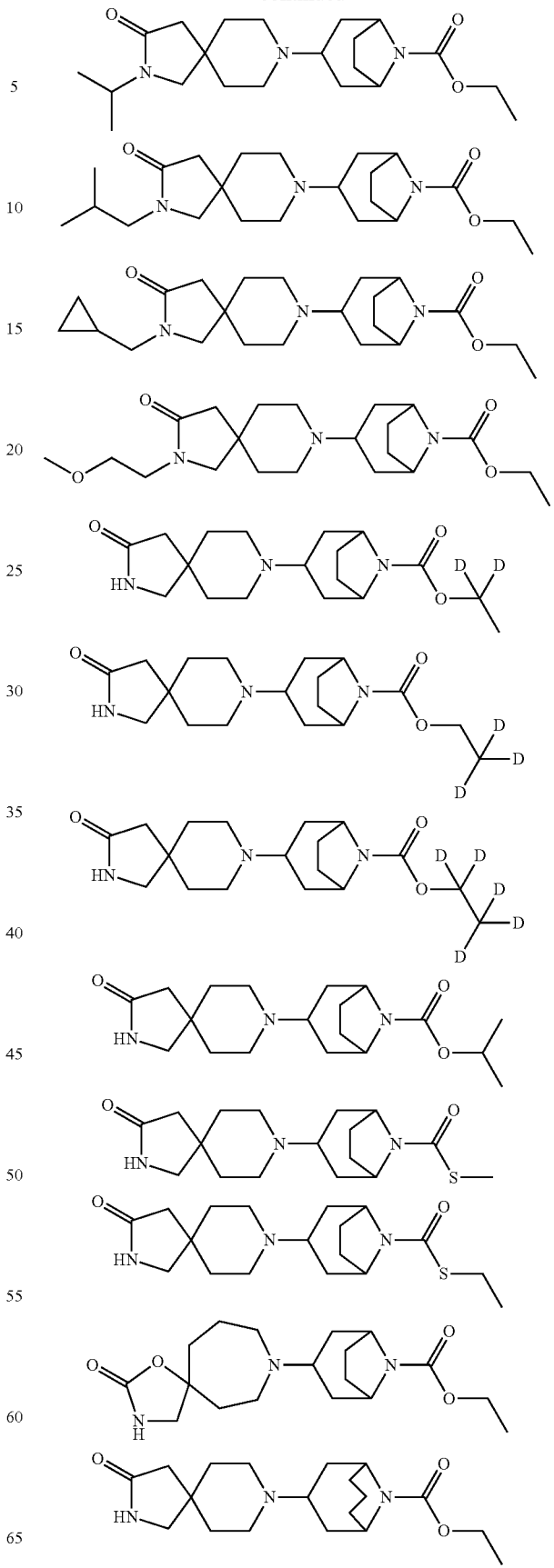

-continued

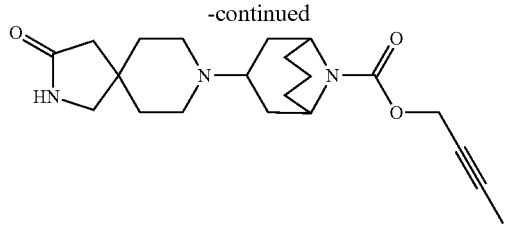
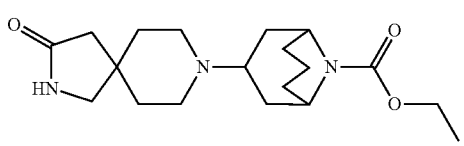
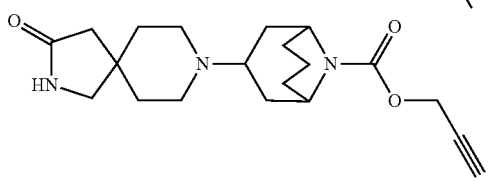

wherein each of the compounds of Formula B has a ratio of endo:exo of at least 70:30 as determined by HPLC before purification. In some embodiments, the ratio is greater than or equal to 75:25. In some embodiments, the ratio is greater than or equal to 80:20. In some embodiments, the ratio is greater than or equal to 85:15. In some embodiment, the ratio is greater than or equal to 90:10. In some embodiments, the ratio is greater than or equal to 95:5. In some embodiments, the ratio is greater than or equal to 99:1.

In some embodiments, the compounds of Formula B shown above are compounds in which each of the compounds has a ratio of exo:endo of at least 70:30 as determined by HPLC before purification. In some embodiments, the ratio is greater than or equal to 75:25. In some embodiments, the ratio is greater than or equal to 80:20. In some embodiments, the ratio is greater than or equal to 85:15. In some embodiment, the ratio is greater than or equal to 90:10. In some embodiments, the ratio is greater than or equal to 95:5. In some embodiments, the ratio is greater than or equal to 99:1.

In some embodiments, the compound of Formula B is selected from

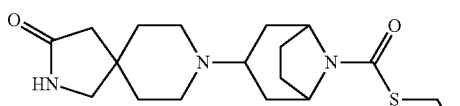
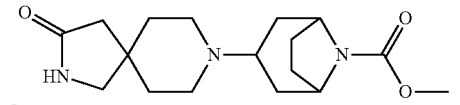
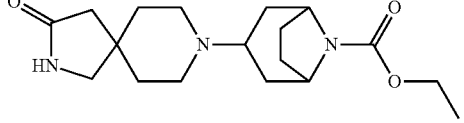
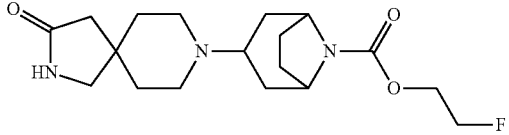

-continued

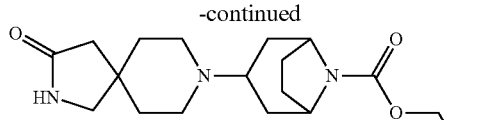
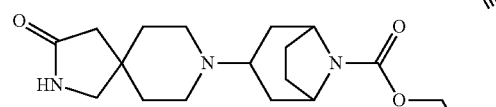
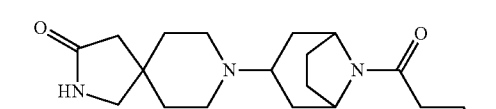
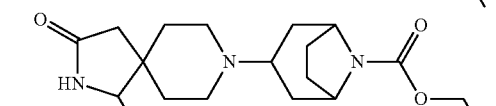
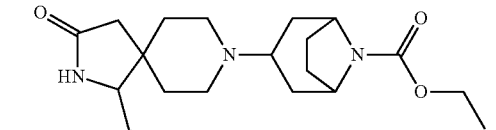
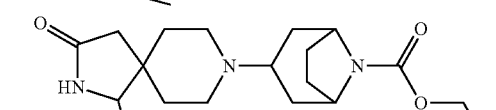
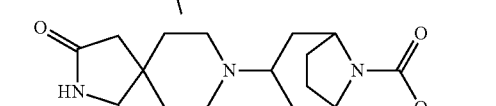
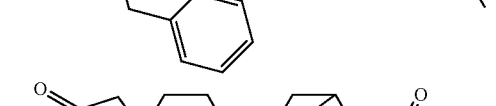
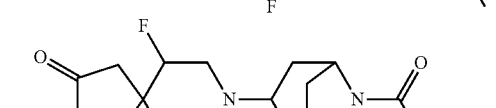
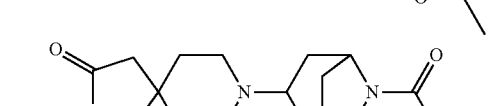
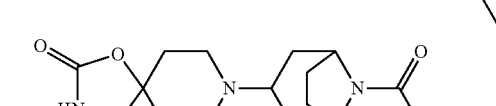

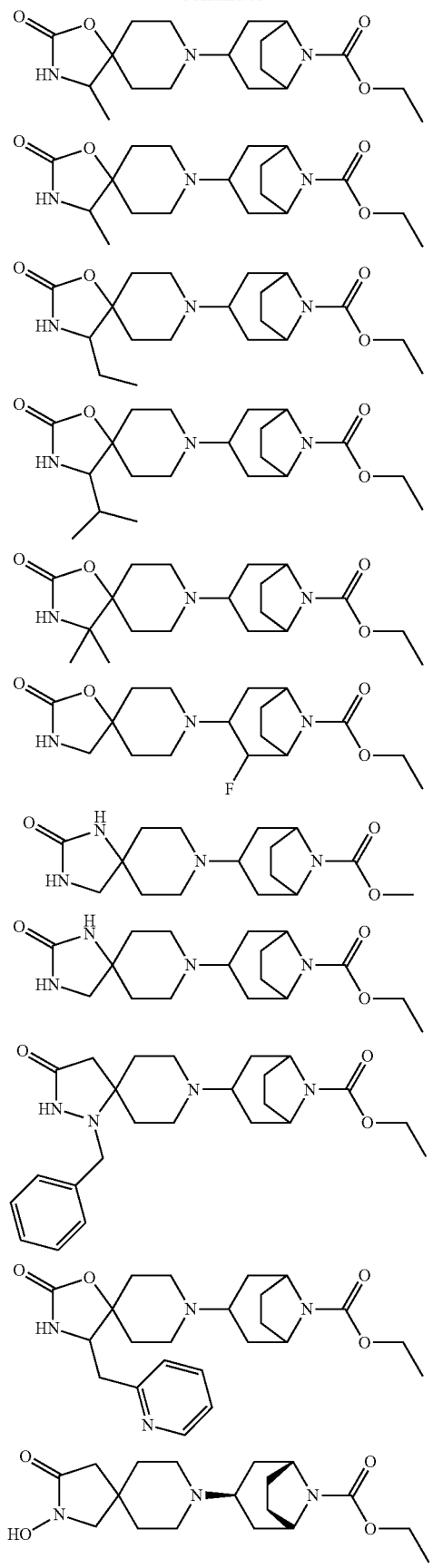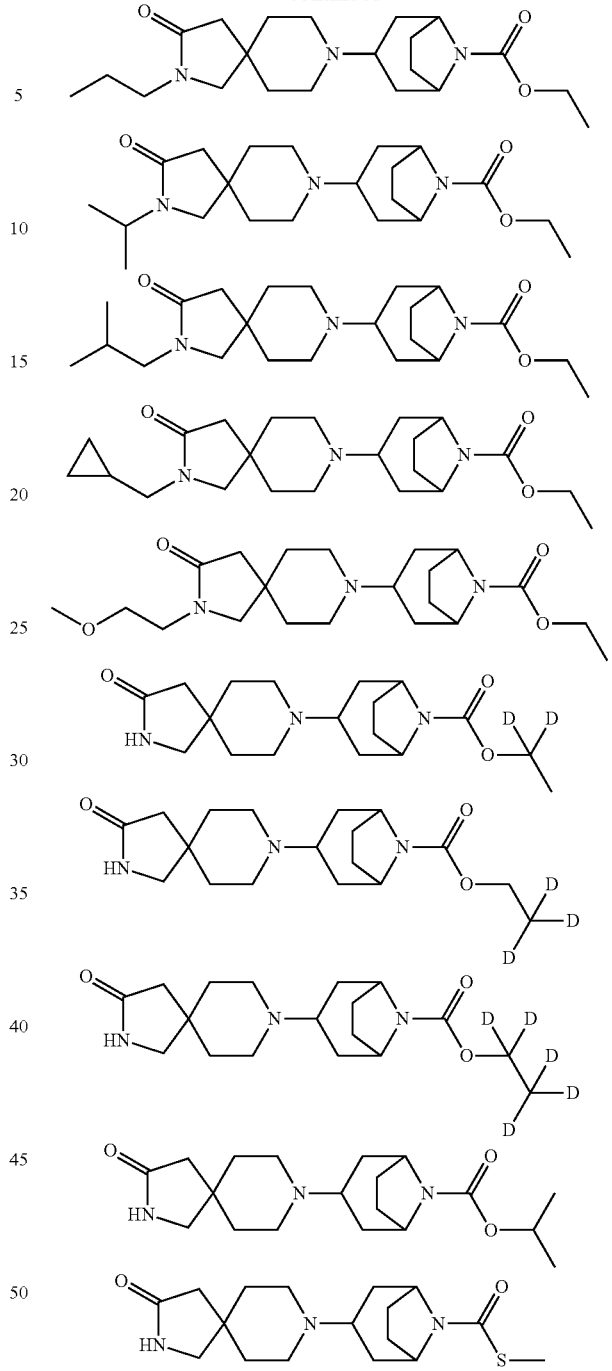

wherein each of the amine has a ratio of endo:exo of at least 70:30 as determined by HPLC before purification. In some embodiments, the ratio is greater than or equal to 75:25. In some embodiments, the ratio is greater than or equal to 80:20. In some embodiments, the ratio is greater than or equal to 85:15. In some embodiment, the ratio is greater than or equal to 90:10. In some embodiments, the ratio is greater than or equal to 95:5. In some embodiments, the ratio is greater than or equal to 99:1.

In some embodiments, the compounds of Formula B shown above are compounds in which each of the compounds has a ratio of exo:endo of at least 70:30 as determined by HPLC before purification. In some embodiments, the ratio is greater than or equal to 75:25. In some embodiments, the ratio is greater than or equal to 80:20. In some embodiments, the ratio is greater than or equal to 85:15. In some embodiment, the ratio is greater than or equal to 90:10. In some embodiments, the ratio is greater than or equal to 95:5. In some embodiments, the ratio is greater than or equal to 99:1.

In some embodiments, the compound of Formula B is converted to a pharmaceutically acceptable salt. In some embodiments, the pharmaceutically acceptable salt is a hydrochloride salt.

In some embodiments, the method also comprises refluxing a mixture of a ketone of Formula C, a secondary amine of Formula D or a salt thereof, and an acidic catalyst in a non-polar solvent to obtain the compound of Formula A:

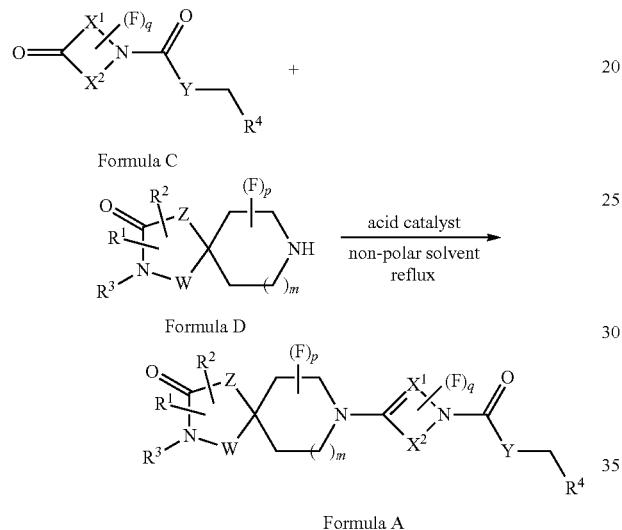

wherein $R^1$-$R^4$, Y, Z, W, m, p, and q are the same as described herein for Formula A, including each embodiment thereof, and $X^1$ and $X^2$ are hydrocarbons which together contain a total of five to nine carbon atoms and which link together such that the moiety:

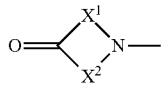

forms a bridged bicyclic ring system. The water by-product is removed from the reaction system during the reaction with, for example, sieve dryer or Dean-Stark (at reflux). After the reaction is completed as determined by, for example, LCMS, the compound of Formula A can be isolated from the reaction mixture via crystallization. The crystallization can be accomplished by cooling the reaction mixture to room temperature, adding another non-polar solvent, optionally seeding the mixture with the previously formed compound of Formula A, and collecting the solid compound precipitation.

In some embodiments, the moiety

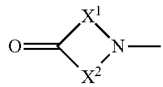

is selected from the following ring system wherein q is 0, 1, or 2:

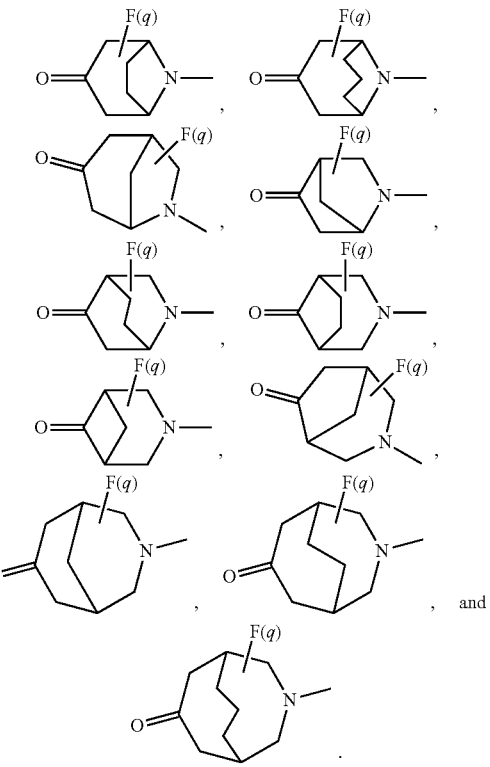

In some embodiments, the moiety

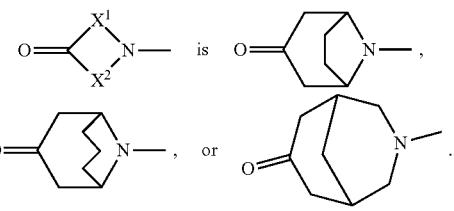

In some embodiments, the moiety

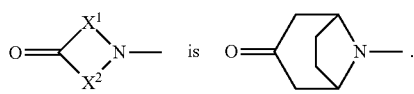

In some embodiments, the non-polar solvent is xylenes. In some embodiments, the another non-polar solvent is hexane, heptane, or octane. In some embodiments, the catalytic acid is a $C_1$ to $C_{10}$ carboxylic acid (alkanoic acid). In some embodiments, the catalytic acid hexanoic acid.

In general, the ketone of Formula C and the secondary amine of Formula D are either commercially available or can be prepared according to procedures described in PCT/GB2015/050807.

In some embodiments, the ketone of formula C is selected from

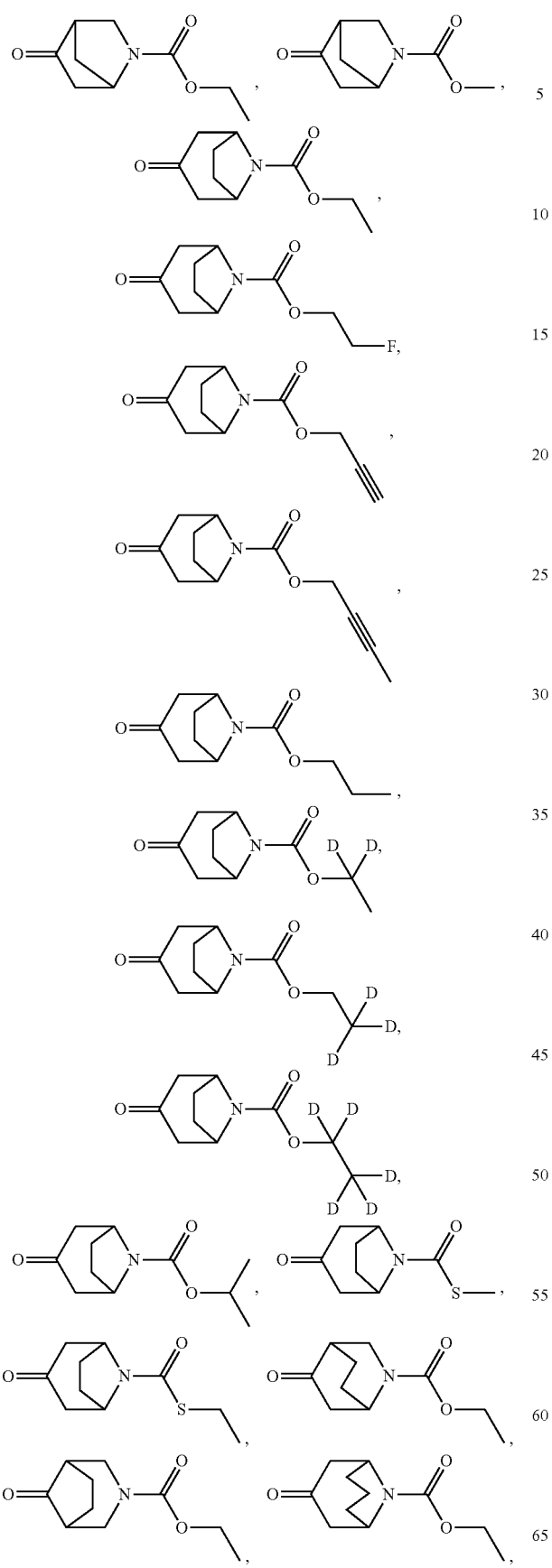
,
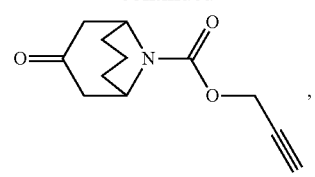
,
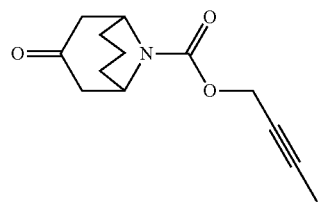
,
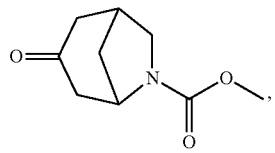
,
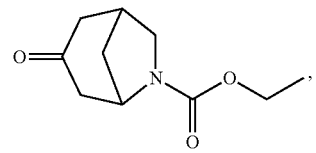
,
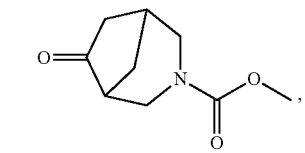
,
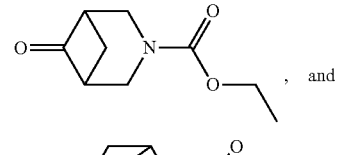
, and
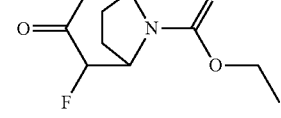
.
In some embodiments, the secondary amine of Formula D is selected from
 
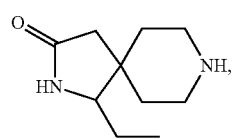 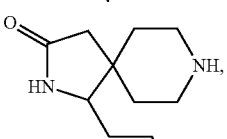

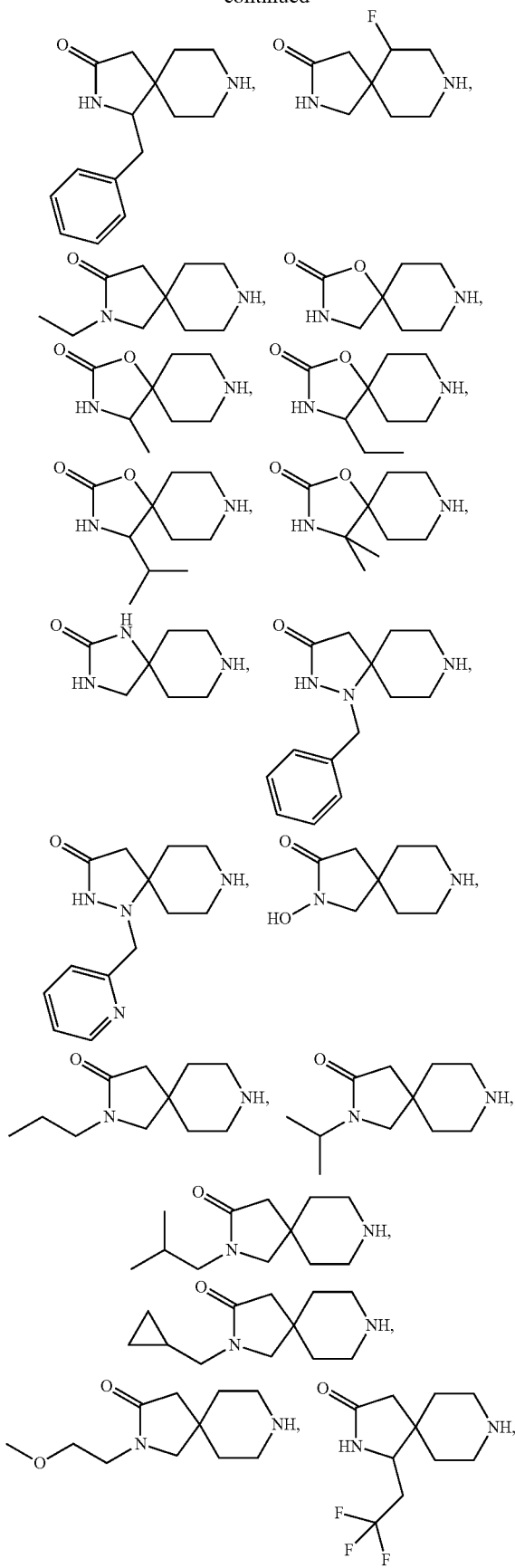

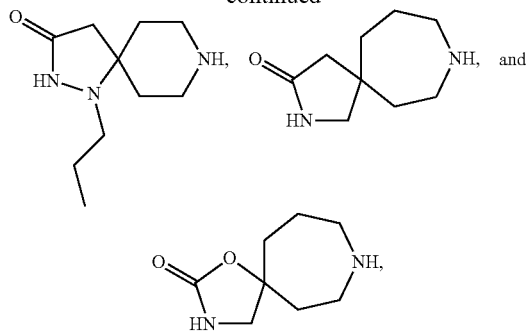

or a salt thereof.

EXAMPLES

The following examples are illustrative in nature and are in no way intended to be limiting.

HPLC used to determine the diastero-selectivity of the reduction had the following profile:

Agilent 1100 HPLC; Eclipse XDB-C18 50×4.6 mm; 1.8-micron column;
Solvent A—Water (4 L), 85% H3PO4 (4.2 g), Triethylamine (5.2 g), pH=7.27;
Solvent B—Acetonitrile
Isocratic—6 min 80% A
Flow Rate—1.5 ml/min
UV Detection (210 nm)
Retention time: 1.62 minutes (compound 4-endo), 1.20 minutes (compound 4-exo)

The endo and exo configuration of the compounds synthesized as described herein were confirmed by using authentic standards of the endo and exo isomers that had their confirmations confirmed by single-crystal analysis.

Example 1

Preparation of ethyl 3-(3-oxo-2,8-diazaspiro[4.5]decan-8-yl)-8-azabicyclo[3.2.1]oct-2-ene-8-carboxylate (Compound 3)

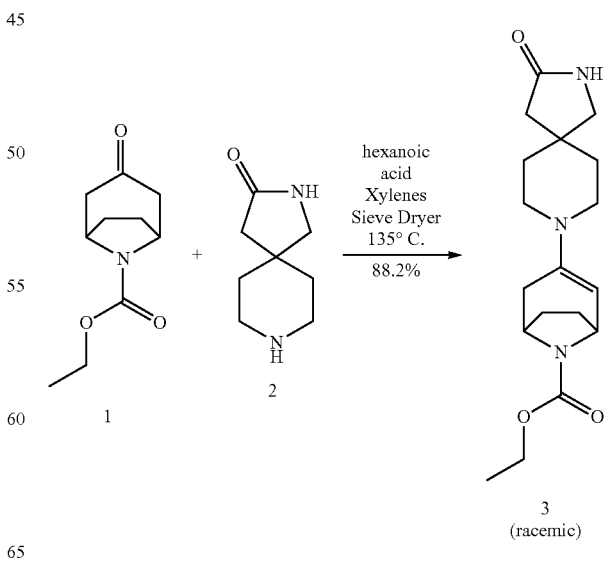

To a 500 ml round bottom flask was added Compound 1 (ethyl-3-oxo-8-azabicyclo[3.2.1]octane-8-carboxylate)

(34.39 g, 174.4 mmol), Compound 2 (2,8-diazaspiro[4.5]decan-3-one) (24.16 g, 151.3 mmol), xylenes (227.5 g, 714.3 mmol), and hexanoic acid (0.441 g, 3.80 mmol). The resulting slurry was refluxed through a column of molecular sieves (188.0 g, 1579 mmol) overnight. After aminolactam was not detectable by NMR, the reaction mixture was cooled and transferred to a 1 L round bottom flask with toluene (12.09 g, 131.2 mmol) rinse. Heptane (88.3 g, 881 mmol) was added to the 1 L round bottom flask. The resulting mixture was seeded with 40 mg of compound 3. More heptane (500.0 ml, 3413 mmol) was added dropwise via addition funnel. The solid was collected by filtration. After washing with heptane (96.45 ml, 658.4 mmol), the solid crystals were dried under nitrogen overnight to give compound 3. Yield: 46.53 g, 95.6 wt % purity by QNMR, 88.2% purity corrected yield. MS ES+: 334.2. $^1$H NMR (400 MHz, DMSO-$d_6$) δ 1.15 (t, J=6 Hz, 3H), 1.3-1.6 (m, 5H), 1.6-1.9 (m, 3H), 1.9-2.2 (m, 3H), 2.6-2.8 (m, 5H), 3.01 (s, 2H), 3.9-4.1 (m, 2H), 4.29 (bs, 2H), 4.82 (d, J=4 Hz, 2H), 7.51 (s, 1H).

Example 2

Small Scale Reduction of Compound 3 into Ethyl (1R,3r,5S)-3-(3-oxo-2,8-diazaspiro[4.5]decan-8-yl)-8-azabicyclo[3.2.1]octane-8-carboxylate (Compound 4) Exo and Endo Isomers

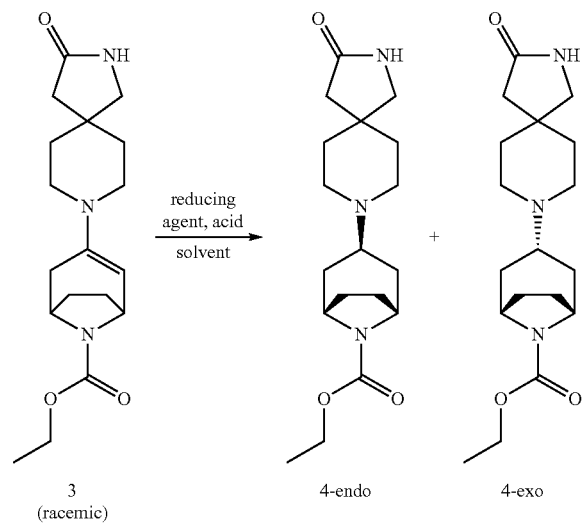 [SMILES: CCOC(=O)N1C2C=C(N3CCC4(CC3)CNC(=O)C4)CC1CC2 ; CCOC(=O)N1[C@@H]2CC[C@H]1C[C@@H](N1CCC3(CC1)CNC(=O)C3)C2 ; CCOC(=O)N1[C@@H]2CC[C@H]1C[C@H](N1CCC3(CC1)CNC(=O)C3)C2]

3 (racemic)    4-endo    4-exo

Compound 3 was subjected to a series of different combinations of solvents, acids, and reducing agents as set forth in the table below

| Solvent | Carboxylic Acid | Reducing Agent | 4-endo (wt %) | 4-exo (wt %) | Procedure |
|---|---|---|---|---|---|
| Xylenes | Hexanoic acid | HSiCl$_3$ | 98.4 | 1.6 | A |
| Xylenes | HOAc | NMe$_4$BH(OAc)$_3$ | 74.4 | 25.6 | B |
| Xylenes/hexanes/TBAI | Hexanoic acid | NaBH(OAc)$_3$ | 70.6 | 29.4 | C |
| Xylenes | HOAc | NaBH(OAc)$_3$ | 69.0 | 31.0 | D |
| 2-MeTHF | HOAc | NaBH(OAc)$_3$ | 60.2 | 39.8 | E |
| CH$_2$Cl$_2$ | HOAc | NaBH(OAc)$_3$ | 59.4 | 40.6 | F |

-continued

| Solvent | Carboxylic Acid | Reducing Agent | 4-endo (wt %) | 4-exo (wt %) | Procedure |
|---|---|---|---|---|---|
| THF | HOAc | NaBH(OAc)$_3$ | 54.3 | 45.7 | E |
| DMF | HOAc | NaBH(OAc)$_3$ | 52.7 | 47.4 | E |
| DMSO | HOAc | NaBH(OAc)$_3$ | 51.4 | 48.6 | E |
| ACN | HOAC | NaBH(OAc)$_3$ | 31.7 | 68.3 | E |
| 0.5M LiCl in THF | HOAc | NaBH(OAc)$_3$ | 25.8 | 74.2 | E |
| Xylenes | Hexanoic acid | NaCNBH$_3$ | 22.6 | 77.3 | G |
| Ethylene glycol | HOAc | NaBH(OAc)$_3$ | 19.9 | 80.1 | E |
| Xylenes | Hexanoic acid | NBu$_4$BH$_4$ | 9.4 | 90.6 | H |
| 1.9M ZnCl$_2$ in 2-MeTHF | HOAc | NaBH(OAc)$_3$ | 8.4 | 91.6 | E |
| Ethylene glycol | HOAc | NaBH$_4$ | 8.0 | 92.0 | E |

TBAI: tetra-n-butylammonium iodide

Procedure A: To a mixture of compound 3 (0.1372 g, 0.3456 mmol), xylenes (3.0672 g), and hexanoic acid (0.090 g, 0.77 mmol) was added trichlorosilane (100.0 µL, 0.9908 mmol). After stirring 1 day at room temperature, HPLC (50 µL in 0.5 ml MeOH) showed complete conversion to a mixture of compound 4 (98.4%) and exo isomer (1.6 area %). Water (5 ml) was added and the solids removed by vacuum filtration and washed with water (5 ml) and methanol (5 ml). The filtrate was concentrated to 10 ml total volume and loaded on a 30 g C18 column packed with 0.1% trifluoroacetic acid (TFA) in water. The product was eluted with 3 column volumes of 0.1% TFA in water then with a gradient from 0% to 40% (0.07 vol % TFA in ACN) in (0.1 vol % TFA in water) over 4 column volumes. Compound 4 eluted at 30-38% (0.07 vol % TFA in ACN) in (0.1 vol % TFA in water). The product fractions were concentrated to dryness on a lyophilizer to give a white solid 0.130 g (83.7%). NMR of a 1:1 mixture of this solid with a standard of compound 4 showed one compound.

Procedure B: To a mixture of compound 3 (0.0696 g, 0.175 mmol) and xylenes (2.917 g) was added tetramethylammonium triacetoxyborohydride (0.1450 g, 0.5511 mmol) followed by acetic acid (0.0230 g, 0.383 mmol). After 24 hours, methanol (5.1 g) was added. HPLC (50 µL in 0.5 ml MeOH) shows 74.4:25.6 (compound 4: exo isomer).

Procedure C: To a mixture of compound 3 (0.1603 g, 0.404 mmol), xylenes (4.20 g), hexane (6.21 g), hexanoic acid (0.1075 g, 0.9255 mmol) and tetra-n-butylammonium iodide (0.1450 g, 0.5511 mmol) was added sodium triacetoxyborohydride (0.3304 g, 1.559 mmol). After 41 min at room temperature, HPLC (50 µL in 0.5 ml MeOH) showed 70.6:29.4 (compound 4: exo isomer).

Procedure D: To a mixture of compound 3 (0.0686 g, 0.173 mmol) and xylenes (2.78 g) was added sodium triacetoxyborohydride (0.1313 g, 0.6195 mmol) and acetic acid (0.0230, 0.383 mmol). After 1 day at room temperature, HPLC (50 µL in 0.5 ml MeOH) showed 69.0:31.0 (compound 4: exo isomer).

Procedure E: Compound 3 (0.0050 g, 0.0012 mmol) and acetic acid (0.0230 g, 0.383 mmol) were mixed with solvent (0.7 ml) and reducing agent (0.093 mmol for NaBH(OAc)$_3$, 0.26 mmol for NABH$_4$). The resultant ratio of compound 4 to exo isomer formed was then determined by HPLC (neat injection).

Procedure F: To a mixture of compound 3 (0.1095 g, 0.3284 mmol) and methylene chloride (2.47 g) was added sodium triacetoxyborohydride (0.1490 g, 0.7030 mmol) and acetic acid (0.0230, 0.383 mmol). After 20 min at room temperature, HPLC (50 µL in 0.5 ml MeOH) shows 59.4:40.6 (compound 4: exo isomer).

Procedure G: To a mixture of compound 3 (0.132 g, 0.332 mmol) and xylenes (3.46 g) was added hexanoic acid (0.0685 g, 0.590 mmol) and sodium cyanoborohydride (0.042 g, 0.665 mmol). After 4 hours at room temperature, HPLC (50 µL in 0.5 ml DMF) showed 22.6:77.3 (compound 4: exo isomer).

Procedure H: To a mixture of compound 3 (0.132 g, 0.332 mmol) and xylenes (3.46 g) was added hexanoic acid (0.0685 g, 0.590 mmol) and tetrabutylammonium borohydride (0.171 g, 0.665 mmol). After 15 min at room temperature, HPLC (50 µL in 0.5 ml DMF) showed 9.4:90.6 (compound 4: exo isomer).

Example 3

Larger-Scale Preparation of ethyl (1R,3r,5S)-3-(3-oxo-2,8-diazaspiro[4.5]decan-8-yl)-8-azabicyclo[3.2.1]octane-8-carboxylate (Compound 4)

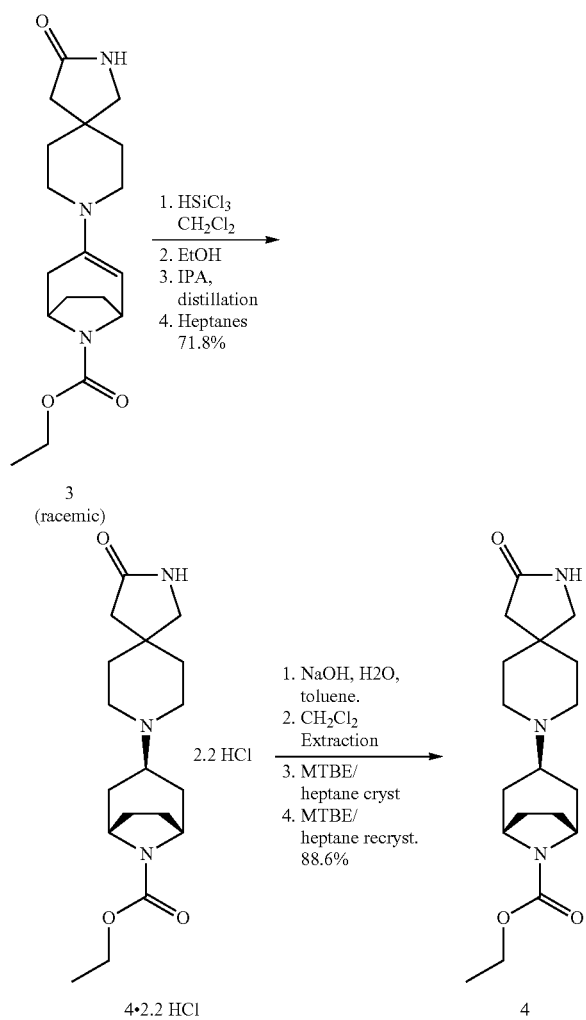

To a 1 L round bottom flask was added ethyl 3-(3-oxo-2,8-diazaspiro[4.5]decan-8-yl)-8-azabicyclo[3.2.1]oct-2-ene-8-carboxylate (Compound 3, 63.42 g, 178.6 mmol) and CH$_2$Cl$_2$ (695.44 g, 8188.2 mmol). The mixture was cooled to −5° C. and trichlorosilane (47.57 g, 351.2 mmol) was added over about 2 minutes while maintaining the temperature of the mixture less than 5° C. The flask was placed in a 0° C. bath. After about one and half hours, the flask was placed in a 20° C. bath. After about one hour, the flask was placed at a 15.8° C. bath. After another about 4 hours, HPLC indicted about 2% Compound 3 was left. The reaction was left to stir at room temperature for overnight.

HPLC showed the reaction was completed, 98.5% product was the endo isomer, and 1.5% product was the exo isomer. After the reaction mixture was cooled to 0° C., ethanol (78.66 g, 1707 mmol) was added (the first quarter was added over about 3 minutes and the rest was added over about another 3 minutes) while maintaining the reaction mixture at a temperature of less than 22° C. The solution was stirred at 18° C. for about one hour before isopropyl alcohol was added over about 2 minutes. The mixture was concentrated on rotavap to give 487.9 g net weight. Constant volume distillation was performed while adding isopropyl alcohol (760.0 ml, 9928 mmol). After about 30 minutes for distillation at 40 C rotavap bath temperature, a slurry of 418.1 g was obtained. The slurry was cooled to 20° C. Heptane (590.0 g, 5888 mmol) were slowly added with vigorous stirring. After about two and half hours, additional heptane (104.5 g, 1043 mmol) was added. After stirring for 16 hours, the slurry was left to stand for weekend (more than two days). The solid was collected by filtration and washed with heptane (117 g, 1170 mmol). The solid was dried under nitrogen pressure. Yield: 66.07 g, HPLC showed 90.2 area % purity, 72.2 wt % (as mono HCl salt), the exo:endo ratio is about 0.99:99.01. MS ES+: 336.2. Further experiment showed that the molar ratio of HCl to the amine is 1:2.2 (Compound 4•2.2 HCl).

A 2 L round bottom flash was charged with ethyl (3-endo)-3-(3-oxo-2,8-diazaspiro[4.5]dec-8-yl)-8-azabicyclo[3.2.1]octane-8-carboxylate hydrochloride (Compound 4-endo•2.2 HCl, 65.490 g, 127.14 mmol) and Toluene (355.9 g, 3863 mmol). To the resulting slurry was added water (318.7 g, 17690 mmol) to afford a biphasic solution. The phases were separated, and the organic phase was extracted with water (59.7 g, 3310 mmol).

To the combined aqueous portions was added methylene chloride (381 g, 4480 mmol). The pH was adjusted to 1.44 to 11.86 with sodium hydroxide (22.6 g, 282 mmol) while keeping the solution at 17 to 19° C. with mild ice water bath cooling. The phases were separated, and the aqueous layer was extracted with methylene chloride (270.0 g, 3179 mmol). The combined organic portions were dried over magnesium sulfate (22.4 g, 186 mmol) and concentrated to 277.3 g net weight.

To the concentrate was added 2-Methoxy-2-methylpropane (159.5 g, 1809 mmol). A constant volume distillation was performed while adding 2-Methoxy-2-methylpropane (620 mL, 5200 mmol) to afford a slurry with a final weight of 252.62 g. Heptane (237.6 g, 2371 mmol) was slowly added over about 3 minutes and the resulting mixture was stirred at room temp for 1 hour. The solids were collected via filtration and were washed with washed with heptane. Dried under nitrogen pressure overnight. Yield: 40.26 g. HPLC showed 97.7 area % purity, 97.8 wt % (92.3% yield from 2.2 HCl salt), 0.29 area % exo isomer and 99.57% endo isomer (endo:exo ratio 99.57:0.29).

Of the 40.26 g of above free-based Compound 4, 39.97 g was combined with 6.35 g of Compound 4 from another batch for an additional recrystallization. The combined portions of Compound 4 were added to a 2 L round bottom flask. Methylene chloride (130.4 g, 1535 mmol) was added to afford a solution. To the solution was added 2-Methoxy-2-methylpropane (333 g, 3780 mmol) and the mixture remained a solution.

The solution was seeded with some previously produced solid Compound 4 and the mixture was stirred for 30 minutes to afford a slurry. Heptane (299.5 g, 2989 mmol) was added over a period of 5 minutes. The mixture was concentrated to 549.6 g net weight on a rotovap. At 16° C., HPLC of supernatant showed 5% product loss to filtrate. The concentrate was placed in ice water bath and was cooled to 0.5° C. over about an hour. The solids were then collected by filtration and were washed with heptane. Dried under nitrogen pressure overnight. Yield: 43.50 g. HPLC shows 99.7 area % purity, 100.2 wt % (96.0% recovery), 0.07 area % exo isomer 99.72 area % endo isomer (endo:exo ratio 99.72:0.07). $^1$H NMR (400 MHz, CD$_3$OD) δ 1.27 (t, J=8 Hz, 3H), 1.6-1.7 (m 6H), 1.8-2.0 (m, 4H), 2.2-2.6 (m, 9H), 3.20 (s, 2H), 4.1-4.2 (m, 2H), 4.2-4.3 (m, 2H).

Example 4

Preparation of Mono Hydrochloride Salt of ethyl (1R,3r,5S)-3-(3-oxo-2,8-diazaspiro[4.5]decan-8-yl)-8-azabicyclo[3.2.1]octane-8-carboxylate (Compound 4•HCl)

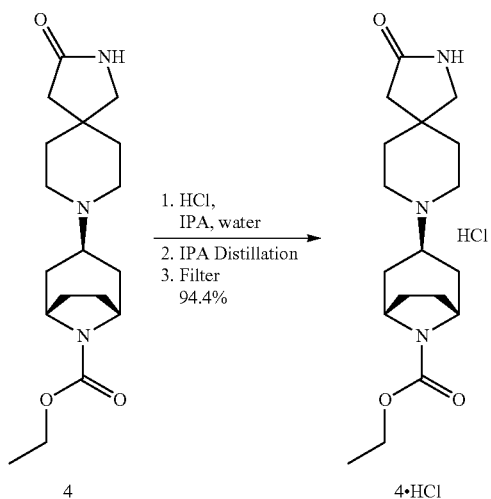 [SMILES: CCOC(=O)N1[C@@H]2CC[C@H]1C[C@@H](N1CCC3(CC1)CNC(=O)C3)C2 ; CCOC(=O)N1[C@@H]2CC[C@H]1C[C@@H](N1CCC3(CC1)CNC(=O)C3)C2 ; Cl]

A 1000 ml RBF was charged Compound 4 (42.90 g, 127.9 mmol), isopropyl alcohol (444.3 g, 7393 mmol) and water (8.49 g, 471 mmol). The pH was adjusted 8.24 to 4.40 with 37% aqueous hydrogen chloride (12.46 g, 128.2 mmol).

The mixture was warmed to reflux and water (2.97 g, 165 mmol) was added. A constant volume distillation was performed under atmospheric pressure while adding isopropyl alcohol (1260 mL, 16400 mmol). Cooled to 30° C. over 5.5 H. The product was collected via vacuum filtration and washed with isopropyl alcohol (96.5 g, 1600 mmol), then dried in a nitrogen stream to give a white solid (44.88 g, 94.4%). HPLC shows 100.0 wt % Compound 4.HCl, 99.8 area %, 0.04% exo isomer. 1H NMR (400 MHz, CD$_3$OD) δ 1.28 (t, J=7 Hz, 3H), 1.5-1.7 (m 2H), 1.7-1.8 (m, 2H), 1.8-2.2 (m, 6H), 2.3 (s, 1H), 2.4 (s, 1H), 2.7-2.7 (m, 2H), 3.05 (t, J=12 Hz, 2H), 3.1-3.2 (m, 1H), 3.24 (s, 1H), 3.38 (s, 1H), 3.58 (t, J=12H, 2H), 4.15 (q, J=7 Hz, 2H), 4.49 (bs, 2H).

Throughout this specification reference is made to publications such as US and foreign patent applications, journal articles, book chapters, and others. All such publications are expressly incorporated by reference in their entirety, including supplemental/supporting information sections published with the corresponding references, for all purposes unless otherwise indicated.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:
1. An isolated compound of Formula A:

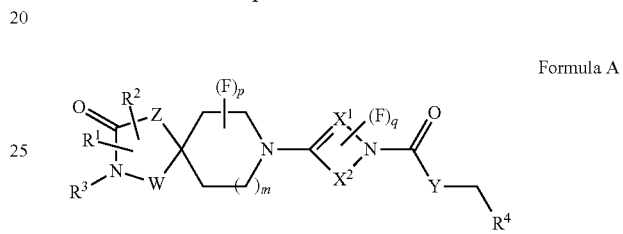

Formula A wherein:
m is 1 or 2;
p is 0, 1, or 2;
q is 0;
W is C;
Z is CH$_2$;
Y is NH, O, S, or CH2;
X$^1$ and X$^2$ are hydrocarbons which together contain a total of five to nine carbon atoms and which link together such that the moiety:

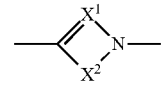

forms a bridged bicyclic ring system;
R$^1$, R$^2$ and R$^3$ are independently H or C$_{1-3}$ alkyl;
R$^4$ is H, C$_{1-5}$ alkyl, C$_{2-5}$ alkenyl, C$_{2-5}$ alkynyl, C$_{3-6}$ cycloalkyl, or C$_{3-6}$ cycloalkenyl, each of the alkyl, alkenyl, alkynyl, cycloalkyl and cycloalkenyl is optionally substituted with at least one group selected from OH, halo, CN, C$_{1-3}$ alkoxy, and NH$_2$.
2. An isolated compound which is selected from the following compounds:

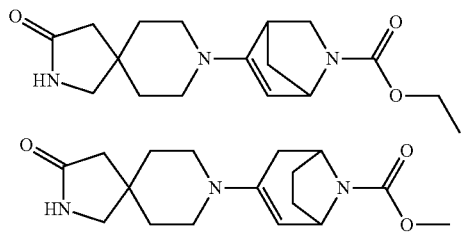

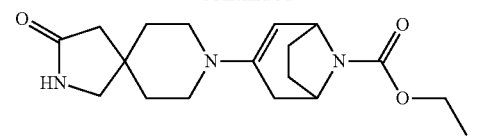
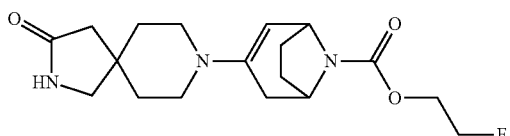
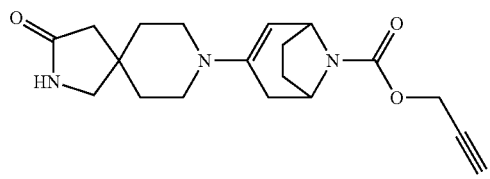
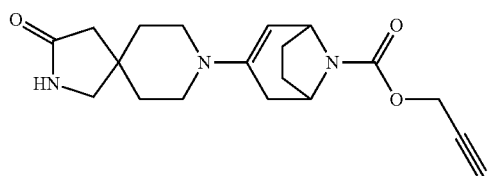
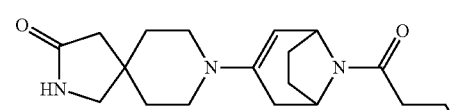
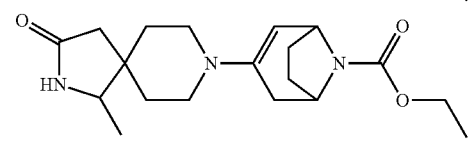
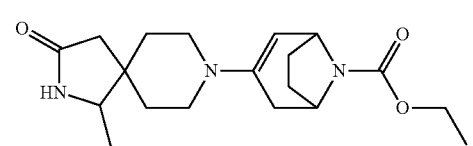
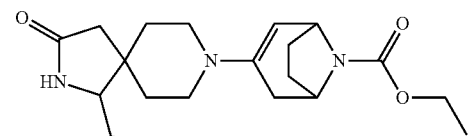
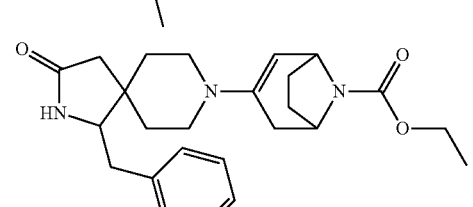
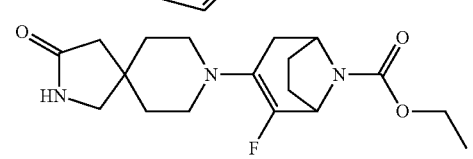
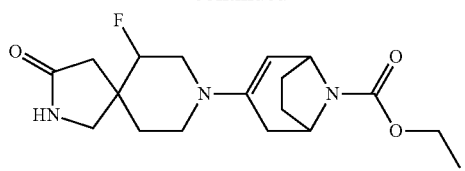
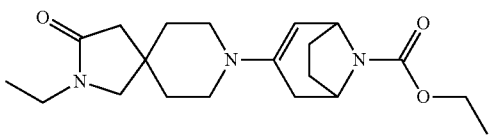
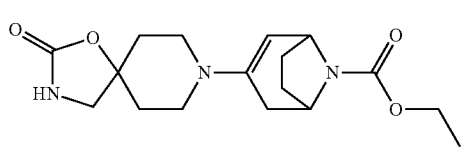
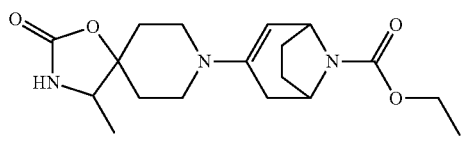
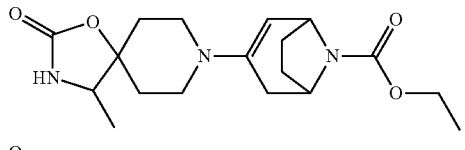
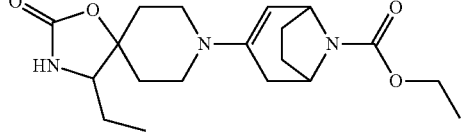
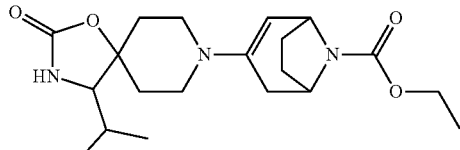
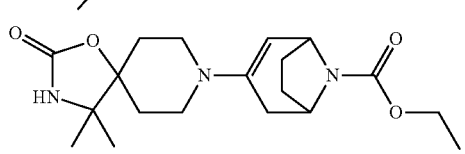
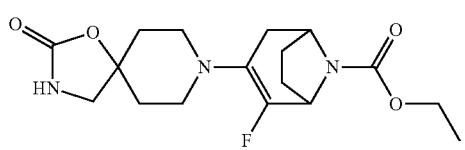
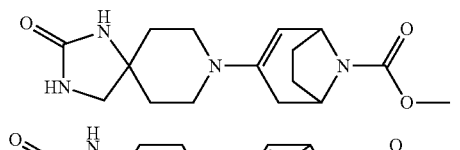

-continued
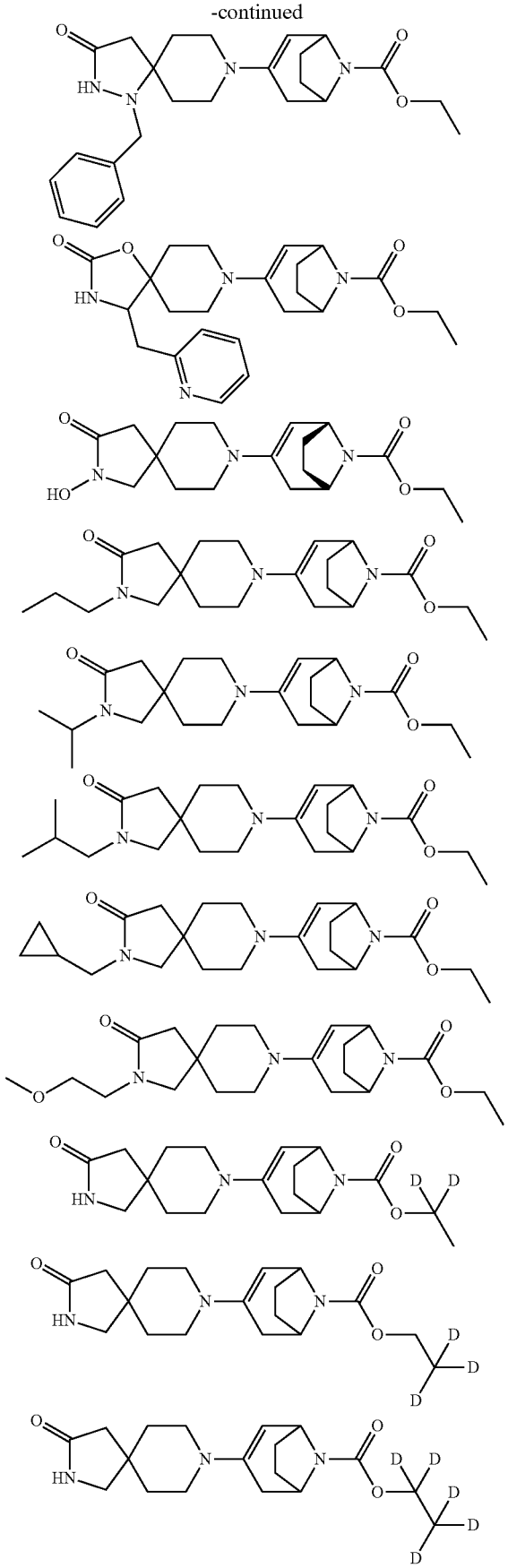
-continued
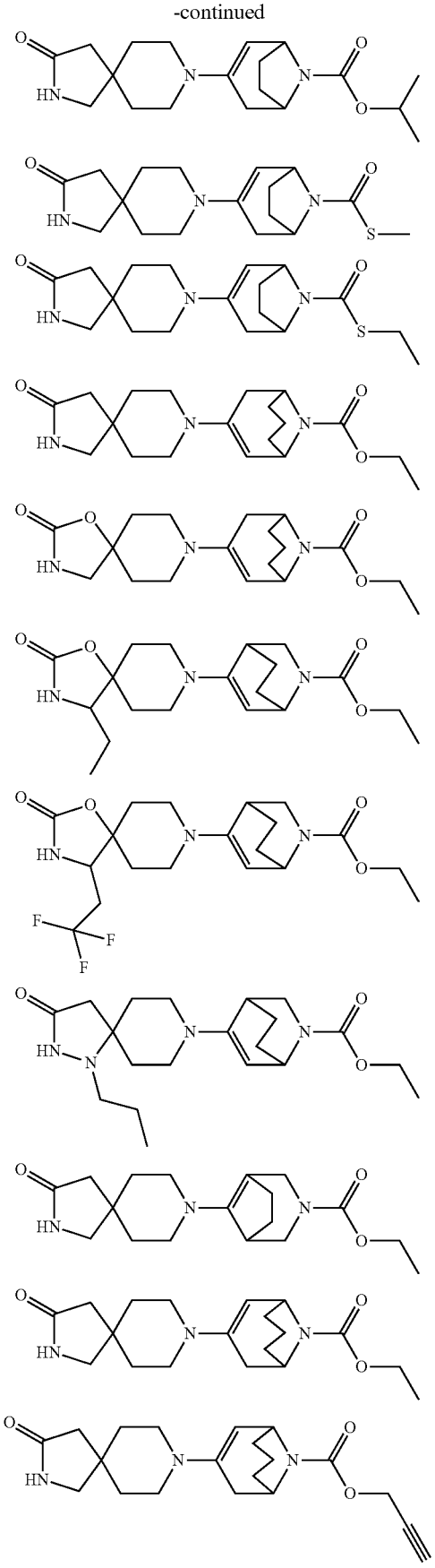

-continued

3. An isolated compound which is selected from the following compounds

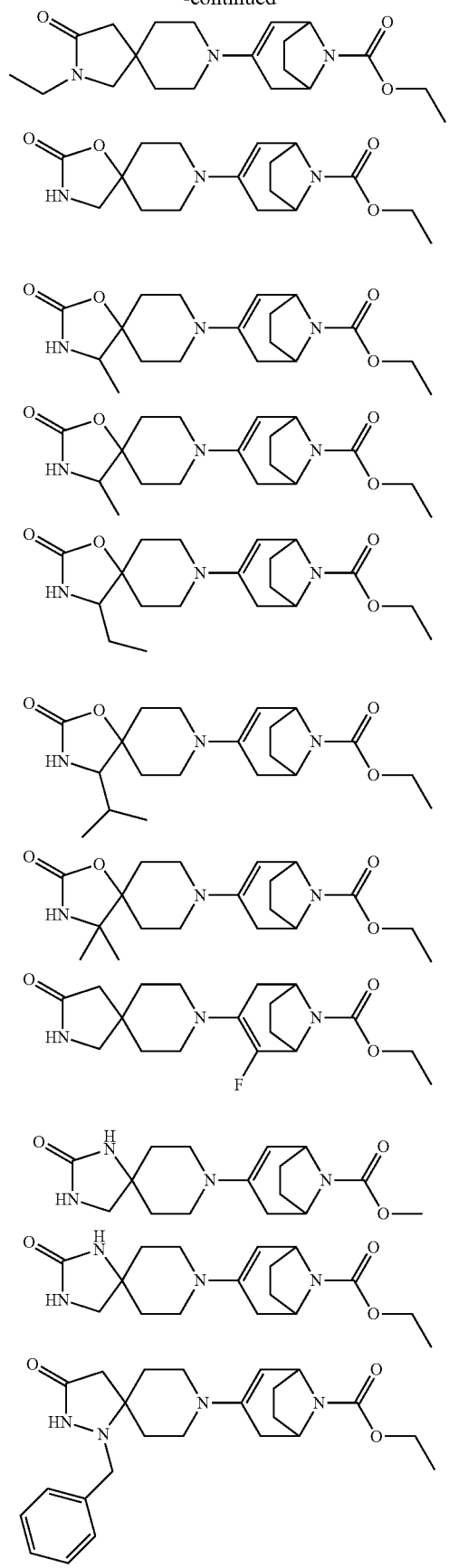
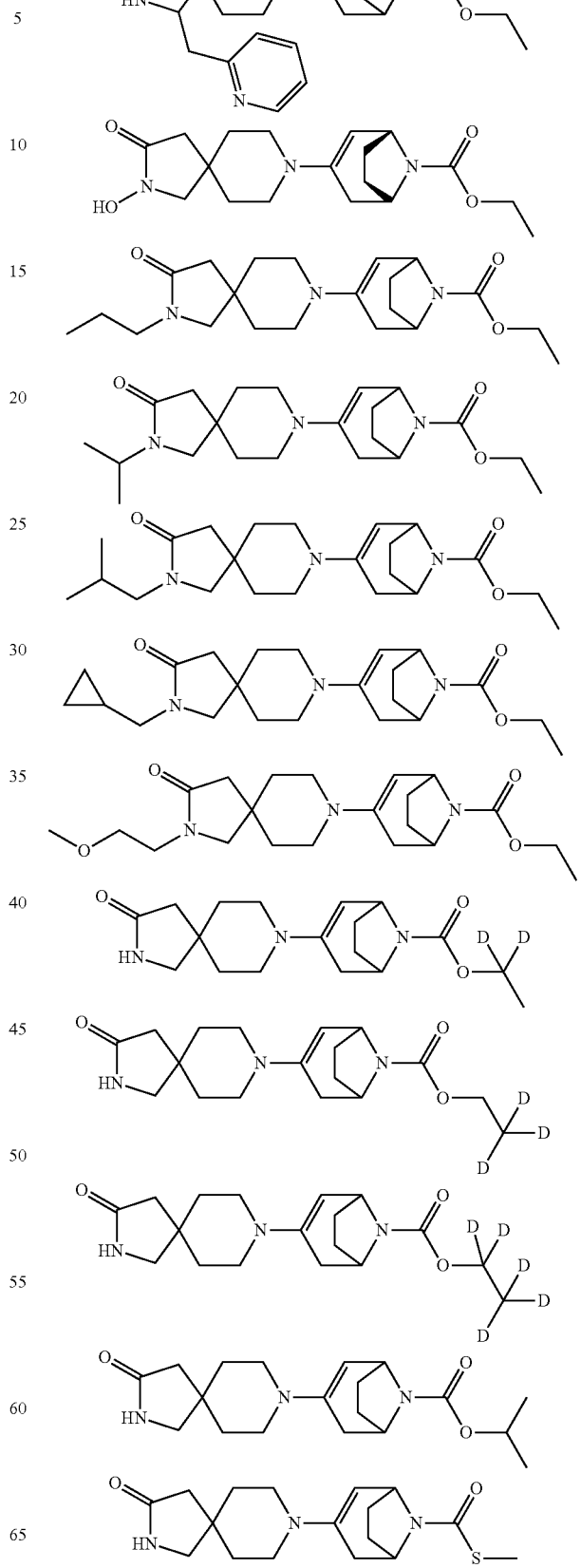

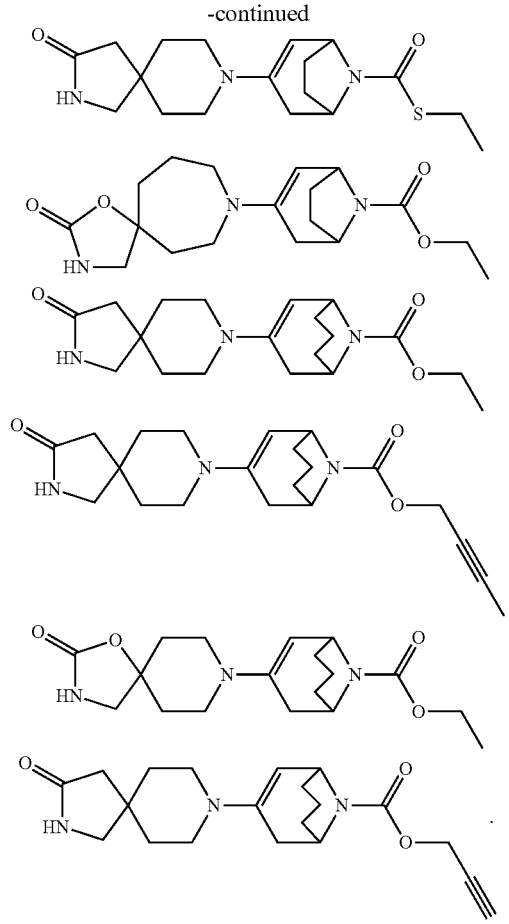
4. An isolated compound which is selected from the following compounds
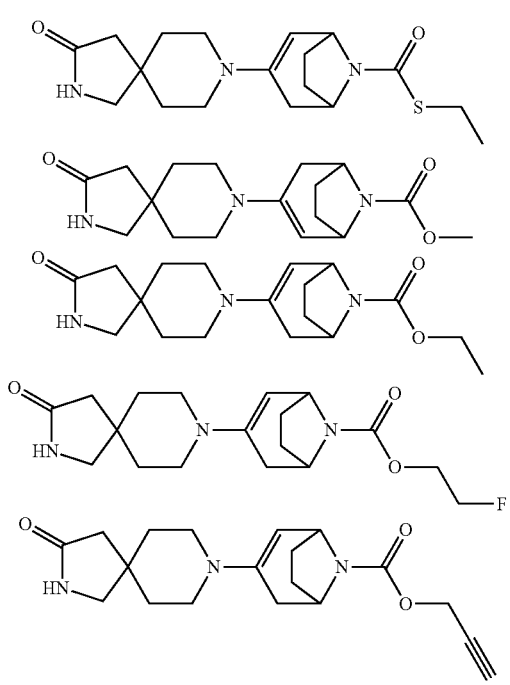
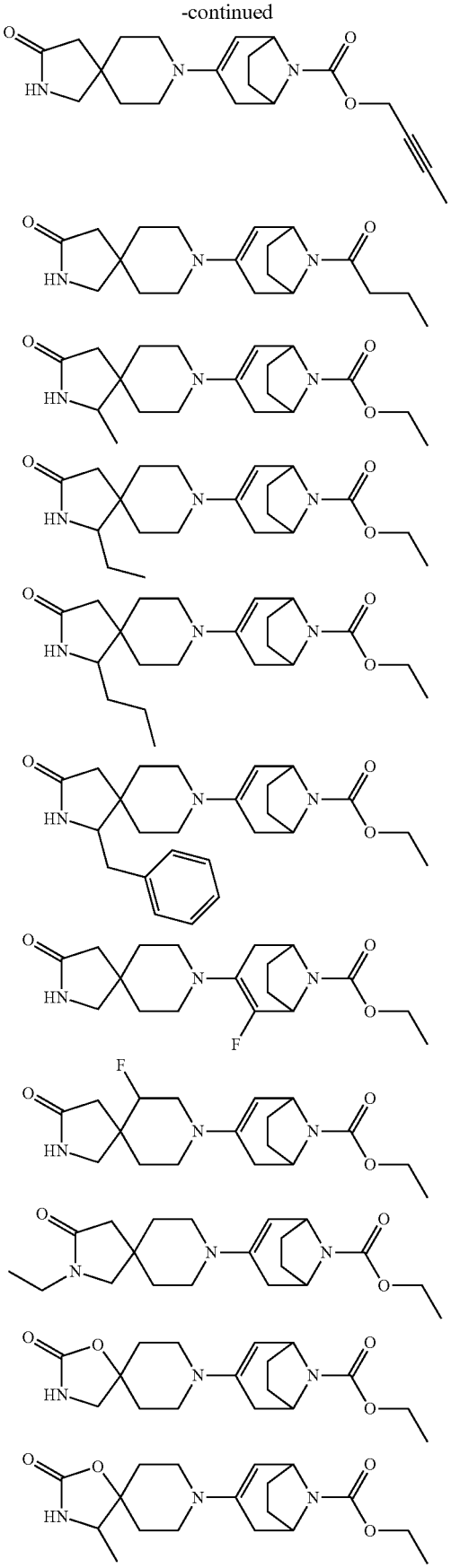

-continued
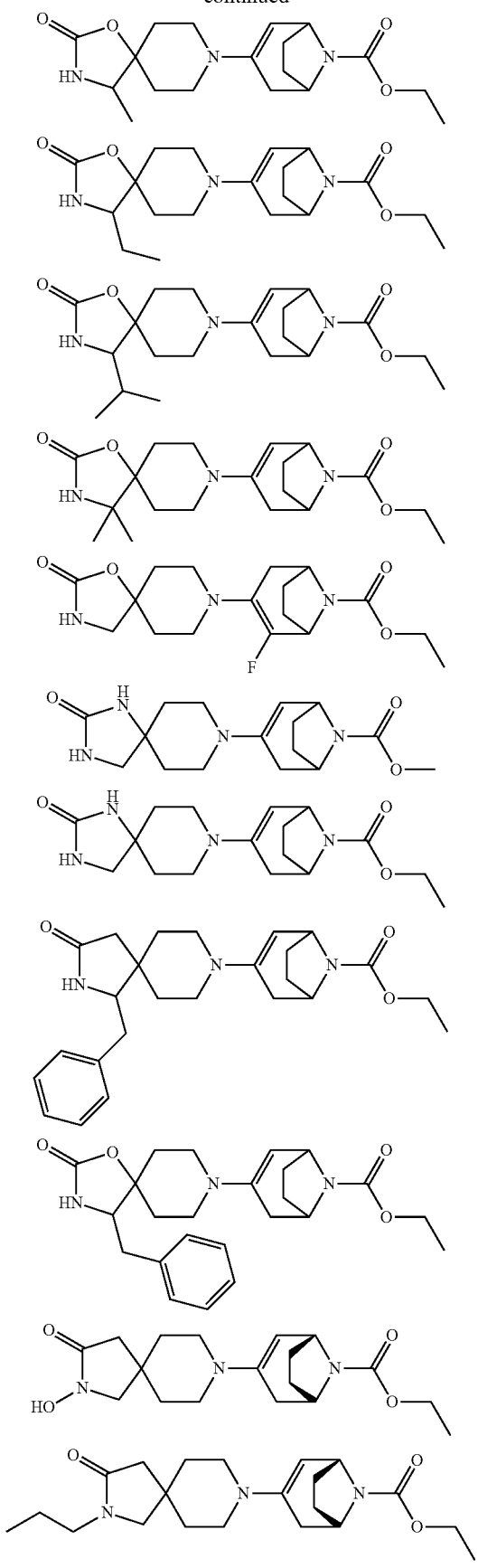
-continued
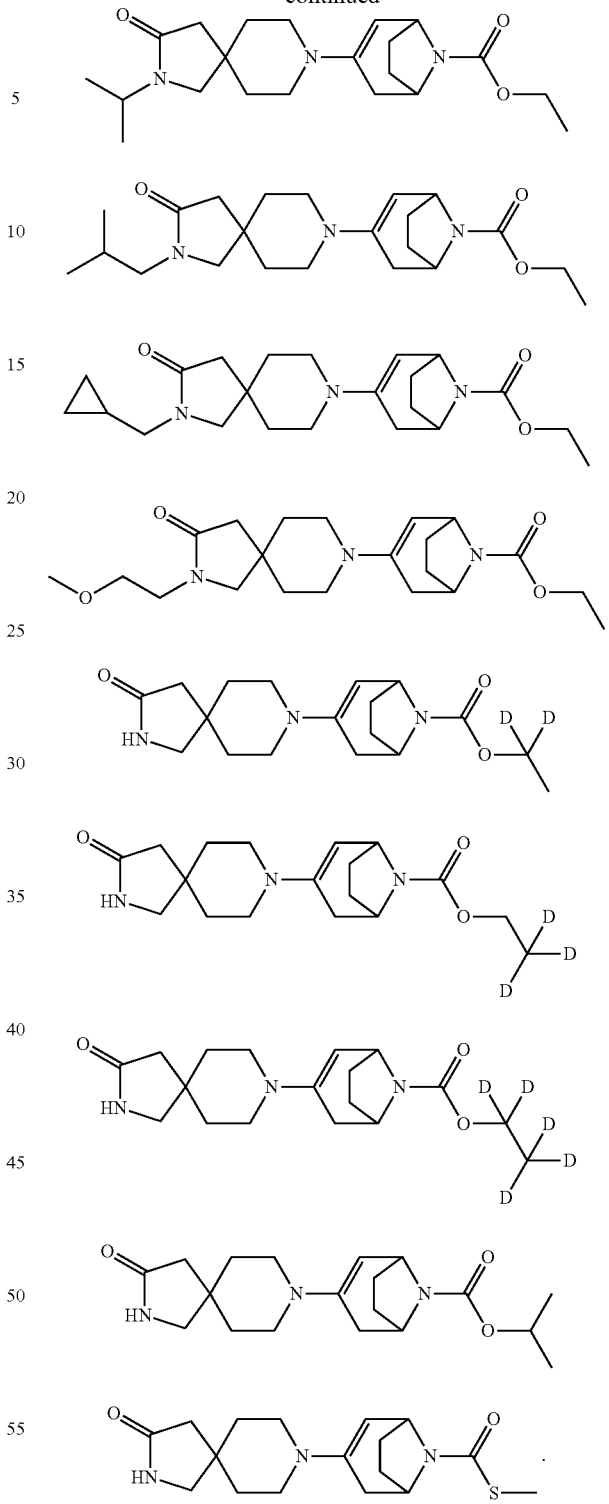
5. A method of synthesizing a compound of Formula B or a salt thereof, comprising:
contacting an isolated compound of Formula A with a reducing agent in an aprotic polar or non-polar solvent optionally comprising an acid
and, optionally, purifying the compound of Formula B, wherein the compound of Formula B is:

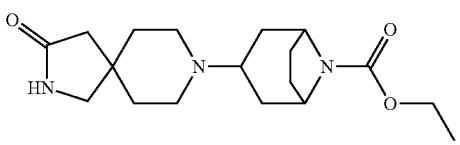

or a salt thereof, and wherein the compound of Formula A is:

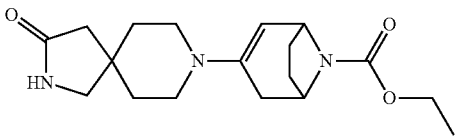 [SMILES: CCOC(=O)N1C2CCC1CC(N1CCC3(CC1)CNC(=O)C3)C2]

6. The method of claim 5, wherein the reducing agent is selected from boron hydrides and silicon hydrides.

7. The method of claim 6, wherein the silicon hydride is selected from $Et_3SiH$, $HSiCl_3$, $HSiPh_3$, and $HSiPh(CH_3)_2$.

8. The method of claim 7, wherein the silicon hydride is $Et_3SiH$.

9. The method of claim 7, wherein the silicon hydride is $HSiCl_3$.

10. The method of claim 7, wherein the silicon hydride is $HSiPh_3$.

11. The method of claim 7, wherein the silicon hydride is $HSiPh(CH_3)_2$.

12. The method of claim 6, wherein the boron hydride is selected from $NaBH_4$, $NaBH(OAc)_3$, $NBu_4BH_4$, $NaBH(OAc)_3$, $NaCNBH_3$, and $NMe_4BH(OAc)_3$.

13. The method of claim 12, wherein the boron hydride is $NaBH_4$.

14. The method of claim 12, wherein the boron hydride is $NaBH(OAc)_3$.

15. The method of claim 12, wherein the boron hydride is $NBu_4BH_4$.

16. The method of claim 12, wherein the boron hydride is $NaBH(OAc)_3$.

17. The method of claim 12, wherein the boron hydride is $NaCNBH_3$.

18. The method of claim 12, wherein the boron hydride is $NMe_4BH(OAc)_3$.

19. The method of claim 5, wherein the aprotic polar or non-polar solvent is selected from xylenes, toluene, alkanes, $CHCl_3$, $CH_2Cl_2$, methyl tert-butyl ether, acetonitrile, propionitrile, tetrahydrofuran, and 2-methyl tetrahydrofuran.

20. The method of claim 5, wherein the optional acid is a $C_1$ to $C_{10}$ carboxylic acid.

21. The method of claim 20, wherein the $C_1$ to $C_{10}$ carboxylic acid is acetic acid or hexanoic acid.

22. The method of claim 5, wherein the compound of Formula B obtained before the optional purification has an exo:endo isomer ratio greater than or equal to 70:30, greater than or equal to 75:25, greater than or equal to 80:20, greater than or equal to 85:15, greater than or equal to 90:10, greater than or equal to 95:5, or greater than or equal to 99:1.

23. The method of claim 5, wherein the compound of Formula B obtained before the optional purification has an endo:exo isomer ratio greater than or equal to 70:30, greater than or equal to 75:25, greater than or equal to 80:20, greater than or equal to 85:15, greater than or equal to 90:10, greater than or equal to 95:5, or greater than or equal to 99:1.

24. The method of claim 5, wherein the compound of Formula B is further converted to a pharmaceutically acceptable salt.

25. An isolated compound which is:

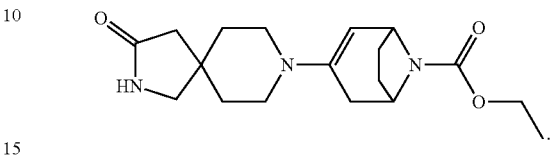

26. The method of claim 5, wherein the method also comprises contacting at reflux a mixture of a ketone of Formula C, a secondary amine of Formula D or a salt thereof, and an acidic catalyst in a non-polar solvent to obtain the compound of Formula A:

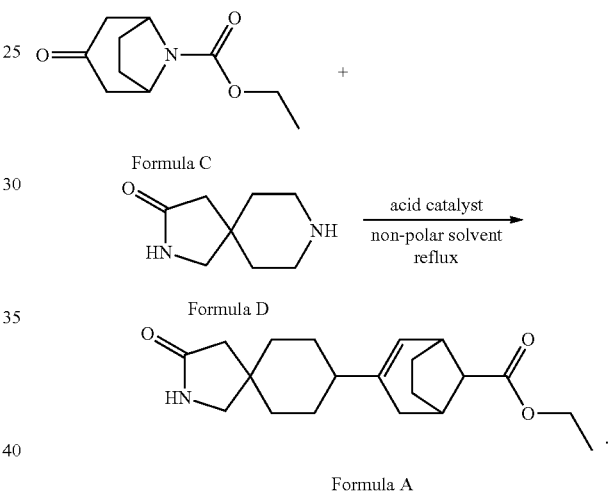

27. The method of claim 26, wherein the non-polar solvent is xylenes.

28. The method of claim 26, wherein the catalytic acid hexanoic acid.

29. The method of claim 26, wherein the water produced by the reaction between the ketone of Formula C and the amine of Formula D is removed using a sieve dryer or Dean-Stark apparatus.

30. The method of claim 26, wherein the compound of Formula A is isolated by crystallization.

31. The method of claim 30, wherein the crystallization is accomplished by cooling the reaction mixture to room temperature, adding another non-polar solvent, optionally seeding the mixture with the previously formed compound of Formula A, and collecting the solid compound of Formula A.

32. The method of claim 26, wherein the non-polar solvent is hexane, heptane, or octane.

* * * * *

UNITED STATES PATENT AND TRADEMARK OFFICE
CERTIFICATE OF CORRECTION

PATENT NO. : 10,501,483 B2
APPLICATION NO. : 16/168548
DATED : December 10, 2019
INVENTOR(S) : Danny T. Dinh et al.

Page 1 of 4

It is certified that error appears in the above-identified patent and that said Letters Patent is hereby corrected as shown below:

On the Title Page

Item [56], Column 2, under "Other Publications", Line 13, delete "Protoclol" and insert -- Protocol --, therefor.

In the Specification

Column 3, Line 2, delete "$SOR^B$," and insert -- $SOR^5$, --, therefor.

Column 3, Lines 49-50, delete "formula" and insert -- Formula --, therefor.

Column 5, Lines 60-63, delete "  " and insert -- 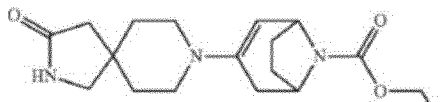 --, therefor.

Column 6, Line 9, delete "R'," and insert -- $R^1$, --, therefor.

Column 9, Lines 41-45, delete " 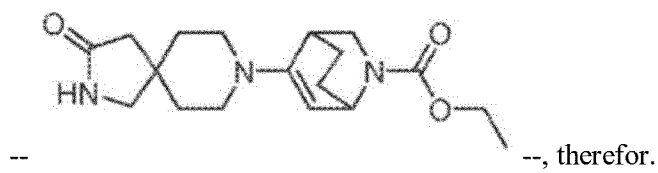 " and insert -- 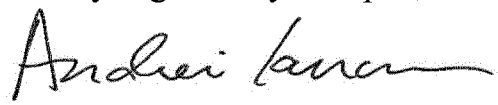 --, therefor.

Signed and Sealed this
Twenty-eighth Day of April, 2020

Andrei Iancu
*Director of the United States Patent and Trademark Office*

CERTIFICATE OF CORRECTION (continued)
U.S. Pat. No. 10,501,483 B2

Column 10, Lines 34-36, delete " 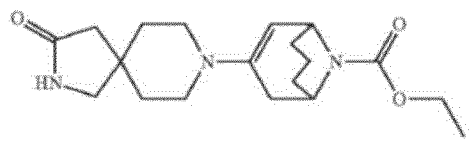 " and insert

-- 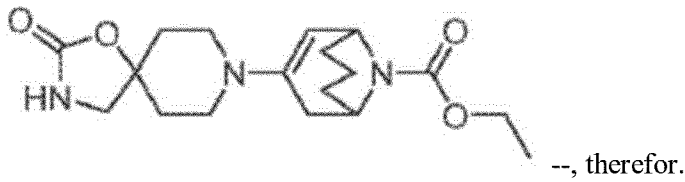 --, therefor.

Column 23, Lines 42-45, delete " 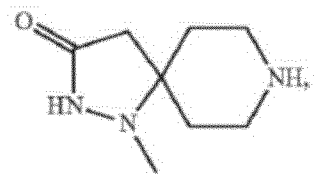 " and insert

--  ' --, therefor.

Column 29, Line 40, before "is" and insert -- p --.

Column 33, Lines 25-29, delete " 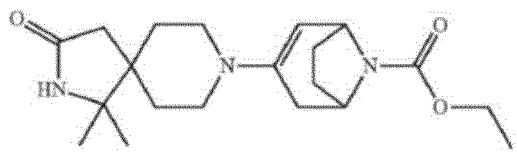 " and insert

-- 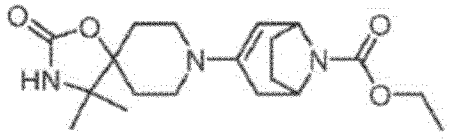 --, therefor.

Column 38, Lines 40-48, delete " 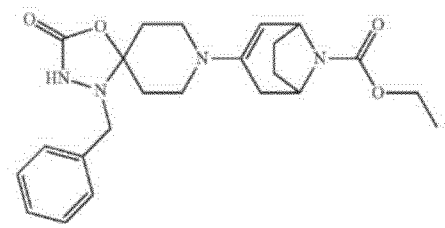 " and insert

CERTIFICATE OF CORRECTION (continued)
U.S. Pat. No. 10,501,483 B2

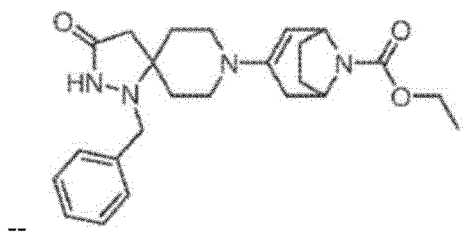

-- --, therefor.

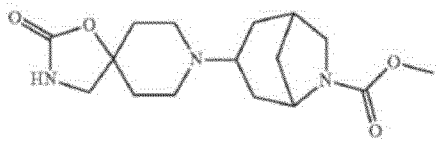

Column 50, Lines 40-44, delete " " and insert

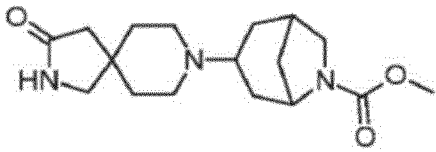

-- --, therefor.

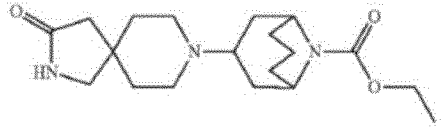

In Column 55, Lines 10-14, delete " " and insert

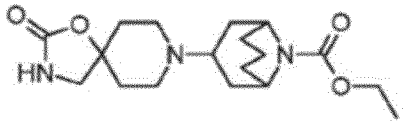

-- --, therefor.

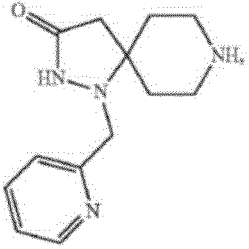 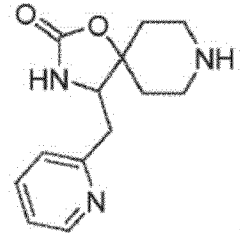

Column 63, Lines 36-44, delete " " and insert -- -- , therefor.

Column 64, Line 21, delete "diastero-" and insert -- diastereo- --, therefor.

Column 64, Line 32, after "exo)" insert -- . --.

Column 69, Line 18, after "(m" insert -- , --.

Column 69, Line 63, after "(m" insert -- , --.

In the Claims

Column 70, Line 48, Claim 1, delete "$R^2$" and insert -- $R^2$, --, therefor.
Column 84, Lines 36-40, Claim 26, delete " 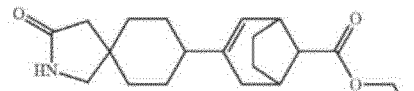 " and insert
-- 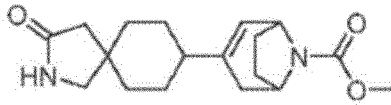 --, therefor.